United States Patent
Ganguly et al.

(10) Patent No.: US 12,186,564 B2
(45) Date of Patent: Jan. 7, 2025

(54) METHODS AND APPARATUSES FOR TREATING STROKE USING LOW-FREQUENCY STIMULATION

(71) Applicants: The Regents of the University of California, Oakland, CA (US); U.S. Government as represented by the Department of Veterans Affairs, Washington, DC (US)

(72) Inventors: Karunesh Ganguly, San Francisco, CA (US); Preeya Khanna, San Francisco, CA (US); Kyungsoo Kim, Oakland, CA (US)

(73) Assignees: The Regents of the University of California, Oakland, CA (US); U.S. Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 18/264,926

(22) PCT Filed: Feb. 9, 2022

(86) PCT No.: PCT/US2022/015876
§ 371 (c)(1),
(2) Date: Aug. 9, 2023

(87) PCT Pub. No.: WO2022/173871
PCT Pub. Date: Aug. 18, 2022

(65) Prior Publication Data
US 2024/0033516 A1 Feb. 1, 2024

Related U.S. Application Data

(60) Provisional application No. 63/147,745, filed on Feb. 9, 2021.

(51) Int. Cl.
*A61N 1/36* (2006.01)
(52) U.S. Cl.
CPC ..... *A61N 1/36103* (2013.01); *A61N 1/36139* (2013.01); *A61N 1/36171* (2013.01); *A61N 1/36178* (2013.01)
(58) Field of Classification Search
CPC .................. A61N 1/36103; A61N 1/36139
(Continued)

(56) References Cited

U.S. PATENT DOCUMENTS

| 5,871,534 A | 2/1999 | Messick et al. |
| 8,165,685 B1 | 4/2012 | Knutson et al. |

(Continued)

FOREIGN PATENT DOCUMENTS

| CA | 2623839 A1 | 4/2007 |
| CN | 1273534 A | 11/2000 |

(Continued)

OTHER PUBLICATIONS

Circstat/Pycircstat; Pycircstat:circular statistics with python; 2 pages; retrived from the internet (https://github.com/circstat/pycircstat) on Feb. 18, 2022.

(Continued)

*Primary Examiner* — Nadia A Mahmood
(74) *Attorney, Agent, or Firm* — Shay Glenn LLP

(57) ABSTRACT

Methods and apparatuses for treating a patient having a brain lesion (e.g., a stroke patient) by applying a charge-balanced, low-frequency alternating current stimulation (ACS) to a region of the patient's brain immediately before and/or during a directed movement. The charge-balanced, low-frequency ACS may have a depolarizing phase that is slower than the hyperpolarizing phase (e.g., the depolarizing phase may have a frequency of 15 Hz or less and the hyperpolarizing phase with a frequency greater than 15 Hz).

(Continued)

The ACS stimulation field may be greater than 1.5 V/m. The ACS may be applied during a preferred excitation phase.

33 Claims, 37 Drawing Sheets

(58) Field of Classification Search
USPC .......................................................... 607/45
See application file for complete search history.

(56) References Cited

U.S. PATENT DOCUMENTS

| | | |
|---|---|---|
| 11,285,321 B2 | 3/2022 | Ganguly et al. |
| 2007/0142874 A1 | 6/2007 | John |
| 2007/0213783 A1 | 9/2007 | Pless |
| 2008/0097564 A1 | 4/2008 | Lathrop |
| 2008/0319505 A1 | 12/2008 | Boyden et al. |
| 2009/0094305 A1 | 4/2009 | Johnson |
| 2010/0113150 A1 | 5/2010 | Chan et al. |
| 2012/0150262 A1 | 6/2012 | Gliner et al. |
| 2014/0194948 A1 | 7/2014 | Strother et al. |
| 2014/0200432 A1 | 7/2014 | Banerji et al. |
| 2014/0330394 A1 | 11/2014 | Leuthardt et al. |
| 2014/0350634 A1 | 11/2014 | Grill et al. |
| 2015/0065838 A1 | 3/2015 | Wingeier et al. |
| 2015/0066104 A1 | 3/2015 | Wingeier et al. |
| 2015/0081057 A1 | 3/2015 | Hamada et al. |
| 2015/0094785 A1 | 4/2015 | Kilgard et al. |
| 2015/0142082 A1 | 5/2015 | Simon et al. |
| 2015/0290457 A1 | 10/2015 | Palermo et al. |
| 2015/0321000 A1 | 11/2015 | Rosenbluth et al. |
| 2019/0022387 A1 | 1/2019 | Wagner et al. |
| 2019/0232061 A1* | 8/2019 | Ganguly ............ A61N 1/36031 |
| 2019/0380625 A1 | 12/2019 | Lindberg et al. |
| 2020/0324116 A1* | 10/2020 | Ardell ............... A61N 1/36171 |
| 2020/0353258 A1 | 11/2020 | De Ridder |
| 2020/0398058 A1 | 12/2020 | Pivonka et al. |
| 2022/0280792 A1 | 9/2022 | Ganguly et al. |

FOREIGN PATENT DOCUMENTS

| | | |
|---|---|---|
| CN | 101179987 A | 5/2008 |
| CN | 101232860 A | 7/2008 |
| CN | 103608069 A | 2/2014 |
| CN | 103764021 A | 4/2014 |
| CN | 104902806 A | 9/2015 |
| JP | H07-0736363 B2 | 4/1995 |
| JP | 2003005623 A | 1/2003 |
| JP | 2009512516 A | 3/2009 |
| JP | 2009529352 A | 8/2009 |
| JP | 2011516915 A | 5/2011 |
| JP | 201611651 A | 4/2016 |
| KR | 10-2015-0049145 A | 5/2015 |
| WO | WO2014/074638 A1 | 5/2014 |
| WO | WO2015/187712 A1 | 12/2015 |
| WO | WO2022/173871 A1 | 8/2022 |

OTHER PUBLICATIONS

Hansen et al.; The effect of transcranial magnetic stimulation and peripheral nerve stimulation on corticomuscular coherence in humans; The Journal of Physiology; 561(1); pp. 296-306; Nov. 15, 2004.
Martinez; Peripheral nerve conduction and central motor conduction after magnetic stimulation of the brain in myotonic dystrophy; Electromyography and clinical neurophysiology; 32(6); pp. 295-297; Jun. 1, 1992.
Yang Jiajia; Protective effects of exogenous VEGF on cognitive function in rats of cerebral hypoxia-ischemia model; Doctoral Dissertation; Apr. 15, 2015.
Ganguly; Twitter thread (Screenshot); retrieved from the internet (https://twitter.com/karuneshganguly/status/1360036806847156224); 6 pages; on May 12, 2022.

* cited by examiner

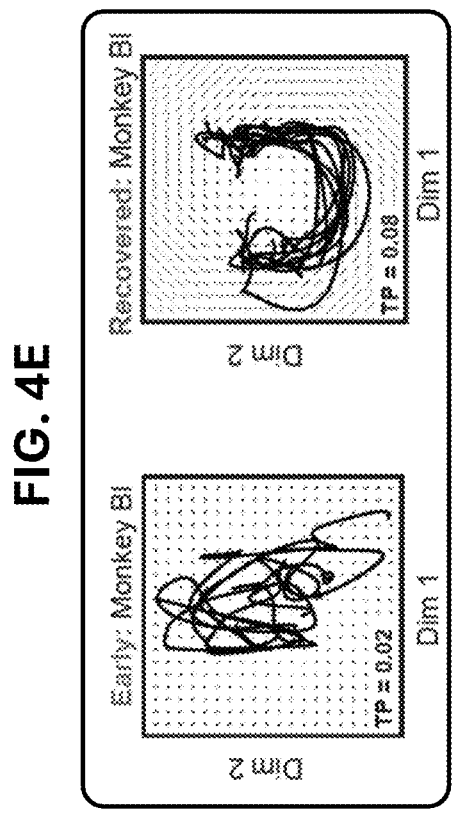
FIG. 4E
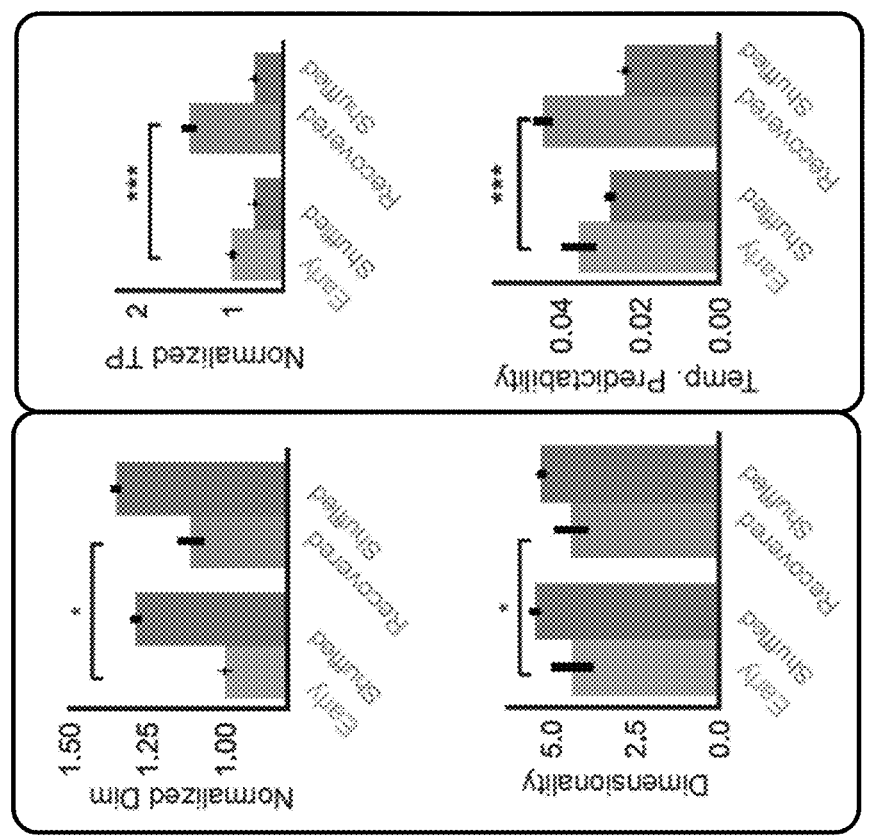
FIG. 4D
FIG. 4C

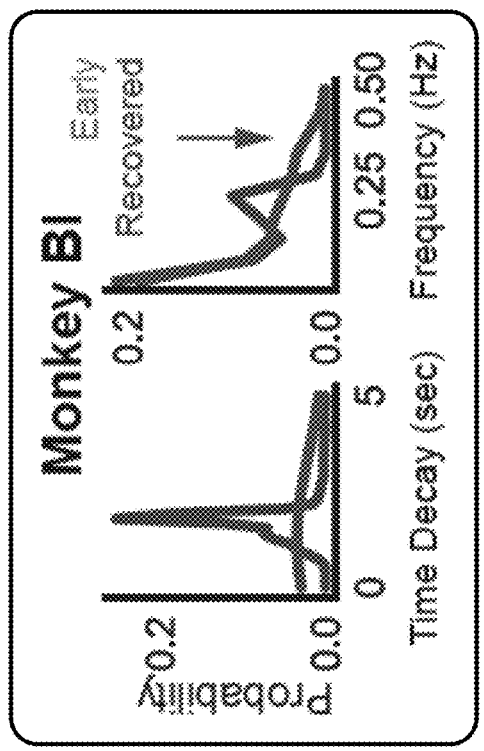
FIG. 4F
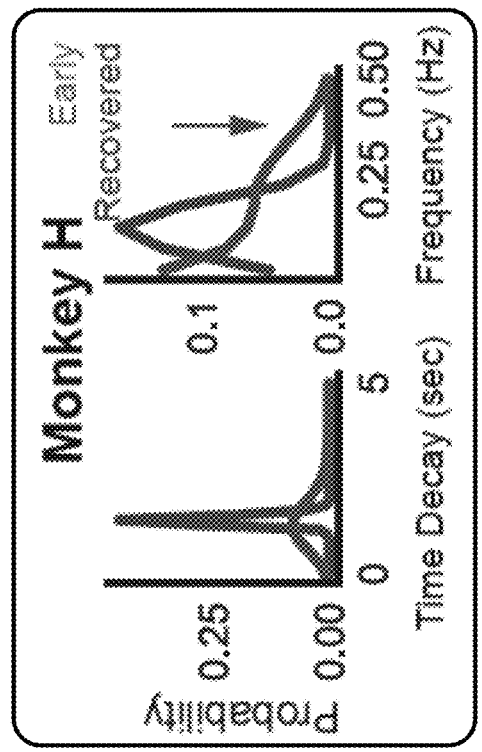
FIG. 4Gi
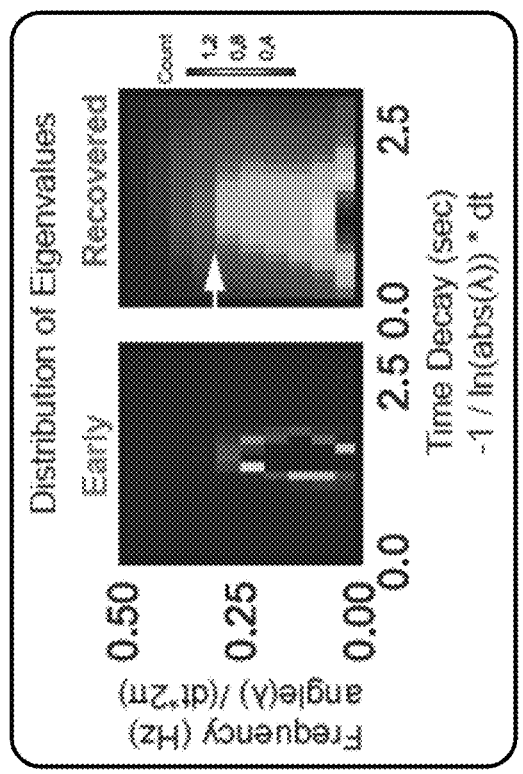
FIG. 4Gii
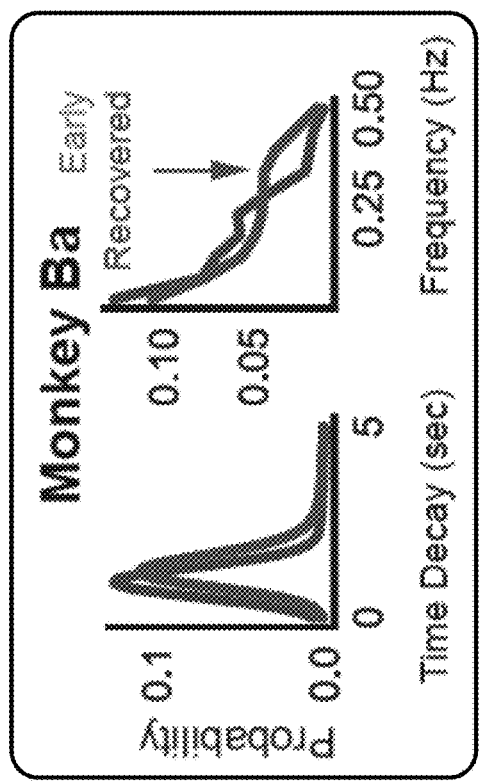
FIG. 4Giii

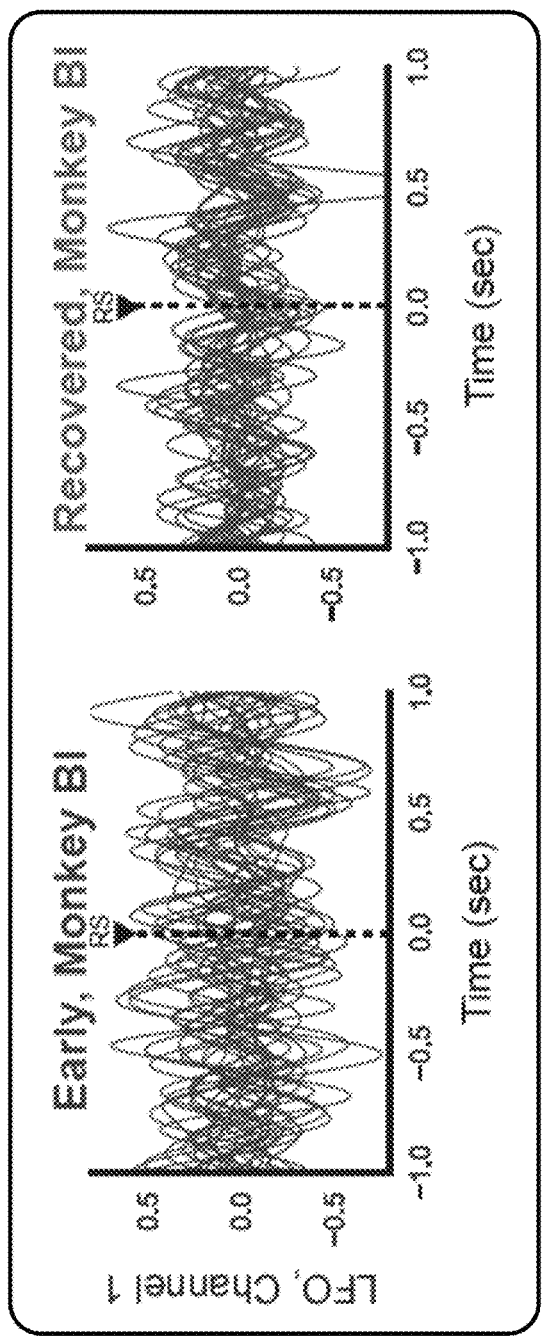
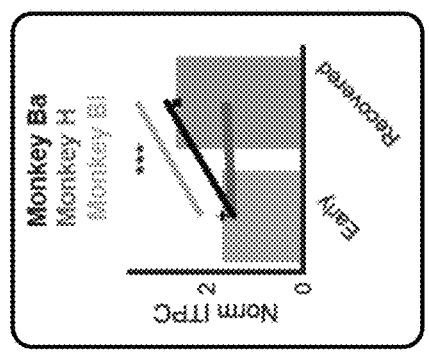
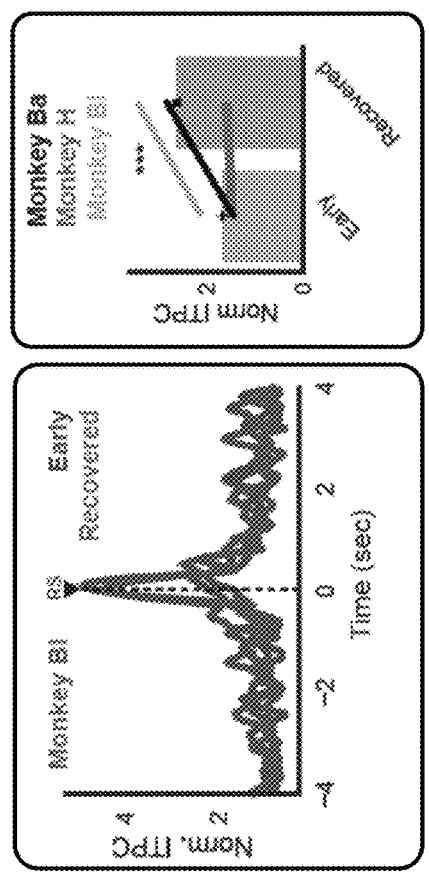
FIG. 4H
FIG. 4J
FIG. 4I

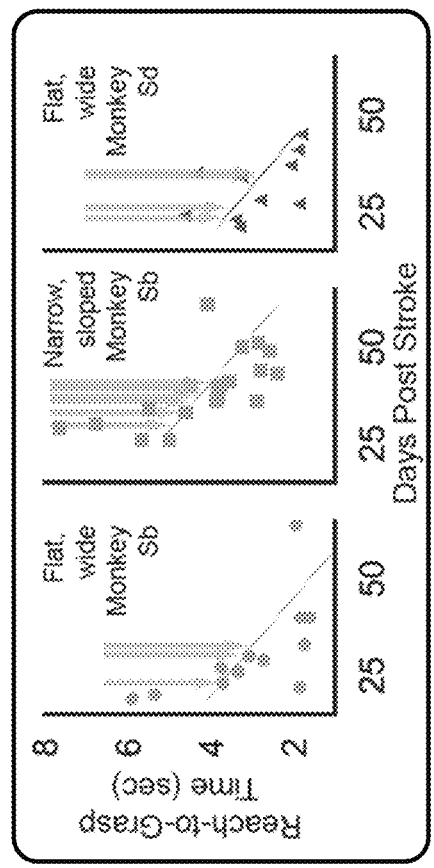
FIG. 5E
FIG. 5F
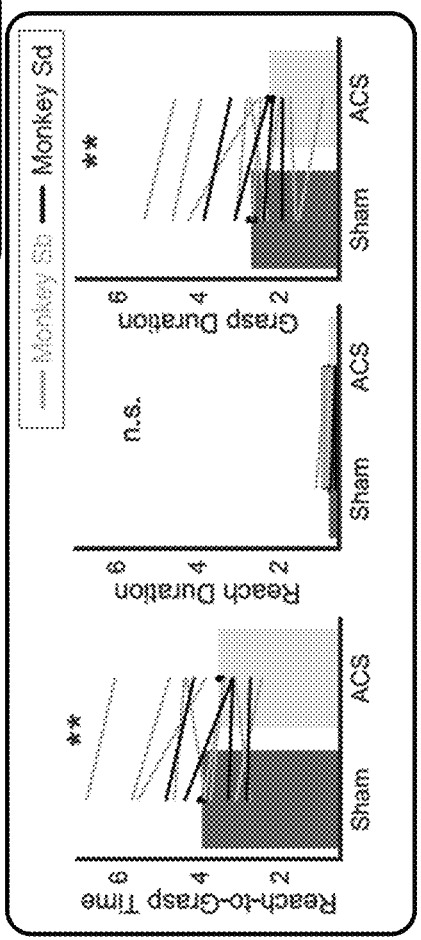
FIG. 5G
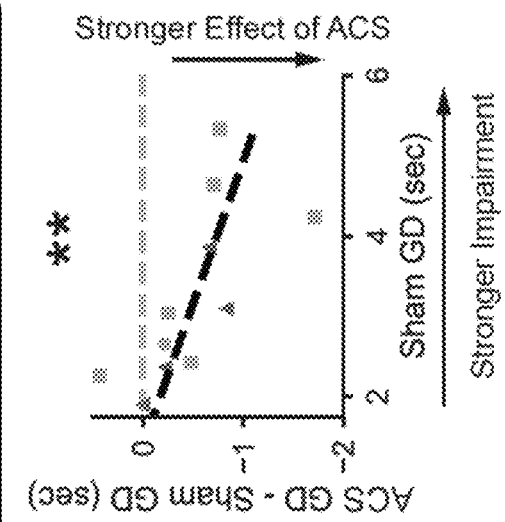
FIG. 5H

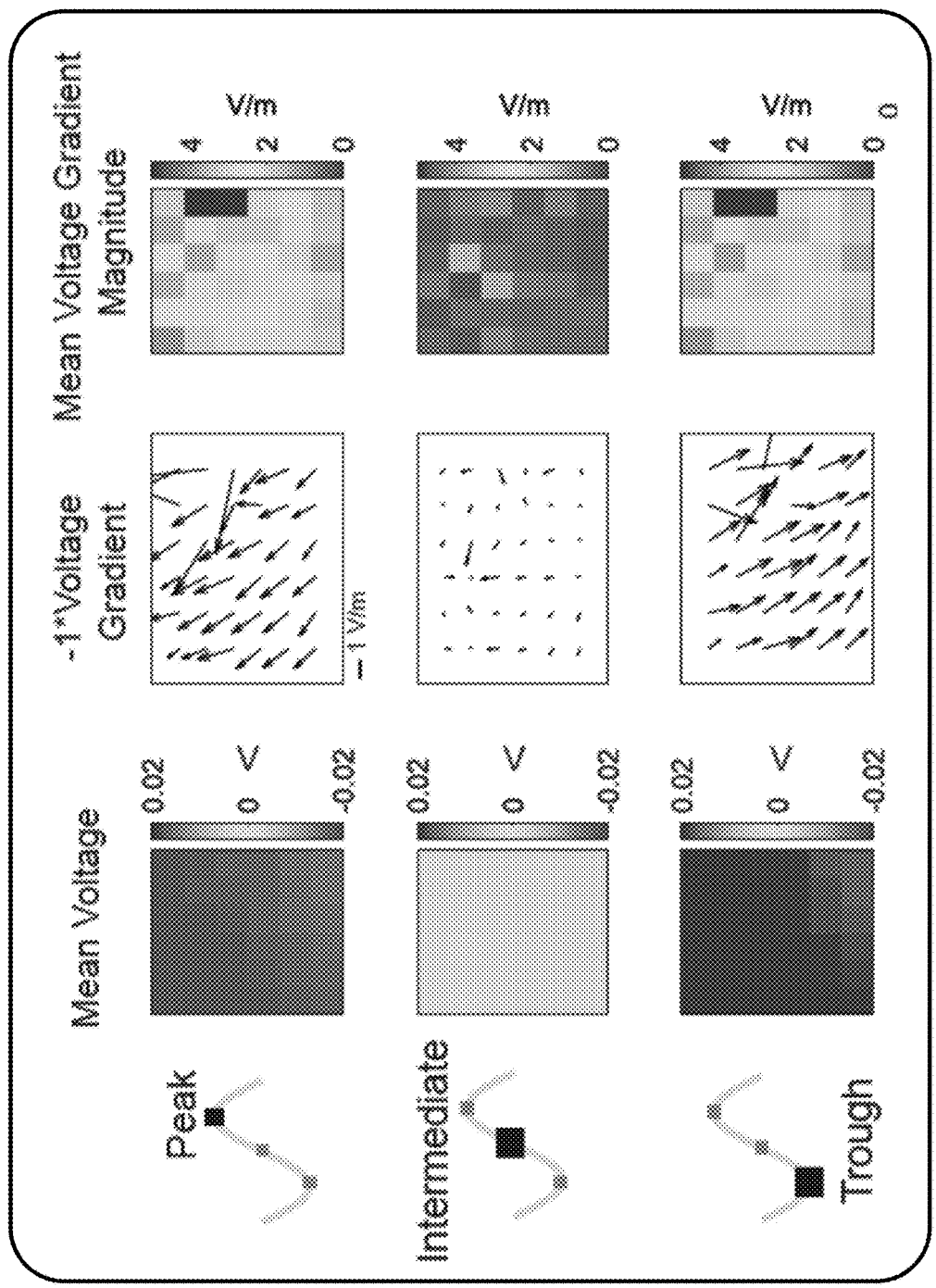
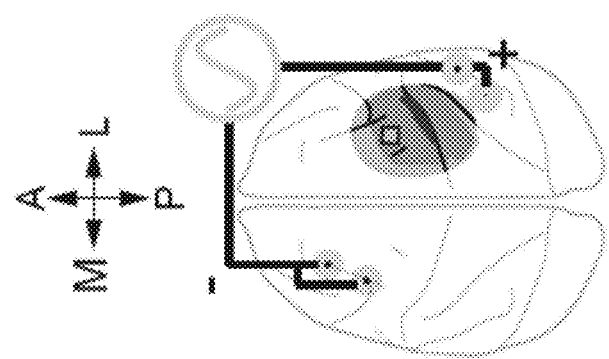
FIG. 7B
FIG. 7A

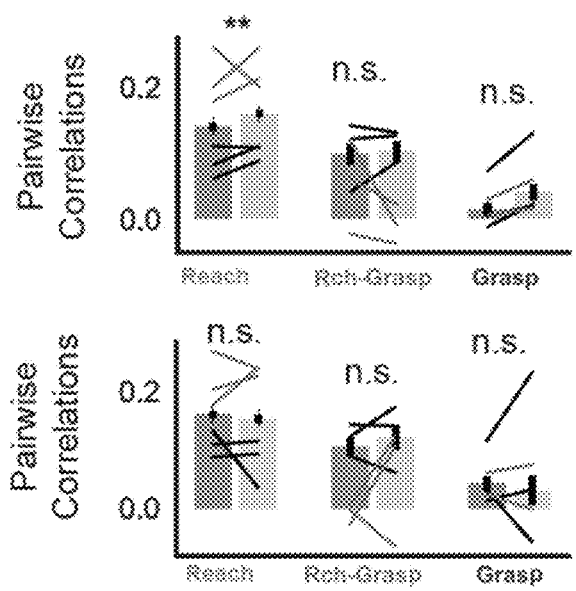
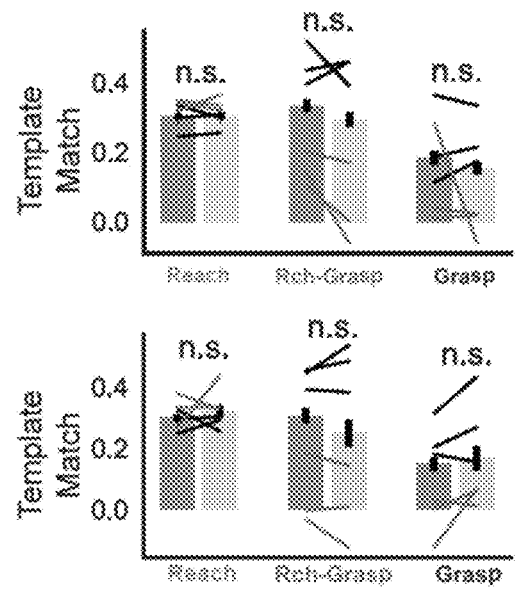
FIG. 10D
FIG. 10E
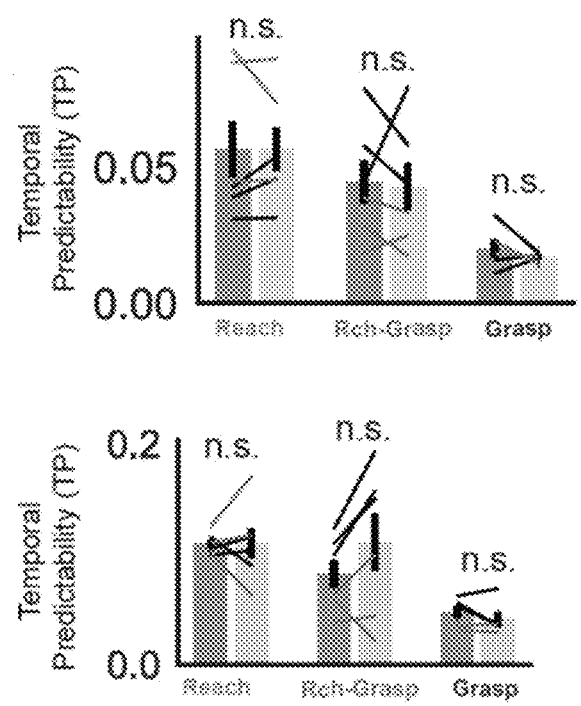
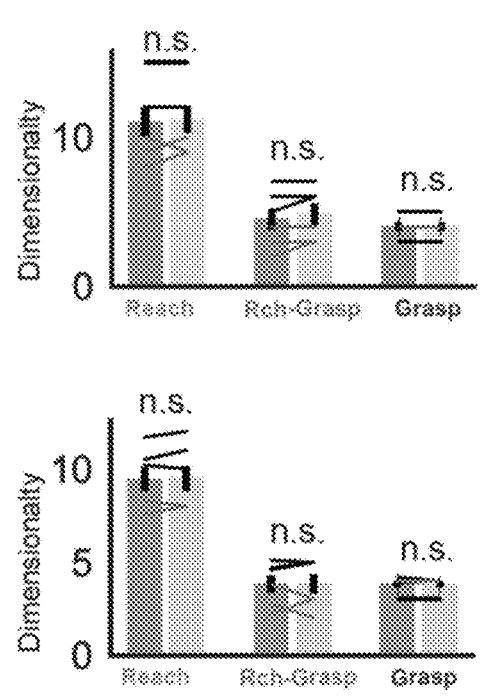
FIG. 10F
FIG. 10G

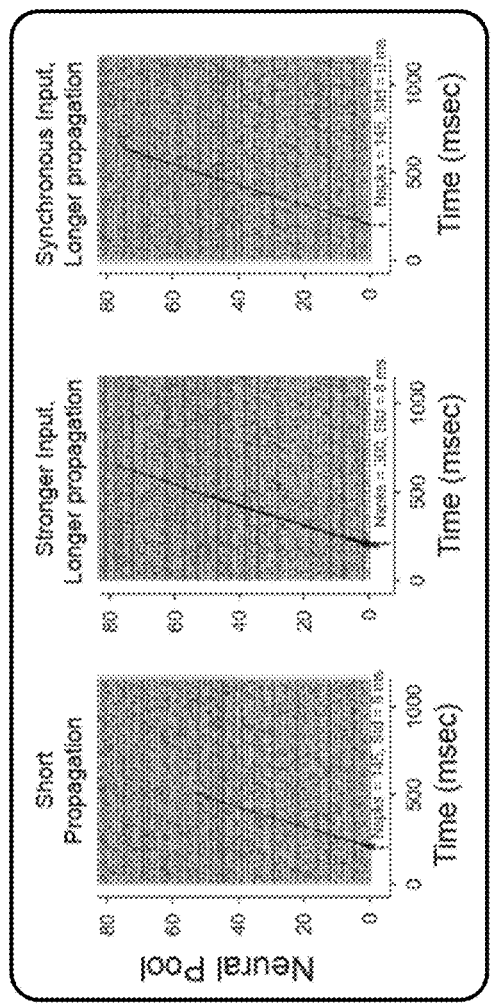
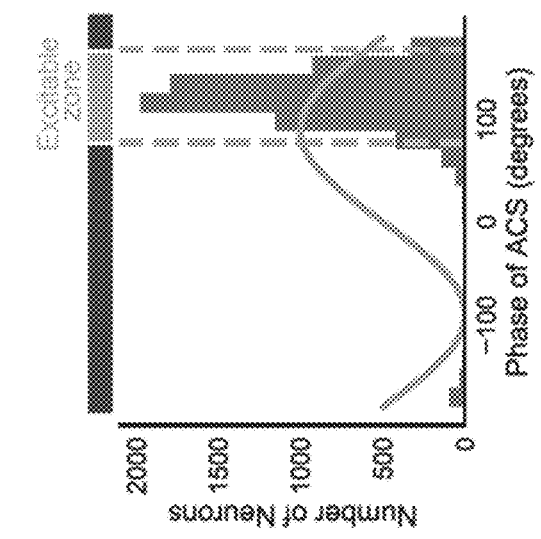
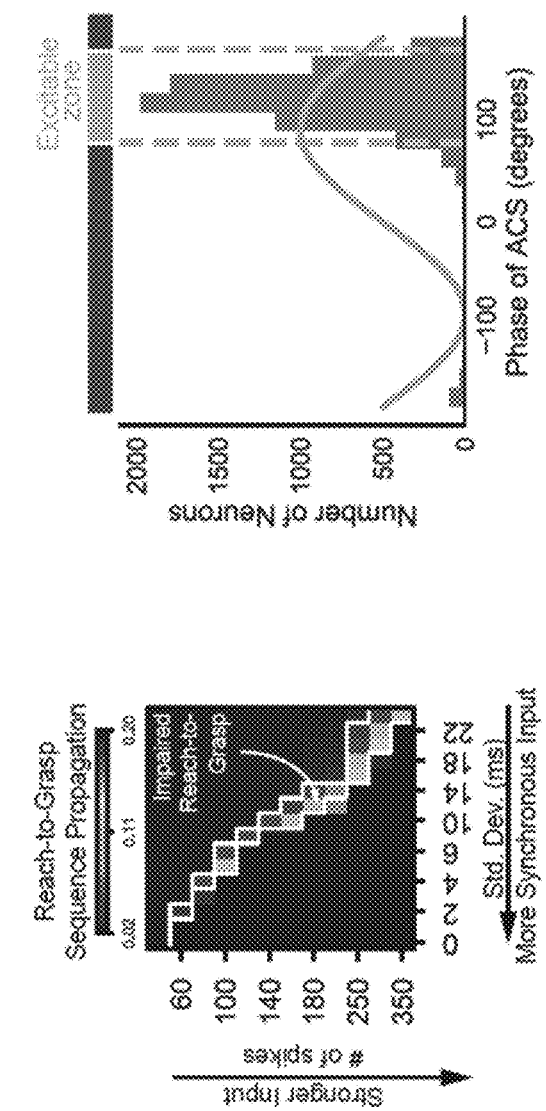
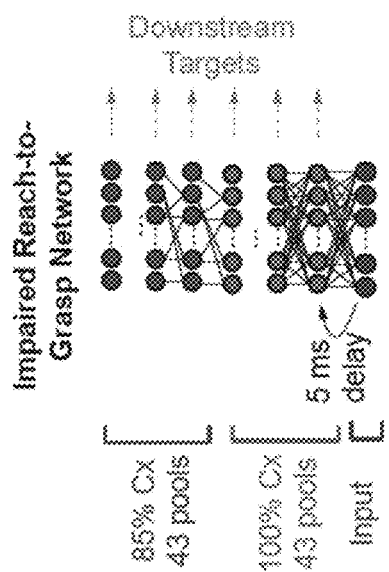
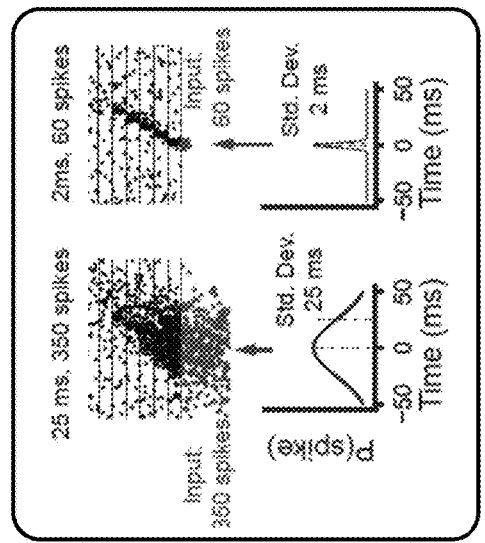
FIG. 11A
FIG. 11B
FIG. 11C
FIG. 11D
FIG. 11E

METHODS AND APPARATUSES FOR TREATING STROKE USING LOW-FREQUENCY STIMULATION

CLAIM OF PRIORITY

This patent application is a national phase application under 35 USC 371 of International Patent Application No. PCT/US2022/015876, filed Feb. 9, 2022, titled "METHODS AND APPARATUSES FOR TREATING STROKE USING LOW FREQUENCY STIMULATION," now International Patent Application Publication No. WO 2022/173871, which claims priority to U.S. Provisional Patent Application No. 63/147,745, titled "METHODS AND APPARATUSES FOR TREATING STROKE USING LOW FREQUENCY STIMULATION" filed on Feb. 9, 2021, each of which is herein incorporated by reference in its entirety.

STATEMENT AS TO FEDERALLY SPONSORED RESEARCH

This invention was made with government support under grant no. R01 NS112424 awarded by The National Institutes of Health. The government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Electrical stimulation is a promising tool for modulating brain networks. However, it is unclear how stimulation interacts with neural patterns underlying behavior, particularly in brain networks that are compromised (e.g., damaged), such as from stroke or other neural lesions. The development of novel technologies to promote motor rehabilitation after such neural lesions would be very beneficial.

From a network perspective, the brain, including the motor systems of the brain, includes a complex organization of interconnected nodes. This highly dynamic system is capable of generating finely coordinated actions as well as adapting to damage to the network. However, the electrophysiological correlates of the recovery process are poorly understood. For example, it remains unclear what electrophysiological patterns predict either recovery or the lack of recovery. Moreover, it remains unclear how to precisely modulate the motor network in order to improve function after injury.

There is a need in the art for neurostimulation apparatuses and methods for effective treatment of patients suffering from one or more neural lesions.

SUMMARY OF THE DISCLOSURE

Described herein are methods and apparatuses (e.g., systems, devices, etc., including software, firmware and hardware) for applying low-frequency alternating current stimulation (ACS) in patients recovering from a brain lesion (e.g., such as may occur during a stroke, either focal or from diffuse white matter injury) to improve task-related activity, such as, but not limited to, improving function including directed movements in regions such as the perilesional cortex. Directed movements may include, but are not limited to, movements such as reaching and grasping, speech and gait. In some examples, the low-frequency ACS may be applied epidurally. The methods and apparatuses described herein may increase co-firing within task-related ensembles and may improve dexterity. ACS as described herein may drive ensemble co-firing and enhanced propagation of neural activity through parts of the patient's neural network having impaired connectivity and may increase co-firing to enhanced dexterity. ACS as described herein may restore neural processing in impaired neuronal networks and may improve dexterity and other motor, language and cognitive function following stroke. The methods and apparatuses described herein may apply ACS stimulation to enhance target neural dynamics in a patient.

The time-varying activation of neural ensembles is an essential driver of behavior, yet it remains unknown how to precisely modulate ensembles using electrical stimulation. This knowledge gap has prevented the development of technologies that directly target the neural patterns underlying complex behaviors. Although stimulation methods to improve motor function after stroke have been proposed and initially showed some promise, translational efforts have been hampered by inconsistent results. For example, at least two recent clinical trials failed to detect a benefit of stimulation. These studies typically delivered stimulation continuously, without knowledge of the current state of neural patterns and behavior. Understanding how stimulation directly alters neural patterns and behavior has the potential to improve efficacy of such stimulation, particularly in treating stroke and related conditions. The neural patterns that produce behavior are driven by an interplay between "internal dynamics" and external environmental cues. Internal dynamics refers to the property that neural activity at a given time point can reliably predict future activity without apparent influence from external sources. Internal dynamics are likely the result of network connectivity that produces time-varying ensemble activations without need for external drive.

As described herein, electrical stimulation, which is typically insensitive to internal dynamics, may be used therapeutically to assist neural processing and boost motor function after stroke. In some examples epidural electrical stimulation may be used as a relatively less invasive technique. Externally applied fields, static or oscillatory, can grossly boost firing rates and bias spike timing. Although spiking activity (e.g., monitored during stimulation in behaving animals) has not previously been found to show expected neural changes as would be predicted from in vitro and in vivo studies, described herein are methods and apparatuses for stimulating to influence ensemble activity governed by internal dynamics.

In general, the methods and apparatuses described herein may provide external stimulation that directly interacts with impaired task-related neural patterns to improve neural processing and restore motor function following stroke. Past studies to improve motor outcomes following stroke have used continuously delivered electrical stimulation to induce long-term plasticity, with mixed clinical outcomes. In contrast, relatively little attention has been paid to how electrical stimulation immediately and directly influences task-specific neural patterns. Described herein are methods and apparatuses showing a significant improvement in dexterity with low-frequency alternating current stimulation (ACS), apparent when monitoring "perilesional" cortex (PLC) patterns during sham and stimulation in subjects recovering from either a motor or sensorimotor cortical stroke, e.g., when performing a reach-to-grasp task. ACS as described herein increased co-firing in task-related PLC ensembles during dexterous behavior. Notably, these changes resemble increases in co-firing observed during recovery. Changes in co-firing may be linked to improved function. Increases in co-firing driven by ACS allows for more reliable activity propagation. Thus, methods and apparatuses for providing oscillatory stimulation can directly modulate impaired task-related neural patterns after stroke and improve function.

In any of the methods and apparatuses described herein a neural network may be used to optimize electrical stimulation waveforms. These methods and apparatuses may modulate neural ensembles to modulate behavior, including to improve directed movements following a brain lesion such as a stroke. These methods and apparatuses may directly target the neural patterns underlying such complex behaviors and may include the use of novel stimulation waveforms that may maintain efficacy while reducing side effects. Stimulation waveform parameter spaces are notoriously large, making it challenging to sweep through all parameter combinations experimentally. Using the methods and apparatuses described herein, a network model may be used to narrow the parameter space and may provide a way to optimize parameters.

In contrast to approaches based on local brief pulse stimulation, the methods and apparatuses described herein may provide large scale modulation of networks.

In some examples deep brain stimulation pulse generators, which typically produce a narrow set of waveforms for stimulation (that may be efficacious for non-stroke conditions) may be modified as described herein to provide waveforms that are very different from the current DBS stimulation waveforms and are effective in treating stroke. Also described herein are neural networks that may provide an in-silico model system for optimizing waveforms.

Any of the methods described herein may include identifying a transfer function and/or stimulation parameters by applying, from a subcortical site, a plurality of bursts of charge-balanced, low-frequency pulses having a burst frequency of between 1-10 Hz (e.g., 1-8 Hz, 1-6 Hz, 1-5 Hz, 2-10 Hz, 2-8 Hz, 2-6 Hz, etc.), an inter-burse pulse frequency of between 10-200 Hz (e.g., between 20-180 Hz, 30-200 Hz, 40-200 Hz, 50-200 Hz, 30-180 Hz, etc.), and a pulse width of between about 0.01 ms and 2 ms (e.g., between about 0.05 ms and 2 ms, 0.1 mx and 2 ms, etc.), wherein the bursts of charge-balanced, low-frequency pulses each comprises between about 1 and 20 pulses per burst. Applying the charge-balanced, low-frequency alternating current stimulation may include using the stimulation parameters (or a transfer function) to determine the ACS. The transfer function may be applied by using the transfer function to identify one or more sets of stimulation parameters in which the evoked cortical spiking pattern is maximized, and/or for which the cortical spiking pattern is coordinated with the applied sub-cortical stimulation.

In general, the methods for determining the transfer function and/or stimulation parameters may include determining a phase locking valve between the applied subcortical charge-balanced, low-frequency alternating current stimulation and the sensed cortical spiking. A phase locking value (PLV) typically refers to a measure of the phase synchrony between two time series (e.g., subcortical stimulation and cortical firing or spiking), and may include comparison to resting state connectivity. The phase locking value may be estimated between 0 and 1, with 0 being no correlation and 1 being perfect correlation (e.g., complete entrainment). The methods and apparatuses described herein may apply phase locking analysis between the applied subcortical stimulation (e.g., charge-balanced, low-frequency pulses) and sensed cortical firing in the target region. Surprisingly the optimal phase locking value may typically be less than 1, as perfect phase locking (e.g., entrainment) may result in deleterious effects such as seizures or desensitization. For example the methods and apparatuses described herein may determine stimulation parameters (e.g., a transfer function) in which the phase locking value is between 0.5 and 0.95 (e.g., between 0.5 and 0.9, between 0.5 and 0.85, between 05 and 0.8, between 0.5 and 0.75, between 0.5 and 0.7, between 0.55 and 0.95, between 0.55 and 0.9, between 0.55 and 0.85, between 0.55 and 0.8, between 0.55 and 0.75, between 0.6 and 0.95, between 0.6 and 0.9, between 0.6 and 0.85, etc.). In some cases the method and/or apparatus may select stimulation parameters and/or transfer function in which the phase locking value is 0.95 or less (e.g., about 0.95 or less, 0.9 or less, 0.85 or less, 0.8 or less, 0.75 or less, 0.7 or less, 0.65 or less, 0.6 or less, etc.) and 0.4 or more (e.g., about 0.4 or more, 0.45 or more, 0.5 or more, 0.55 or more, 0.6 or more, 0.65 or more, 0.7 or more, 0.75 or more, 0.8 or more, 0.85 or more, etc.).

All of the methods and apparatuses described herein, in any combination, are herein contemplated and can be used to achieve the benefits as described herein.

For example, described herein are methods. For example, these methods may include methods of treating a patient recovering from a lesion (such as a stroke). The method may include: applying one or more biphasic charge balanced pulses to a region of the patient's brain in phase with units of a region of the patient's brain adjacent to a lesion in the patient's brain, wherein the units of the region of the patient's brain have a preferred excitable zone during a directed movement.

In general, as described herein, the one or more biphasic charge balanced pulses may have a depolarizing phase with a frequency of 15 Hz or less and a hyperpolarizing phase that is faster than the depolarizing phase.

For example, the one or more biphasic charged balanced pulses may comprise a charge-balanced, low-frequency alternating current stimulation (ACS). Any of the methods and apparatuses described herein may be used with one or more biphasic charged balanced pulses.

In any of these methods and apparatuses, the ACS stimulation field may be greater than 1.5 V/m (e.g., 1.6 V/m or more, 1.7 V/m or more, 1.8 V/m or more, 1.9 V/m or more, 2.0 V/m or more, etc.).

Also described herein are methods of determining the excitable zone of a brain or brain region. Any of these methods of determining the excitable zone may be included as part of a method and/or apparatus as described herein. For example, a method or process for determining an excitable zone of a brain region may include stimulating the region during non-movement periods or under anesthesia to determine a frequency and phase relationship of entrainment of the region. The frequency and phase relationship of entrainment of the region may be frequency and/or current amplitude dependent. Any of these methods and apparatuses may include determining a preferred open-loop stimulation period or a closed-loop stimulation period using the frequency and phase relationship of entrainment, where the charge-balanced, low-frequency alternating current stimulation (ACS) is applied in-phase with the preferred open-loop period or closed-loop stimulation period. Thus, in general, any of the methods and apparatuses described herein may be configured to apply stimulation (e.g., ACS) within the excitable zone of a region of the brain. For example, applying the charge-balanced, low-frequency ACS to the region of the patient's brain in phase may comprise applying the charge-balanced, low-frequency ACS within the excitable zone.

In any of these methods and apparatuses, stimulation may be applied to a connected area to generate low-frequency oscillations in the lesion.

The legion may be a premotor perilesional cortex lesion, and/or a lesion in one or more subcortical structures (e.g., in a thalamus or a striatum region of the brain).

Any of the methods and apparatuses described herein may include modifying the application of the one or more biphasic charge balanced pulses based on recordings at a site of the lesion.

Also described herein are methods of treating a patient (e.g., a patient having a brain lesion, such as a stroke patient), the method comprising: detecting a directed movement or an intended directed movement from the patient; and applying an alternating current stimulation (ACS) to the patient's brain immediately before and/or during the directed movement. The ACS may be a charge-balanced, low-frequency ACS. The ACS may have a frequency that is 15 Hz or less (e.g., between 1-15 Hz, etc.). In some examples the ACS may have a depolarizing phase with a frequency of 15 Hz or less and a hyperpolarizing phase with a frequency greater than 15 Hz. In general, the ACS stimulation field may be greater than 2 V/m.

For example, described herein are methods of treating a patient, the method comprising: detecting a directed movement or an intended directed movement from the patient; and applying a charge-balanced, low-frequency alternating current stimulation (ACS) to a region of the patient's brain immediately before and/or during the directed movement, wherein the charge-balanced, low-frequency ACS has a depolarizing phase with a frequency of 15 Hz or less and a hyperpolarizing phase with a frequency greater than 15 Hz; wherein the ACS stimulation field is greater than 1.5 V/m (e.g., 1.6 V/m or greater, 1.7 V/m or greater, 1.8 V/m or greater, 1.9 V/m or greater, 2 V/m or greater, etc.).

In any of these methods, the ACS (e.g., including, but not limited to the charge-balanced, low-frequency alternating current stimulation) may be applied in phase with units (e.g., 20% or more, 30% or more, 40% or more, 50% or more, 60% or more, etc.) of the region of the patient's brain, within an excitable zone of the units of the region of the patient's brain. For example, the ACS may be applied in phase with majority of units of the region of the patient's brain, within an excitable zone of the majority of units of the region of the patient's brain.

Applying the ACS (e.g., the charge-balanced, low-frequency ACS) to the region of the patient's brain may comprise applying the ACS to a region of the patient's brain is adjacent to a lesion of the patient's brain. The directed movement may be a reaching or reaching and grasping movement. For example, detecting the directed movement or the intended directed movement may comprise sensing brain activity (e.g., in the motor cortex). Detecting the directed movement or intended directed movement may comprises detecting an electromyographic signal. In some examples, detecting the directed movement or intended directed movement comprises detecting body motion using a motion sensor.

As mentioned, any of these methods may be methods of treating a brain lesion. For example, these methods may be methods of treating stroke (or a lesion caused by stroke).

The ACS may be applied in any appropriate manner. For example, the ACS may be applied epidurally. In some examples the ACS is applied by a plurality of electrodes implanted via a craniotomy. In some example, the ACS is applied from within a blood vessel.

As mentioned, in any of these methods and apparatuses, the ACS may be charged balanced.

Any of these methods may include suppressing the application of charge-balanced, low-frequency ACS when the patient is sleeping.

For example, described herein are methods of treating a patient recovering from a stroke, comprising: applying a charge-balanced, low-frequency alternating current stimulation (ACS) to a region of the patient's brain immediately in phase with units of a region of the patient's brain adjacent to a lesion in the patient's brain, wherein the units of the region of the patient's brain have a preferred excitable zone during a directed movement, wherein the charge-balanced, low-frequency ACS has a depolarizing phase with a frequency of 15 Hz or less and a hyperpolarizing phase that is faster than the depolarizing phase, further wherein the ACS stimulation field is greater than 1.5 V/m (e.g., 1.6 V/m or greater, 1.7 V/m or greater, 1.8 V/m or greater, 1.9 V/m or greater, 2 V/m or greater, etc.).

Also described herein are apparatuses (e.g., systems) for performing any of these methods. For example, a system for treating a patient may include: one or more sensors for detecting a directed movement or an intended directed movement from the patient; a plurality of electrodes; and a controller configured to apply a charge-balanced, low-frequency alternating current stimulation (ACS) to a the plurality of electrodes immediately before and/or during a detected directed movement, wherein the charge-balanced, low-frequency ACS has a depolarizing phase with a frequency of 15 Hz or less and a hyperpolarizing phase with a frequency greater than 15 Hz, and wherein the ACS stimulation field is greater than 1.5 V/m (e.g., 1.6 V/m or greater, 1.7 V/m or greater, 1.8 V/m or greater, 1.9 V/m or greater, 2 V/m or greater, etc.).

For example, a system for treating a patient may include: one or more sensors for detecting a directed movement or an intended directed movement from the patient; a plurality of electrodes; and a controller configured to determine an excitable zone of a phase of a plurality of units of a region of the patient's brain to which at least some of the electrodes are coupled, during a directed movement; wherein the controller is further configured to apply a charge-balanced, low-frequency alternating current stimulation (ACS) to at least some of the plurality of electrodes within the excitable zone, wherein the charge-balanced, low-frequency ACS has a stimulation field that is greater than 2 V/m.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 1B (bottom left) shows intact M1 accessed via The Scalable Brain Atlas. FIG. 1B (bottom right) shows an ex-vivo MRI from Monkey B1 illustrating lesion.

FIGS. 4A-4J illustrate changes in dimensionality, temporal predictability, and low frequency LFP oscillations with recovery, related to FIGS. 1A-1H. FIG. 4A illustrates consistency of single trial PLC neural activity tracks the recovery of dexterous function after stroke, and specific structure of single-trial neural activity patterns changed with recovery. To characterize the single trial spatiotemporal patterns, the inventors developed measures of "dimensionality" (Dim) to measure the complexity of population activity and "temporal predictability" to quantify the reliability of the temporal evolution of the neural patterns. FIG. 4A illustrates both metrics used to quantify example simulated neural data. The dimensionality measure used principle component analysis (PCA) to assess how many orthogonal principle components (PCs) were required to reconstruct 80% of PLC neural patterns on a given day during the recovery period. For the simulated example in (A, top, left), 3 PCs were needed to capture 80% of the variance expressed in the 25 simulated neurons (A, bottom left). Changes in the temporal evolution of neural activity on each day of recovery were assessed. In healthy animals performing stereotyped behaviors, neural activity patterns in the future were well explained as a linear function of current neural activity. This consistent relationship likely reflected a stable, consolidated network through which activity patterns reliably propagated to generate consistent behavior. Even in tasks that were feedback reliant, consistent temporal dynamics persisted and helped explain future neural activity. The inventors hypothesized an increase in the predictability of the temporal evolution of PLC patterns would reflect a recovered network and would correlate with improved behavior. To quantify "temporal predictability", a linear dynamics model was employed. Specifically, the change in neural activity from the current time point (t−1) to the next time point (t) was modeled as a linear function of current activity ($dX_t=X_t-X_{t-1}=AX_{t-1}$). The variance explained by this model indicated how well the model could estimate future fluctuations in neural activity i.e., "temporal predictability". Model predictions were visualized with a flow field plot (FIG. 4A, right bottom) where at each point $X_{t-1}=(x_{t-1}^1, x_{t-1}^2, \ldots x_{t-1}^N)$ in neural state space (visualized here just to be 2D space), an arrow is plotted that corresponds to the prediction for the change in activation predicted by the linear model (arrow=$AX_{t-1}$). The temporal predictability metric is then the variance of true future change in PC activity ($dX_t$) accounted for by the linear prediction ($AX_{t-1}$). If the prediction is very high, then whenever a point in PC-space is entered, it is very likely that the next point $X_t$ will be equal to $AX_{t-1}+X_{t-1}$, or that the neural trajectory will follow the flow field predictions.

FIG. 4B illustrates how spatiotemporal patterns change dimensionality and temporal predictability. Two spatiotemporal patterns were simulated. The first pattern consists of mostly co-active neurons, so the dimensionality of this pattern is low (dim=2). The temporal predictability of this pattern is also low (visualized with flow field plot at bottom). The flow field illustrates predictions made by the dynamics model, and since the neural state in the first part of the sequence (e.g. green line, B, top left) is also entered in the second part of the sequence (e.g. pink line), yet the change in direction for these two instances is opposite (activity is moving to the left for the green arrow, and to the right for the pink arrow). Thus, the linear model cannot reliably predict the change in state for the next time point since it is given data where the state is the same, but the next state is different. This feature in the data results in a low temporal predictability. The second example illustrates a simulated spatiotemporal pattern where groups of neurons are co-active at different time delays. This pattern has a higher dimensionality (Dim=4), and also has a high temporal predictability since changes in neural activity are well predicted by the flow field (B, bottom right).

FIG. 4C illustrates single-trial PLC spatiotemporal patterns increase in dimensionality and temporal predictability with recovery: Both dimensionality and temporal predictability increased with recovery. To account for differences in numbers of units and numbers of trials over recovery, metrics were computed over many iterations of subselecting units and subselecting trials, and the mean over all iterations is reported. To improve visualization, both metrics were normalized by the mean "early" animal-specific values though results are significant without normalization. First, normalized dimensionality of PLC patterns significantly increased with recovery (C, top), (mixed-effect model with animal as random effect on intercept, slope=0.094, $t(8)=2.45$, p=0.0143). However, dimensionality was still less than the full dimensionality defined by the number of observations analyzed (illustrated by comparison to the gray bars representing the dimensionality metric computed on shuffled neural data). If data is not normalized by the early sessions, dimensionality still significantly increases (mixed-effect model with animal modeled as random effect on intercept, slope=0.3145, $t(8)=2.036$, p=0.042).

FIG. 4D shows normalized temporal predictability also significantly increased with recovery (D, top), (mixed-effect model with animal modeled as random effect, slope=0.441, $t(8)=5.45$, $p=4.98 \times 10^{-8}$). Even when not normalized by early sessions TP still significantly increased with recovery (mixed-effect model with animal modeled as random effect, slope=0.0125, $t(8)=6.304$, $p=2.897 \times 10^{-10}$).

FIG. 4E shows predictions from the dynamics models (flow fields) for early and recovered conditions differed, and single trials (black lines) exhibited greater adherence to the model predictions in the recovered states exemplified in (E). These results suggest that early and recovered PLC patterns resembled the left and right examples illustrated in (B) respectively. Qualitatively, the flow fields shown as examples in (E) were different, with the early field having smaller arrows, and the late fields having larger more rotational arrows. While the TP metric quantified how well the model fits the data, it does not consider the differences in how the linear dynamics model makes predictions. One way of quantifying the types of neural dynamics that are being captured by the model is by visualizing the eigenvalue spectrum of the dynamics matrix "A". For a given n-by-n A matrix, there will be n eigenvalues corresponding to n independent dynamics "modes". Each eigenvalue has a frequency and magnitude associated with it which respectively convey i) whether the associated dynamical mode oscillates and if so, how quickly, and ii) how persistent activity is in the associated dynamical mode. Since magnitudes of eigenvalues computed from brain data are almost always stable, a common way to convey the "persistence" of a dynamical mode in a more interpretable unit is to compute the "time decay" of an eigenvalue in units of seconds. The "time decay" refers to how long it would take for a dynamical mode of activation k to decay to a value of k/e. Long time decays reflect very persistent activity, whereas short time decays reflect activity that dies out quickly.

FIG. 4F is an example from one animal and two representative sessions (early, recovered) of the distribution of eigenvalues represented in the dynamics matrix fit to data. The distribution was built over data that was subsampled to match numbers of units and numbers of timepoints used to fit the linear dynamics model. Early, eigenvalues tended to be concentrated at lower frequencies with less variety in time decays whereas later more higher frequency eigenvalues emerged (white arrow).

FIG. 4G shows distributions of eigenvalues based on time decay (left) or frequency of eigenvalue (right) for all animals (Gi-Giii) over all early and recovered sessions. Blue arrows denote the increase in higher frequency eigenvalues. Although a small effect, the inventors note that other groups have identified a computational roll for oscillations of higher frequencies. Our view of recovering neural activity is that it becomes more reliably sequential as behavior improves. In simulated sequences of neural activity (not shown), higher frequency eigenvalues emerge in linear dynamics models fit to data when i) individual units have narrower temporal modulation (e.g. units quickly activate and deactivate), ii) or when there are shorter lags between subsequently firing units (i.e. a compressed sequence). Overall, these findings are consistent with the emergence of reliable, complex network with recovery from stroke.

FIG. 4H shows a change in low frequency oscillation (LFO) phase consistency with recovery. Previous work has identified low frequency oscillations in the LFP ("LFOs") as a biomarker of recovery from stroke. Early and recovered sessions were analyzed. After pre-processing LFP signals to extract the LFO signal, intra-trial phase coherence (ITPC) was computed for all 64 electrodes in PLC for trials aligned to reach start (RS). For Monkey B1, LFO from PLC channel 1 is plotted for 25 trials on an early session (top) and recovered session (bottom).

FIG. 4I illustrates baseline-normalized ITPC for Monkey B1 for two early sessions and two recovered sessions.

FIG. 4J shows ITPC significantly increases with recovery (mixed-effect model with animal modeled as random effect on intercept, slope=0.9462, $t(766)=15.81$, p<2.56e-56).

In FIGS. 5B and 5F, the arrows (yellow) indicate stimulation sessions. Significant improvements in pellet retrieval R2G time with ACS (LME with animal, ACS day, and well size as random effects: $t_{326}=-3.08$, p=0.0021), no change in reach duration (326=0.618, p=0.537), and significant reduction in grasp duration ($t_{326}=-3.148$, p=0.00165) were observed. Bars in FIG. 5C are means (sem) over trials and each line is the mean for an animal, session, and well-size (Monkey H (B1): black (gray)).

FIG. 5E shows a schematic of pinch-and-lift task and "gripper" objects that change task difficulty. FIG. 5F shows the recovery of R2G time for two animals performing pinch-and-lift task. FIG. 5F (left) shows Monkey Sb using flat, wide grippers. FIG. 5F (center) shows Monkey Sb using narrow sloped grippers. FIG. 5F (right) shows Monkey Sd using flat, wide grippers.

FIG. 5G shows significant improvements in R2G time with ACS (LME, animal, ACS day, and gripper identity as random effects: $t_{904}=-3.143$, p=0.00167), no change in reach duration ($t_{886}=-0.401$ p=0.689), and significant reduction in grasp duration ($t_{886}=-3.104$, $p=0.00191$). Bars are mean (sem) over all trials and each black (gray) line is mean for each animal, day and grippers for Monkey Sd (Sb).

In FIG. 5H, for pinch-and-lift task, significant correlation between sham grasp duration and effect of ACS (ACS minus sham grasp duration), (LME with animal as random effect: $t_{11}=-2.708$, $p=0.00676$) is seen. Each point is the mean grasp duration for an animal, sham/ACS session pair, and gripper identity. Circles (squares, triangles) indicate data from Monkey Sb (Sb, Sd) for flat/wide (narrow/sloped, all) grippers. See also FIG. 6, showing no carryover effect of ACS, related to FIGS. 5A-5H.

FIG. 7A illustrates one example of a PLC electrode array and ACS stimulation screws (e.g., for epidural stimulation).

FIG. 7B, is a graph showing mean voltages (left), negative voltage gradient directions (middle), voltage gradient magnitudes (right) recorded on the PLC array when ACS waveform at peak (top row), intermediate point (middle row), and trough (bottom row) from an example session from Monkey Sd.

FIG. 8A (right) shows an example session from Monkey B1, average (sem) R2G times binned by ACS phase at reach start superimposed with circular histogram fit of phase.

FIG. 9A (bottom) shows normalized trial-averaged activity for sham and ACS.

FIG. 10D show a significant increase in pairwise correlations for the reach ensemble for ACS sessions compared to sham sessions, and no significant difference in pairwise correlations for the reach-grasp, grasp ensembles, and no significant difference in pairwise correlations for outside vs. inside EZ trials for any ensemble (mixed-effects model with animal and session modeled as random effects: ACS vs. sham: reach ensemble: slope=0.0199, t(2144)=2.738, p=0.00618, reach-grasp ensemble: slope=0.0038, t(268) =0.1911, p=0.8484, grasp-ensemble: slope=0.0257, t(100) =1.8557, p=0.0635. Outside EZ vs. Inside EZ: reach ensemble: slope=−0.0076, t(2144)=−0.9553, p=0.3394, reach-grasp ensemble: slope=0.0156, t(268)=0.6333, p=0.5265, grasp ensemble: slope=−0.0113, t(100)=−0.4377, p=0.6616). Bars indicate means+/−s.e.m across all pairs of units over all monkeys and sessions. Black and gray lines correspond to means over all unit pairs for each session pair from Monkey H and B1 respectively.

FIG. 10E show that there are no significant difference in template matching for ACS vs. sham or inside EZ vs. outside EZ for any ensemble (mixed-effects model with animal and session modeled as random effects: ACS vs. sham: reach ensemble: slope=0.0, t(407)=−0.1105, p=0.912, reach-grasp ensemble: slope=−0.03, t(407)=−1.45, p=0.146, grasp ensemble; slope=−0.03, t(407)=−1.236, p=0.2165, Outside vs. inside EZ; reach ensemble; slope=0.01, t(211)=0.776, p=0.438, reach-grasp ensemble: slope=0.00, t(211)=0.1223, p=0.9027, grasp ensemble: slope=0.06, t(211)=1.746, pv=0.0808). Bars indicate means+/−s.e.m across all trials over all monkeys and sessions. Black and gray lines correspond to means over trials for each session pair from Monkey H and B1 respectively.

FIGS. 10F and 10G show that there are no significant differences in temporal predictability (FIG. 10F) or dimensionality (FIG. 10G) for ACS vs. Sham conditions for any ensemble or Inside EZ vs. Outsize EZ for any ensemble. Temporal predictability, mixed-effects model with animal and session modeled as random effects: ACS vs. sham: reach ensemble, slope=0.0002, t(10)=0.043, p=0.966, reach-grasp ensemble, slope=−0.0017, t(10)=−0.2035, p=0.839, grasp ensemble: slope=−0.0031, t(8)=−0.8803, p=0.379. Outside vs. Inside EZ: reach ensemble, slope=0.0003, t(10)=0.0265, p=0.979, R2G ensemble: slope=0.029, t(10)=1.811, p=0.070, grasp ensemble: slope=−0.0063, t(8)=−1.1852, p=0.2359. Dimensionality, mixed-effects model with animal and session modeled as random effects: ACS vs. sham: reach ensemble, slope=0.1667, t(10)=0.5423, p=0.5876. reach-grasp ensemble, slope=0.333, t(10)=1.581, p=0.114, grasp ensemble, slope=0.0, t(8)=0.0, p=1.0. Outside vs. Inside EZ: reach ensemble, slope=0.0667, t(10)=0.4385, p=0.661, reach-grasp ensemble, slope=−0.0167, t(10)=−0.064, p=0.949. grasp ensemble, slope=−0.020, t(8)=−0.4082, p=0.683. Bars indicate means+/−s.e.m across all estimates of TP and Dim over all monkeys and sessions. Black and gray lines correspond values of TP and Dim for each session pair from Monkey H and B1 respectively.

FIG. 11A illustrates a neural network with input (red), fully connected (gray) and impaired subnetwork (purple).

FIG. 11B shows an example of statistics of input spikes ($\sigma$, N) influence sequence propagation: left: (8 ms, 145 spikes), center: (8 ms, 300 spikes), and right: (0 ms, 145 spikes).

FIG. 11C illustrates impaired R2G input parameters. Left, 25 ms, 350 spikes, Right 2 ms, 60 spikes.

FIG. 11D shows an example of sequence propagation for input parameters ($\sigma$, N) on x, y axes. Pixels inside white boxed regions correspond to impaired R2G input parameters.

FIG. 11E illustrates a distribution of preferred phases of simulated neurons during ACS (gray bars). EZ is centered on circular mean of distribution (+/−$\pi$/4).

In FIG. 13A, each row corresponds to an isolated unit. Column 1 shows mean ACS (yellow) and sham (black) waveform (+/−s.d.), SNR for sham (ns) and ACS (st) are printed in the title. CoD corresponds to the coefficient of determination between the mean ACS and sham waveforms. Titles in red reflect units rejected because of CoD <0.75. Column 2, 3: Raster plots of unit for sham (column 2) and ACS (column 3) conditions aligned to reach start. Column 4: Normalized PETH aligned to reach start (yellow trace=ACS, black trace=sham). Column 5, 6: Interspike interval distributions for unit times in Sham (column 5) and ACS (column 6) condition. Firing rate for each condition is printed in the title.

FIG. 13B illustrates the distributions of metrics for all units isolated from Monkey B1. Red sections indicate values of metrics which result in unit rejection. From right to left: i) CoD, rejection for CoD <0.75, ii) ACS waveform SNR, rejection for SNR <1.5 (not shown), iii) ACS firing rate (FR), rejection for FR<0.5 Hz, iv).

FIG. 13C shows estimates of ACS waveform noise overlap, rejection for noise overlap <0.5. FIG. 13C is the same as FIG. 13A for Monkey H.

FIG. 13D is the same as FIG. 13B for Monkey H.

FIG. 15 is a table (table 1) showing examples of animal contributions to stimulation and recovery results and analysis related to some of the examples described herein.

FIG. 16 is a table (table 2) showing examples of neural network modeling parameters related to some of the examples described herein.

FIG. 17 shows an example of an electrical stimulation pulse waveform (e.g., a charge-balanced low-frequency alternating current stimulation).

FIGS. 18A-18D show examples of parametric assessment of low-frequency oscillations in cortex as a function of varying electrical stimulation parameters (similar to those shown in FIG. 17) in thalamus. The trace at "0" is an average across multiple channels. The black dots are single spikes from neurons. The top trace is the population spike rate. FIGS. 18A-18D had a biphasic pulse width of 0.3 ms. FIG. 18A shows single pulses at a 3 Hz interval, FIG. 18B showed bursts of 3 pulses at a 3 Hz interval, FIG. 18C showed bursts of 5 pulses at a 3 Hz interval, and FIG. 18D shows bursts of 8 pulses at a 3 Hz interval.

FIGS. 19A-19D show examples of parametric assessment of low-frequency oscillations in cortex as a function of varying electrical stimulation parameters (similar to those shown in FIG. 17) in thalamus. The trace at "0" is an average across multiple channels. The black dots are single spikes from neurons. The top trace is the population spike rate. FIGS. 19A-19D had a biphasic pulse width of 0.5 ms. FIG. 19A shows single pulses at a 3 Hz interval, FIG. 19B showed bursts of 3 pulses at a 3 Hz interval, FIG. 19C showed bursts of 5 pulses at a 3 Hz interval, and FIG. 19D shows bursts of 8 pulses at a 3 Hz interval.

FIGS. 20A-20D show examples of parametric assessment of low-frequency oscillations in cortex as a function of varying electrical stimulation parameters (similar to those shown in FIG. 17) in thalamus. The trace at "0" is an average across multiple channels. The black dots are single spikes from neurons. The top trace is the population spike rate. FIGS. 20A-20D had a biphasic pulse width of 1.0 ms. FIG. 20A shows single pulses at a 3 Hz interval, FIG. 20B showed bursts of 3 pulses at a 3 Hz interval, FIG. 20C showed bursts of 5 pulses at a 3 Hz interval, and FIG. 20D shows bursts of 8 pulses at a 3 Hz interval.

FIGS. 21A and 21B are plots showing average beta power (power at beta frequencies between 10-40 Hz) during movements (e.g., grasp) at 13 days post-stroke and 20 days post stroke, respectively. Signals showing beta power are shown over time (prior and after start of movement) for 64 channels recorded from a single subject.

FIG. 22 schematically illustrates one example of a system as described herein.

DETAILED DESCRIPTION

Figure 1C:
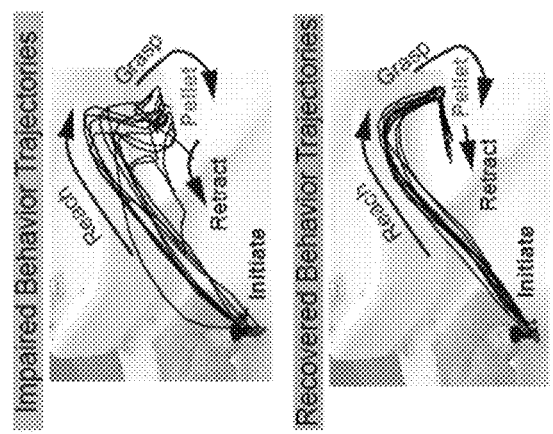
FIG. 1C is an example of index finger trajectories from one subject (Monkey H) during an intermediate session (top) and following full recovery (bottom).

The methods and apparatuses described herein may generally include low-frequency ACS to improve dexterity, e.g., in stroke patients. In some examples, these methods and apparatuses may be configured to apply to patients epidurally. In some examples, these methods may be applied via more invasive techniques (e.g., craniotomy). The application of low-frequency ACS as described herein to treat stroke may significantly improve dexterity in directed movements, such as reach to grasp (R2G) tasks. The low-frequency ACS stimulation described herein, particularly when applied during targeted times (immediately before and/or during the directed movement(s)) may significantly and surprisingly improve dexterity in a phase-dependent manner. For example, the methods and apparatuses described herein may result in task-related ensembles that exhibit increases in co-firing for trials with reach starting inside increase neural excitability (EZ). As shown herein, these increases in co-firing improve activity propagation. Thus, externally applied ACS as described herein can interact with and enhance internal processing and restore dexterity after stroke.

As will be shown in greater detail below, recovered task-related activity is largely comprised of a sequence of monophasic neural activations. Sequential structure may be present during well learned R2G tasks in intact animals. A neural network model designed to produce sequential activity has been shown to exhibit increases in template matching, dimensionality, and temporal predictability with increasing internal connectivity. The methods and apparatuses described herein may enhance stroke interrupted network function and PLC connectivity, with these methods and apparatuses reinstating reliable, high-dimensional, predictable activity patterns. These methods may provide a population where units are monophasically activated at consistent time lags and may produce rotational dynamics. Sequential activity during R2G tasks may reflect a sequential drive of proximal then distal muscles. Alternatively, motor cortical areas may not directly generate movement, instead sequentially coordinating downstream areas that drive movement. Sequential patterns may also serve a role in maintaining timing between sub-movements, higher level task timing, or tracking sensory feedback. How exactly sequential activity is related to movement control is unclear, but the methods and apparatuses described herein may provide behavioral recovery following M1 damage concomitantly with the re-emergence of reliable, temporally predictable, neural sequences in the PLC.

In general, the neuromodulation described herein may entrain neural activity. Specifically, the low-frequency ACS described herein may directly influence network activity and improve dexterity. For example, epidural ACS entrains ~60% of recorded units (as seen in awake-behaving animals), more than in previously possible. When restricted to putative single-units, ~23% are entrained. In any of the methods and apparatuses described herein, the stimulation fields may be, e.g., between about 2-4 V/m (e.g., greater than 1.2 V/m, greater than 1.3V/m, greater than 1.4 V/m, greater than 1.5 V/m, greater than 1.6 V/m, greater than 1.7 V/m, greater than 1.8 V/m, greater than 1.9 V/m, greater than 2 V/m, between about 2 V/m and about 10 V/m, between about 2 V/m and about 8 V/m, between about 2 V/m and about 6 V/m, between about 2 V/m and about 5 V/m, etc.). In addition, the frequency of stimulation may be between about 0.1 Hz and 15 Hz (e.g., between about 0.5 Hz and 15 Hz, between about 1 Hz and 15 Hz, 15 Hz or less, less than 15 Hz, etc.). In some variations the neuromodulation applied may be applied to one or more regions (including a distributed region) such as gyrated regions of cortex, lissencephalic regions of cortex, subcortical targets such as the thalamus and the striatum, etc.

In general, the phase of the low-frequency ACS may be specified; in some examples the phase of the low-frequency ACS may be adjusted depending on the patient and/or the patient activity. For example, PLC units may exhibit different phase preferences, and the methods and apparatuses described herein may adjust the phase of the applied low-frequency ACS accordingly; the identified phase may be applied to provide higher efficacy. In some examples two or more phase preferences may be selected; both preferences may be at maximal voltage gradient magnitudes, but in some examples in differed in gradient direction. The direction of current flow may affect neural modulation.

Low-frequency ACS may increase task-related PLC ensemble co-firing in a phase-dependent manner, mirroring phase-dependent dexterity improvements. For example, epidural stimulation using ACS may drive changes in task-related ensemble spiking. When ACS increased ensemble co-firing using a metric termed herein "one dimensional shared over total variance" (1D-SOT, phase-dependent), sequence propagation improved. Propagation is a proxy for directed movements, such as reach to grasping behavior. Thus low-frequency ACS-driven increases in co-firing resulted in improved behavior of directed movements. Further, in the brain, each "pool" likely has a downstream target (subcortical network or muscle). Thus, increased co-firing within the network may also assist with propagation to subcortical targets. The methods and apparatuses described herein, including low-frequency ACS, may boost neural propagation. The methods and apparatuses described herein may also use feedforward sequences, e.g., including embedded within randomly connected networks or cortical networks to produce sequential activity. The low-frequency ACS described herein may interact with recurrently connected networks with both excitatory and inhibitory populations.

As will be described in greater detail below, the open-loop low-frequency ACS described herein may improve dexterity in stroke patients. This low-frequency ACS may be applied by any appropriate technique, including, but not limited to, epidural, deep brain stimulation and/or subdural stimulation. In some examples, cranial screws may be used to deliver epidural stimulation that is relatively less invasive compared to deep brain stimulation or subdural stimulation. Moreover, cranial screw-based stimulation may avoid concerns regarding current shunting through the skin, muscle, skull, or neck in non-invasive approaches. Current paths taken due to current shunting may modulate peripheral nerves or off-target brain regions. Although current shunting through the skull is possible, the most likely path was via the craniotomy (the surgical "defect"), which may be covered with non-conductive bone cement, thus making extracranial peripheral stimulation unlikely.

The methods and apparatuses described herein may be used either invasively or non-invasively for modulation of cortical structures and may be used for motor cortical strokes and/or sensorimotor stroke.

The application of ACS as described herein may result in long-term plasticity. In some examples, longer stimulation sessions result in carryover effects. For example, ACS-driven increases in co-firing may improve dexterity and assist in PLC network recovery through Hebbian plasticity mechanisms.

LFP low frequency oscillations (LFOs) consistency increased with recovery. Further, direct current stimulation improved reaching and increase task-related LFO power and ACS increased co-firing. Thus, increased LFO power may reflect co-firing that is boosted with stimulation to enhance behavior. Interestingly, as described herein, stimulation was most efficacious when delivered at specific times with respect to behavior. For example, ACS was efficacious when the start of the directed movement (e.g., reach start) aligned to the EZ. Thus, the method and apparatuses described herein may be closed-loop or open-loop; in particular, the methods and apparatuses described herein may reduce total current injected and may align the EZ to the onset of movement based on the input from one or more sensors to detect and/or predict the onset of movement.

For example, epidural stimulation may be triggered by input from one or more sensors (e.g., motion sensors, electromyogram sensors, or the like) triggering the application of low-frequency ACS in a patient recovering from a stroke to induce changes in task ensemble co-firing underlie and improve dexterity.

EXAMPLES

Figure 1B:
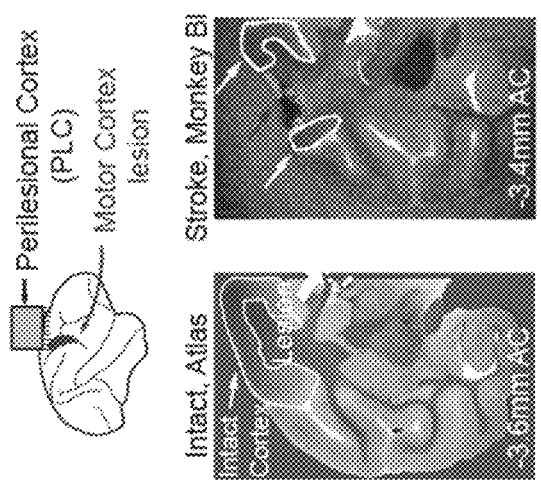
FIG. 1B (top) shows an example of a lesion, and an electrode array location for application of low-frequency ACS as described herein.
Figure 1A:
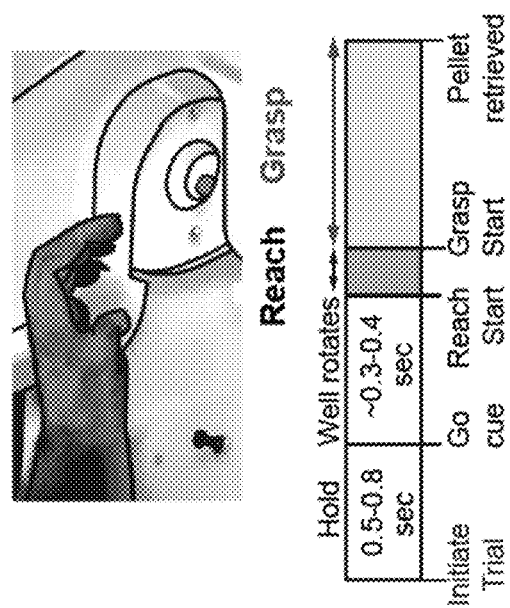
FIG. 1A illustrates an example of a directed movement (e.g., arm reach and grasp) used as part of an animal model, showing a pellet retrieve task paradigm.

In some examples, the methods and apparatuses described herein may be used for the recovery of dexterity from a stroke, such as an M1 stroke. FIGS. 1A-1H illustrate improved behavior and consistency of PLC sequential firing with recovery in a primate model. In one example, Rhesus macaques were trained to perform a pellet-retrieval task, as shown in FIG. 1A. FIGS. 2A-2D illustrate pre-stroke behavior and kinematic trajectories with recovery. Animals retrieved pellets from wells of varying diameters. Trial time varied depending on well size. Animals were trained until performance plateaued. Next, animals underwent stroke induction in which the right hemisphere primary motor cortex (M1) arm and hand area was targeted with surface vessel occlusion followed by subpial aspiration.

Surgical images were used to illustrate lesions (as shown in FIGS. 2A-2D). In a subset of animals, ex-vivo MRIs confirmed lesion location (see, e.g., FIG. 1B and FIG. 3). In the same surgery, microwire electrode arrays were implanted in the PLC. Following a period of recovery, animals were behaviorally tested.

As expected, behavior improved over time. Example index finger trajectories from impaired and recovered trials are plotted in FIG. 1C. Early in recovery, animals were slow at performing the task for the more difficult, smaller wells. When animals fully recovered, they could quickly retrieve the pellet from all wells. Recovery was quantified by measuring "reach duration" (time to transport hand from "start" to the well), "grasp duration" (from end of reach to having stable control of the pellet), and "reach-to-grasp time" (sum of reach and grasp, hereafter R2G). These metrics were normalized by their respective average pre-stroke times on the same well size. For successful trials, there were significant improvements in normalized R2G time (LME, animal as random effect $t_{544}=-6.161$, $p=7.22\times10^{-10}$), normalized reach duration ($t_{544}=-4.457$, $p=8.31\times10^{-6}$) and normalized grasp duration ($t_{544}=-5.902$, $p=3.58\times10^{-9}$).

Consistent sequential neural patterns emerged with recovery. Changes in task-related neural activity over recovery were examined. Single units in PLC were binned, temporally smoothed, and z-scored. Single trial PLC patterns were then compared to a template of behaviorally successful PLC patterns per session. Session-specific templates were computed since the exact single-unit population recorded varied over recovery. Behavior in single trials early in recovery was slower on average, but a subset of trials was executed quickly and successfully. Averaging PLC activity over these fast, rewarded trials on each day of recovery yielded a template that estimated the PLC pattern for successful behavior. See, e.g., FIG. 1E, left column.

Figure 1E:
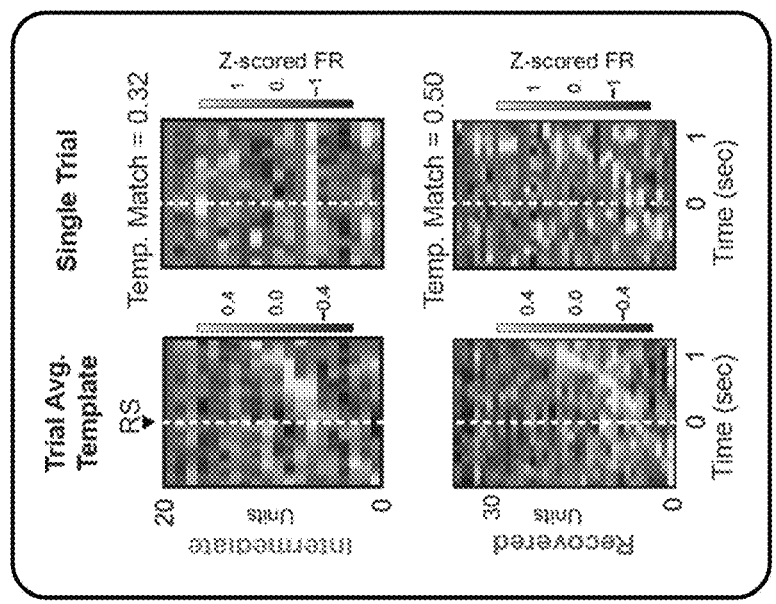
FIG. 1E shows examples of fast, successful trial-averaged templates (left column) and single trials (right column) aligned to reach start (RS) during "intermediate" recovery (top row) and full recovery (bottom row).
Figure 1D:
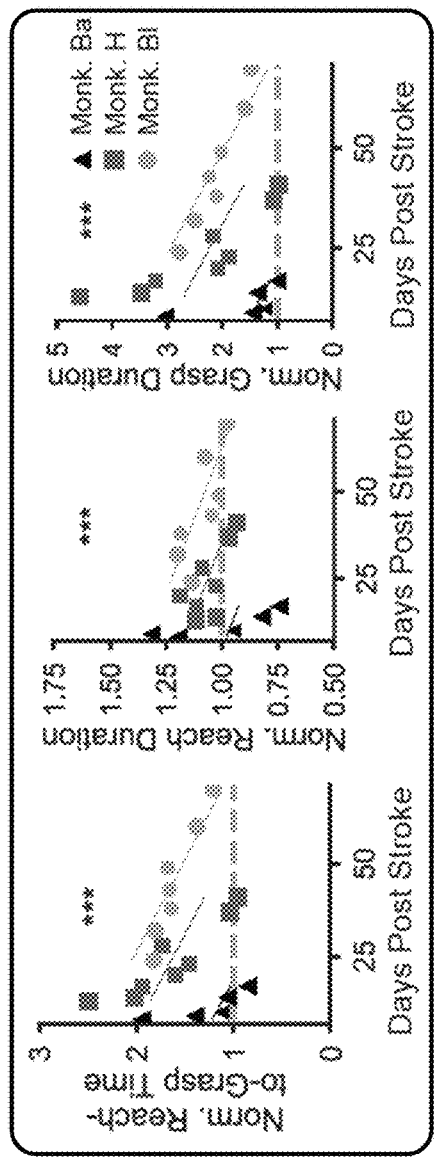
FIG. 1D illustrates behavioral improvements in 3 animals performing the pellet task. Baseline normalized R2G (LME with animal as random effect, $t_{544}=-6.161$, $p=7.22\times10^{-10}$), normalized reach duration ($t_{544}=-4.457$, $p=8.31\times10^{-6}$), and normalized grasp duration ($t_{544}=-5.902$, $p=3.58\times10^{-9}$) over recovery. Lines show LME fits with animal-specific intercepts.
Figure 1G:
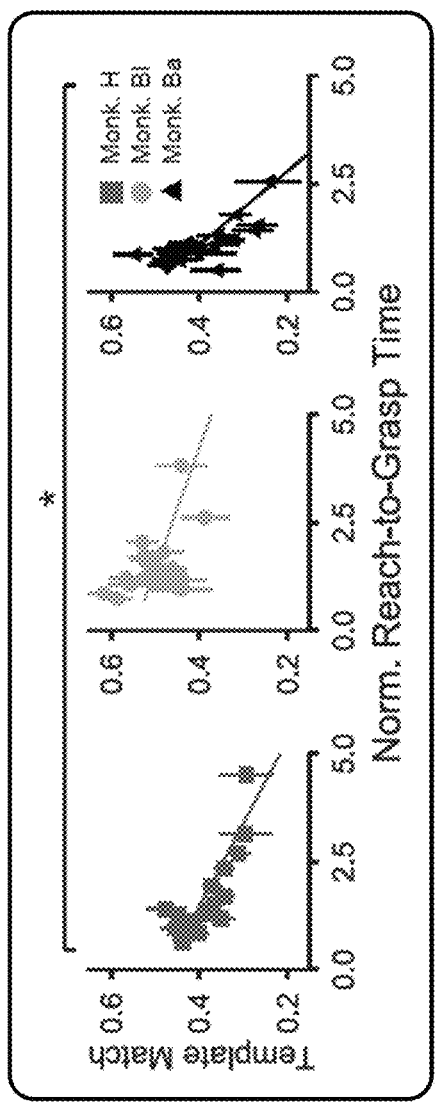
FIG. 1G shows graphs illustrating that normalized R2G time is significantly negatively correlated with template match (LME, animal as a random effect on slope and intercept: $t_{58}=-2.409$, $p=0.016$). Individual points are means (sem) of trials binned into twenty equal sample size bins based on normalized R2G times. Lines indicate animal-specific slope and intercept fit by LME model.
Figure 1H:
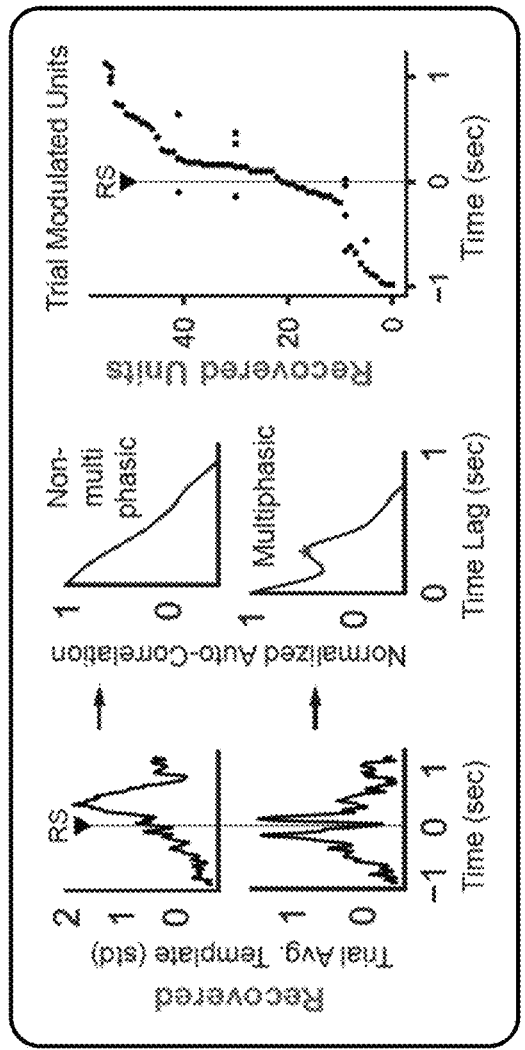
FIG. 1H shows examples of non-multiphasic and multiphasic trial-averaged unit activity aligned to reach start (RS), quantified by assessing if the autocorrelation (middle column) exhibited a significant peak between 0.1-0.5 seconds. (Right) Timing of peak (non-multi phasic) or peaks (multiphasic) of trial-averaged activity for task-modulated units pooled over three animals.
Figure 1F:
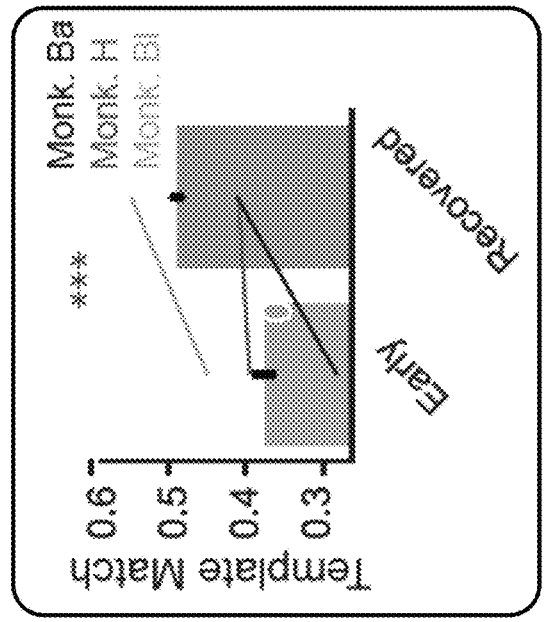
FIG. 1F illustrates template match over recovery (LME with animal as random effect, $t_{334}=6.193$, $p=5.92\times10^{-10}$). Bars indicate mean (sem) over trials. Gray lines indicate average trend per animal.
Figure 2A:
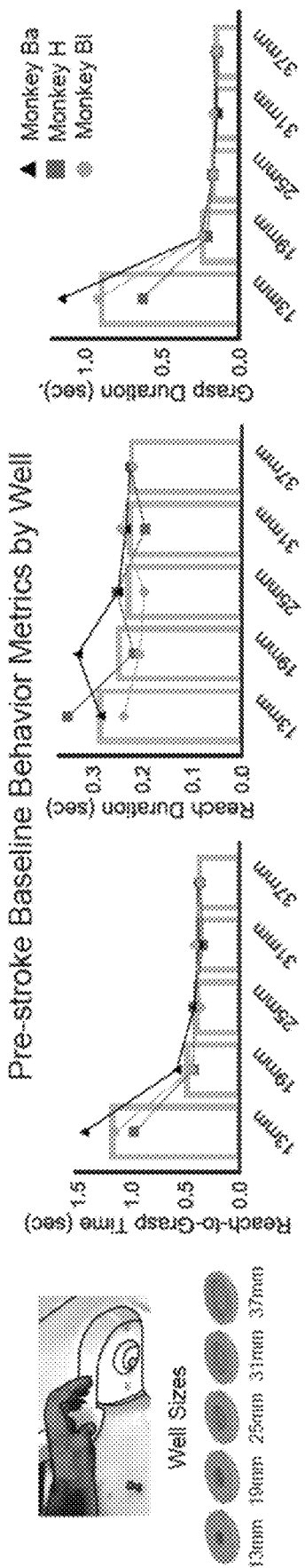
FIG. 2A (Left) Illustrates the pellet retrieval task. Bottom left: CAD images of 3D printed wells with differing diameters. Smaller diameter wells make pellet retrieval more difficult. Right: Average pre-stroke behavior for each metric and each well size. Lines indicate different animals.
Figure 2B:
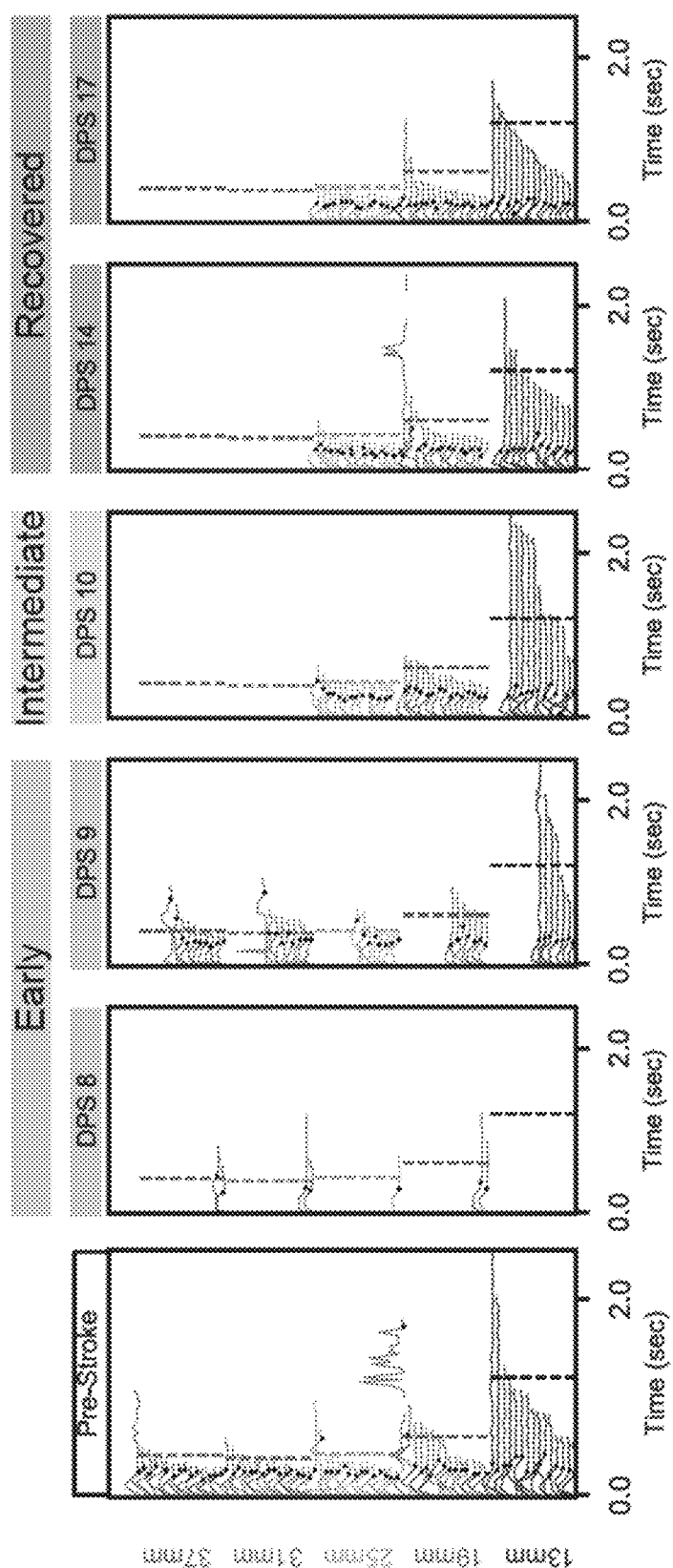
FIGS. 2B-2D show kinematic speed traces for individual trials over the course of recovery. Traces reflect speed (change in pixels) of the following joints: (B, Monkey Ba): index proximal interphalangeal joint, (C, Monkey B1): index fingertip, (D, Monkey H post stroke day 13-20): index metacarpophalangeal joint, (D, Monkey H post stroke day 23-41): thumb tip. Different joints were used for different animals due to slightly different camera positions that affected which joints were consistently visible over the course of the trial. Camera position was adjusted between day 20 and day 23 of Monkey H's recovery, hence different joints are plotted for the first and second halves of recovery. Joints were tracked using DeepLabCut (Mathis et al., 2018). Trials were plotted from reach start (time=0 seconds) to grasp finish. Grasp start is illustrated with a black dot. The first 15 successful trials (or all trials if fewer than 15) per well are plotted. Trials for a given well are sorted by R2G time. Dashed vertical lines indicate pre-stroke baseline mean for each well. Abbreviations: DPS=days post stroke.
Figure 2C:
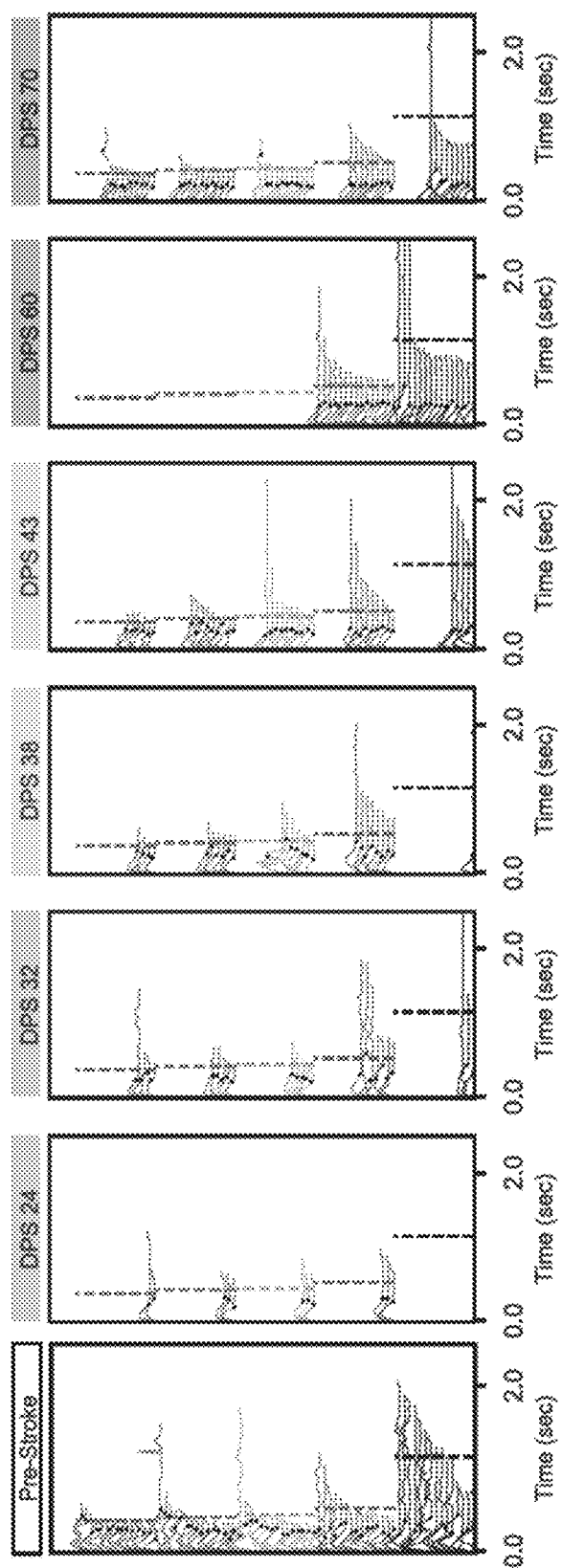
Figure 2D:
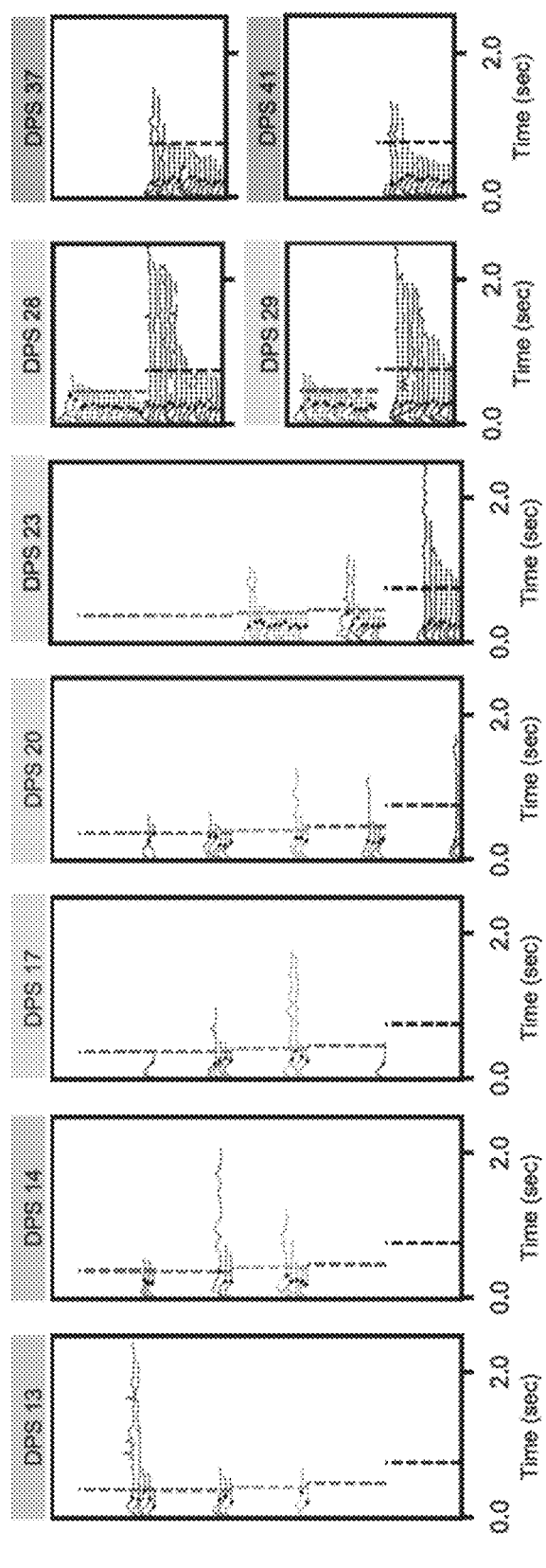

Similarity of single trials to the trial-averaged template tracked improvements (see, e.g., FIGS. 1F-G). Similarity was estimated by computing the correlation coefficient ("template match") between single trials and the template. Differences in numbers of units and numbers of fast, rewarded trials over recovery were accounted for by averaging template match estimates for each trial over many templates sub-selected to match unit and trial numbers. Example trial templates from an impaired (top) and recovered (bottom) sessions are shown in FIG. 1E left; single trials from the same session are shown in FIG. 1E right. There was an increase in template match with recovery. To quantify this, the first two sessions post-stroke with more than 5 rewarded trials were designated as "early", and the sessions in which R2G trial times were not significantly different than the pre-stroke behavior were designated as "recovered". All sessions in between "early" and "recovered" were designated as "intermediate". Since different animals had different rates of recovery, "early", "intermediate", and "recovered" stages were determined for each animal.

Figures 4A, 4B:
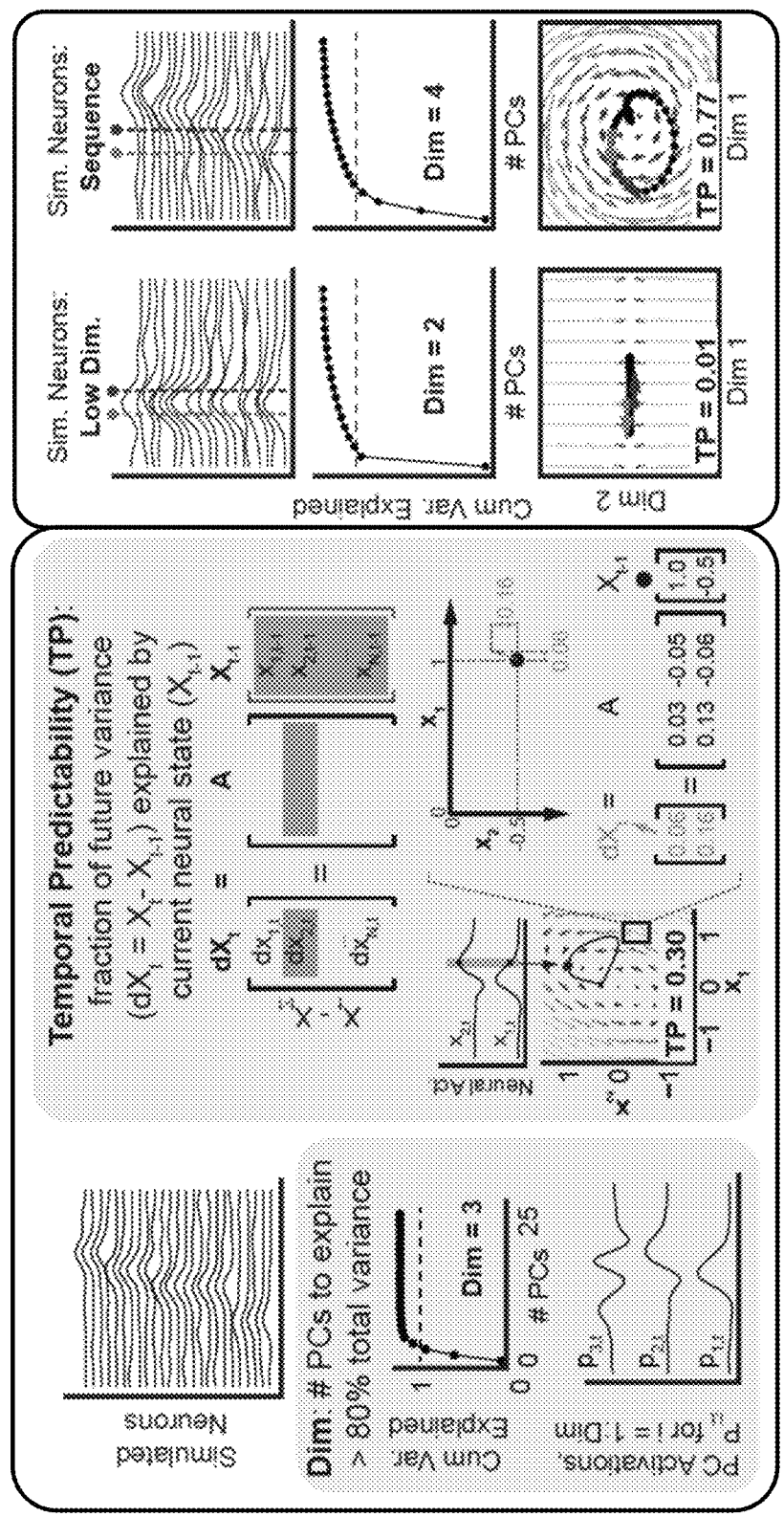

Single trial template matching significantly increased over recovery (FIG. 1F, LME with animal as random effect $t_{334}=6.193$, $p=5.92\times10^{-10}$). To assess if template match improvements correlated with behavioral improvement, linear regression was conducted between normalized R2G time and template match. For visualization, trials were grouped into twenty equally sized bins based on normalized R2G time and averaged into a single point. Mean of binned template matching was significantly negatively correlated with mean of binned normalized R2G time (FIG. 1G, LME with animal as a random effect on slope and intercept: $t_{58}=-2.409$, $p=0.016$). Thus, with recovery, PLC activity became more similar to a template for successful behavior. The low frequency band of the local field potential (LFP) was also examined to determine if it exhibited changes in consistency. An increase in low frequency LFP phase consistency with recovery was observed, as shown in FIGS. 4H-J.

The underlying spatiotemporal structure of spiking in the recovered state was further characterized and found to resemble a sequence of physically active units. Sequential patterns are high dimensional and exhibit consistent temporal structure; increases in dimensionality and predictability of single trial temporal dynamics with recovery were observed (see, e.g., FIG. 4A-4G). To further elucidate the structure of PLC patterns, trial-averaged activity was analyzed (as shown in FIG. 1H) to assess what fraction of units were sparsely active (monophasic) versus multiphasic. Aggregated over all three animals and recovered sessions, 22.0% of units were classified as multiphasic. Units were further classified as task-modulated, and of these, only 8.9% were multiphasic. FIG. 1H (right) illustrates the timing of the peaks of all task-modulated mono and multiphasic units. Thus, task-modulated units in the recovered state were primarily monophasic and population activity was high dimensional and temporally predictable, consistent with a sequential structure.

Epidural ACS Enhances Dexterity

Figure 5A:
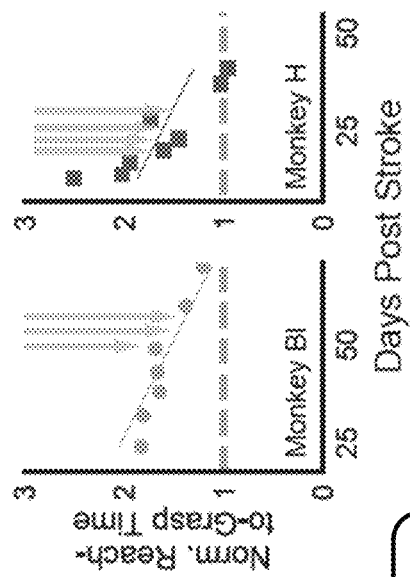
FIG. 5A shows recovery of normalized R2G time for two animals performing pellet retrieval task.
Figure 5B:
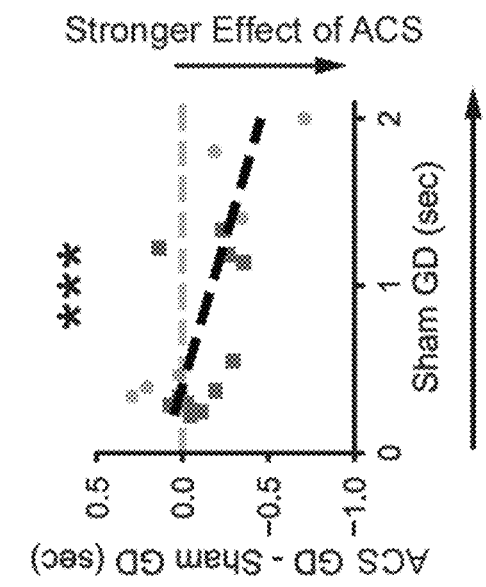
FIGS. 5B and 5C show results from a pellet retrieval task.
Figure 5C:
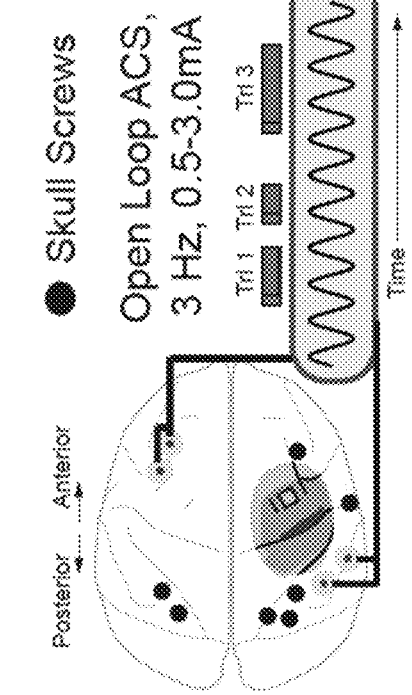
Figure 5D:
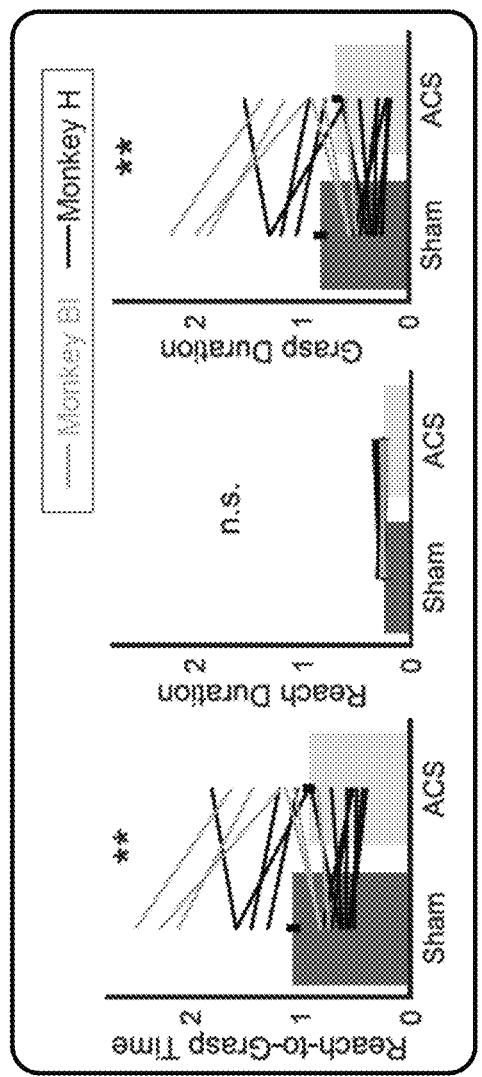
In FIG. 5D, for pellet retrieval task, significant correlation between sham grasp duration and effect of ACS (ACS minus sham grasp duration), (LME with animal as random effect: $t_{16}=-3.456$, p=0.000547) was observed. Each data point is the mean grasp duration of all trials for an animal, paired sham/ACS session, and well-size. Squares (circles) indicate data from Monkey H (B1).

When animals were in the impaired "intermediate" stage, 3 Hz ACS was delivered on a subset of sessions (FIGS. 5A-5B, yellow arrows). In this stage, reaching had largely recovered, but grasping deficits remained. ACS was compared to sham sessions that were performed on the same or an adjacent day. Session order was randomized. Low frequency ACS was chosen as a compromise between DCS, which was previously shown to improve R2G in rat stroke models, and a charge-balanced paradigm which may be part of an invasive device was used. ACS was turned on during behavioral sessions (open loop, lasting 10-15 minutes) without intentional alignment to trial structure (FIG. 5A). ACS was off outside of behavioral sessions. ACS was delivered between pairs of stainless steel or titanium cranial screws positioned posterior to the lesion in the right hemisphere and anterior to the lesion in the left hemisphere (FIG. 5A, FIG. 15 (table 1) for animal-specific doses). FIGS. 5A-5H illustrate examples of open-loop epidural ACS improving dexterity. An open-loop epidural ACS stimulation protocol was used, as shown in FIG. 5A. Epidural ACS improved dexterity in the pellet-retrieval task. ACS significantly reduced total R2G time (LME with animal, ACS day, and well size as random effects: t326=−3.08, p=0.0021), driven by a significant reduction in grasp duration (t326=−3.148, p=0.00165), and no significant change in reach duration (t326=0.618, p=0.537), as shown in FIG. 5C.

In some cases, ACS improved dexterity in a separate R2G task, the "Pinch-and-Lift" task (see, e.g., FIGS. 5E and 5F). One of these two animals received a motor cortical stroke (as previously described), while the second animal (Monkey Sd) received a sensorimotor stroke that included both M1 and primary somatosensory cortex (see, e.g., FIGS. 5A-5D). The task required use of the thumb and index fingers to lift an object from a slot (FIG. 5E). In contrast to the pellet retrieval task this task could only be accomplished using a pincer grip. Thus, behavioral improvements could not simply be due to compensation with another grasp type. ACS significantly reduced R2G time (LME with animal, ACS day, and gripper identity as random effects: t904=−3.143, p=0.00167), which was also driven by a significant reduction in grasp duration (t886=−3.104, p=0.00191), and no significant change in reach duration (t886=−0.401 p=0.689) (FIG. 5G).

For both sets of animals, the greater the impairment, the greater the efficacy of ACS. Grasp duration impairment (grasp duration during sham sessions, x-axis), was significantly correlated with how strongly ACS improved grasp duration (ACS minus sham grasp duration, y-axis, FIG. 5D, pellet retrieval task, LME with animal as random effect: t16=−3.456, p=0.000547, FIG. 5H, pinch-and-lift task: t11=−2.708, p=0.00676). While this correlation may arise from a floor effect since the amount that grasp durations can reduce is limited, large impairments may benefit from ACS.

Figures 6A, 6B:
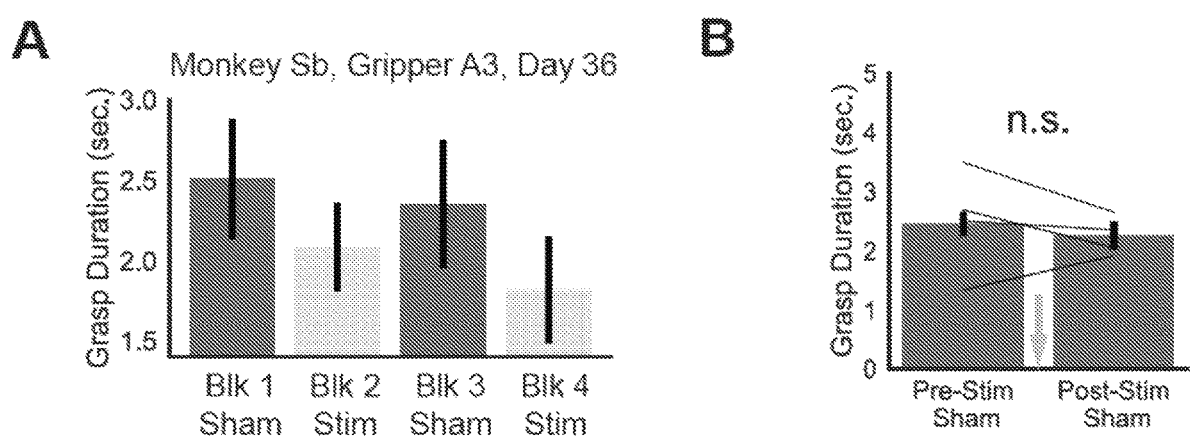
FIG. 6A shows an example session with interleaved ACS and sham sessions for Monkey Sb on gripper A3 on Day 36 post stroke. Grasp durations are faster in stimulation sessions, but there do not appear to be strong differences between the sham sessions Blk1 and Blk3 despite the intermediate Blk2 ACS session.
FIG. 6B shows aggregated data over two animals performing the pinch-and-lift task (pellet retrieval task was never performed with a block structure suitable for this analysis) in which a sham block came before any ACS for the day, and a sham block came after ACS. Four days of stimulation testing distributed over the two animals performing the pinch-and-lift task were included in this analysis. There was no significant difference between pre-ACS sham and post-ACS sham (mixed-effect model with animal, ACS day, and gripper identity as fixed effects: slope=-0.257, $t(177)=-0.853$, $p=0.394$).

To investigate whether there were any 'carryover' effects once ACS was turned off, a subset of sessions where pre-ACS and post-ACS sham blocks were completed within the same day were analyzed, revealing no significant carry-over effect of ACS. See, e.g., FIGS. 6A-6B.

ACS Entrains Neural Activity at a Preferred Phase

Figure 7C:
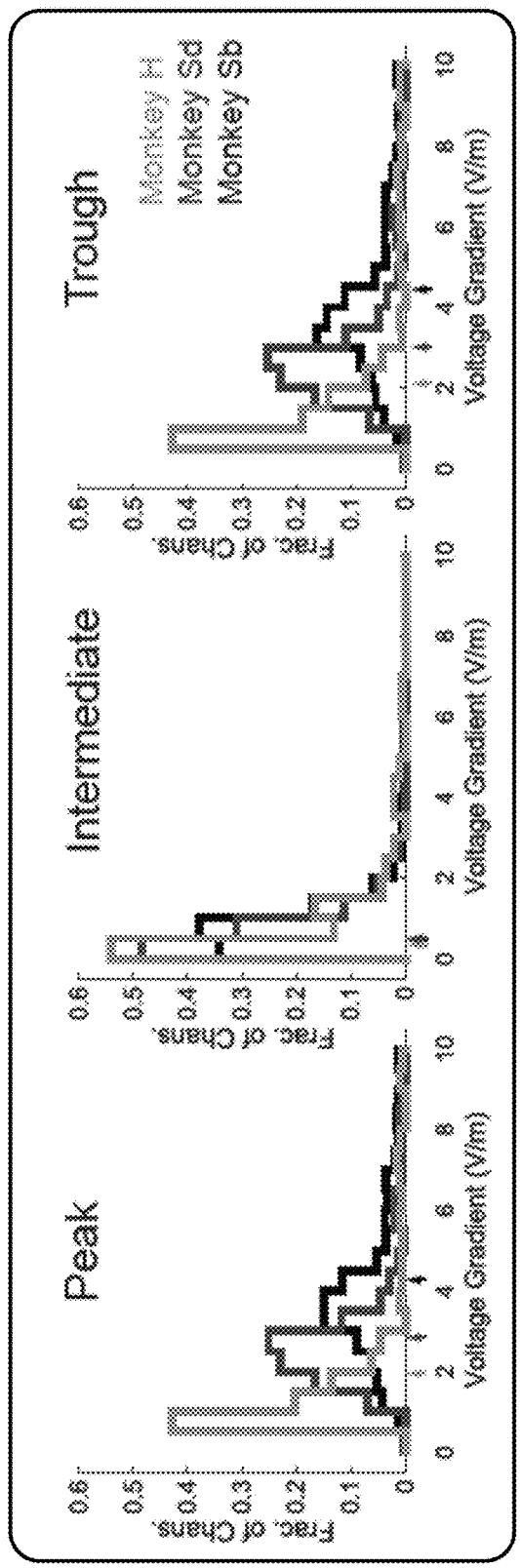
FIG. 7C shows the distribution of voltage gradients over channels and sessions for the peak (left), intermediate point (middle), and trough (right) of the ACS waveform. Arrows on x-axis indicate subject means.
Figure 7D:
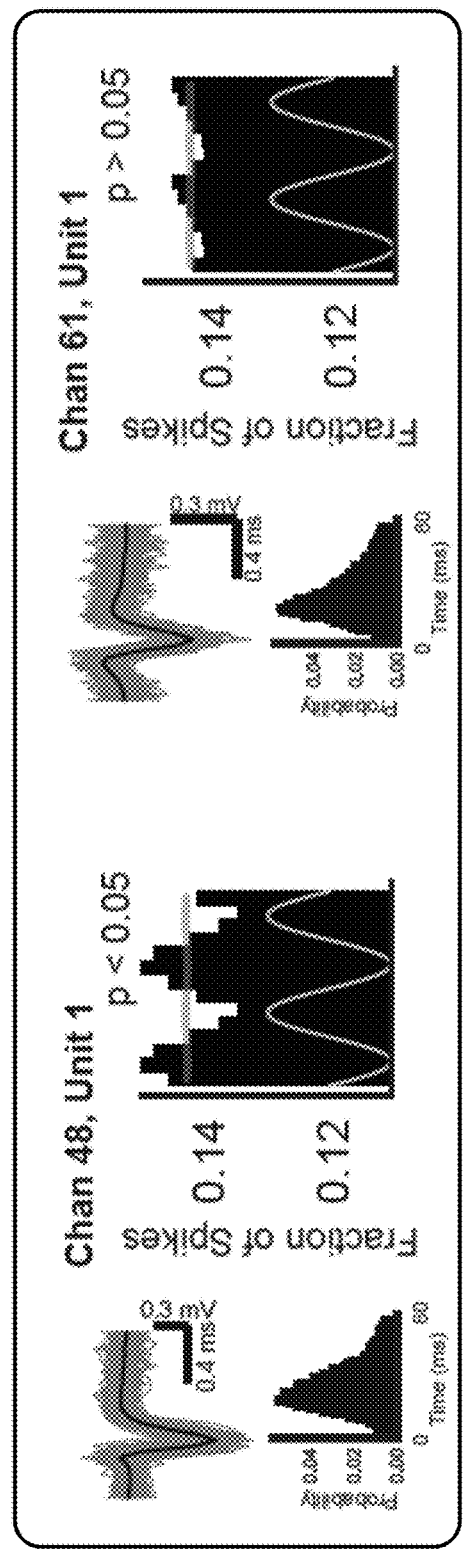
FIG. 7D shows example units recorded from Monkey H during ACS. Left (chan 48) is significantly entrained Right (chan 61) is not significantly entrained but shows slight phase preference. Example waveforms (gray), average waveforms (black), and ISIs (black histograms).
Figure 7E:
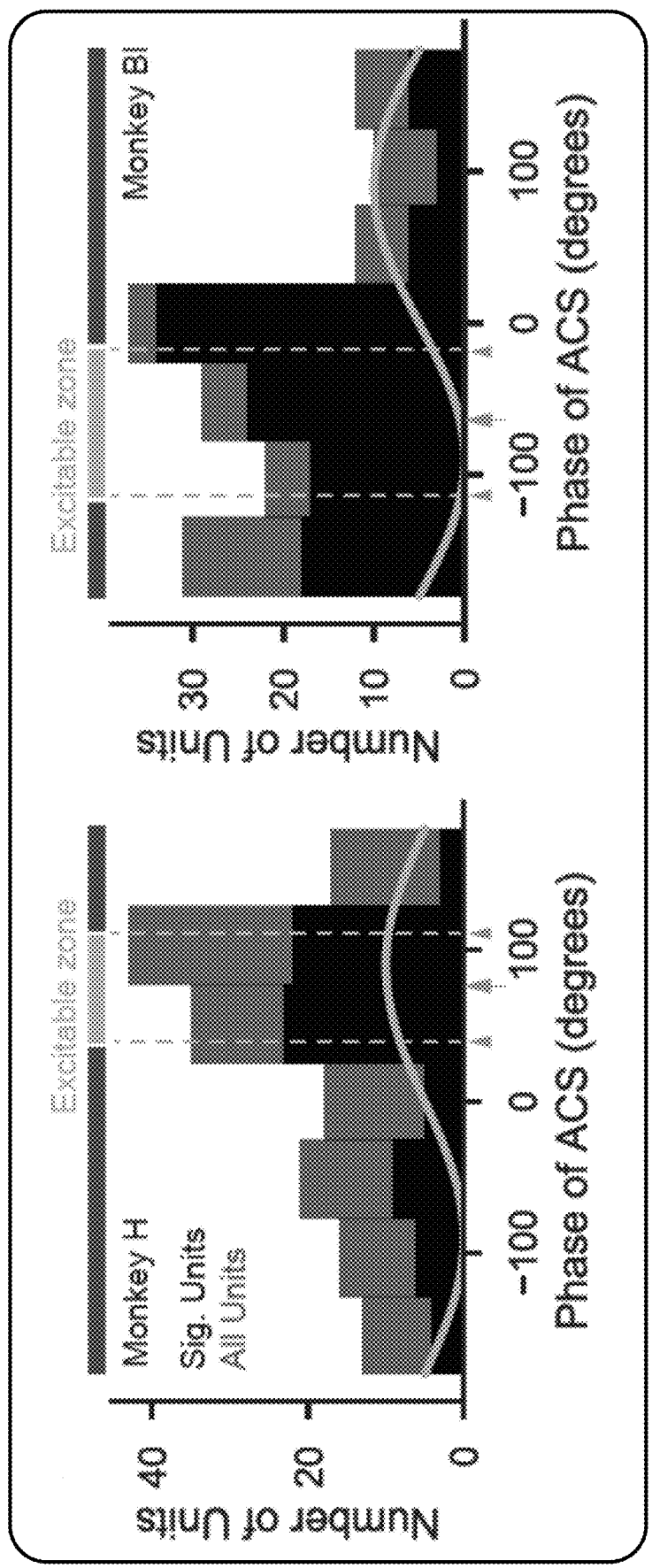
FIG. 7E illustrates the distribution of preferred phases over all units (gray bars) and significantly entrained units (black bars) recorded during ACS for Monkey H (left) and Monkey B1 (right). Distributions are significantly non-uniform (Rayleigh test, Monkey H: all units, N=163, z=11.38, p=9.68e-6, only significantly entrained units, N=72, z=12.70, p=1.82e-6, Monkey B1: all units; N=153, z=6.64, p=0.00124, significantly entrained units, N=108, z=13.33, p=1.11e-6). The designated "excitable zone" (light green bar) is illustrated above distributions.

FIGS. 7A-7E shows low-frequency ACS driving phases of neural excitability. For example, the influence of low-frequency ACS on PLC units is shown in FIG. 7B. FIG. 7B shows mean voltages, negative voltage gradient directions, and voltage gradient magnitudes for an example session from Monkey Sd. Negative voltage gradient directions (center) indicate estimates of current flow direction (other animals' voltage gradient directions were comparable). The distribution of the electric field (voltage gradient magnitude) recorded in PLC during application of ACS (n=3, see FIG. 15 (table 1)) showed that mean field values ranged from −2-4 mV/mm (FIG. 7C) and was consistently higher for animals who received higher amplitude ACS (FIG. 15, table 1). These field strengths are efficacious for biasing neural activity. Using spiking data from the full 10-15 min session recordings, entrainment to ACS was estimated. Two animals had sufficient unit recording quality to perform this analysis (FIG. 7D). Overall, 180 of the 316 units recorded from two animals (3 sessions/animal) were significantly entrained (57%). If units were restricted to putative single units, only 8 of 35 units were significantly entrained (23%).

A clear ACS phase preference across the population of all PLC units in each animal (FIG. 7E, gray bars) that was consistent even if only significantly entrained units were considered (FIG. 7E black bars) was also observed. Distributions were significantly non-uniform (Rayleigh test, Monkey H: all units, N=163, z=11.38, p=9.68e-6, sig. entrained units, N=72, z=12.70, p=1.82e-6, Monkey B1: all units; N=153, z=6.64, p=0.00124, sig. entrained units, N=108, z=13.33, p=1.11e-6). There was no significant difference between the distribution of all units and of significantly entrained units (Kuiper test, circular analog of KS test: Monkey H, test statistic=2026, p=1.0, Monkey B1: test statistic=2106, p=1.0). Interestingly, units from Monkey H preferred the peak whereas units from Monkey B1 preferred the trough. The magnitude of the voltage gradient at the peak and trough were comparable but with opposite current flow direction (FIGS. 7B-7C). Geometric orientation of units to the electric field, current amplitude, and the directional sensitivity of the network may all have influenced the preferred current direction. An animal-specific range of phases (circular mean+/−1.5*95% circular confidence interval) was defined that captured most units' preferred phase. This window of animal-specific ACS preferred phases is referred to herein as the neural "excitable zone" (EZ, light green bar, FIG. 7E).

Dexterity Improves when Trials are Aligned to EZ

Figures 8A, 8B, 8C:
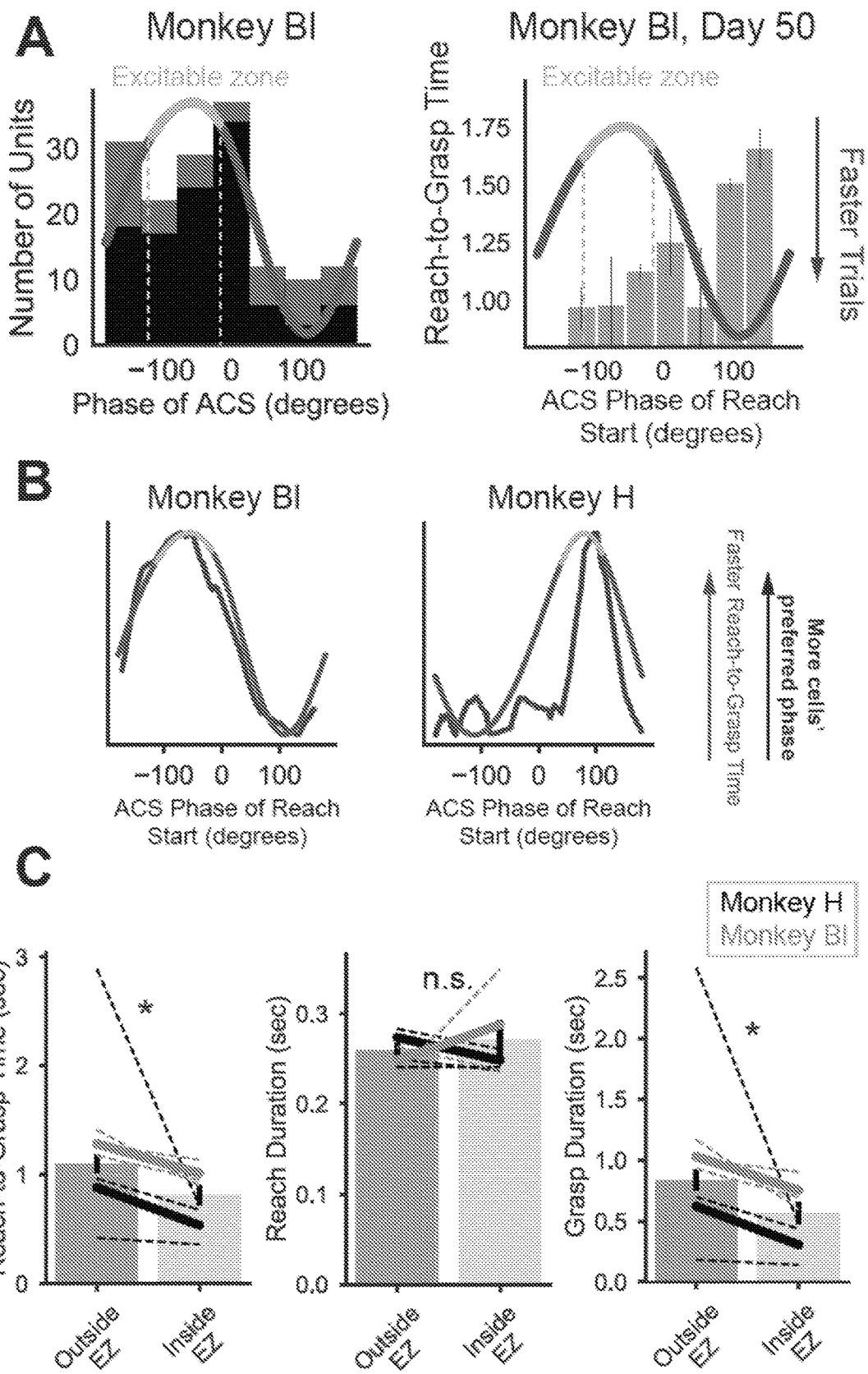
FIG. 8A (left) shows a circular histogram fit to distribution of preferred phases.
FIG. 8B shows visualization of phase-dependency of grasp duration (purple, note inversion so faster R2G times higher on y-axis) and circular histogram fit to phase preferences (green, same as FIG. 8A).
FIG. 8C shows a mean outside excitable zone (EZ) trials are significantly slower for R2G time (LME with animal, session, and well-size as random effects: $t_{101}=-2.15$, $p=0.0315$), not significantly different for reach duration ($t_{101}=0.6465$, $p=0.518$), and significantly slower for grasp duration ($t_{101}=-2.086$, $p=0.037$). Bars indicate mean (sem) over trials. Black (Monkey H) and gray (Monkey B1) dashed lines indicate average session trends. Solid lines indicate average trends pooled over sessions.

FIGS. 8A-8C illustrate that behavior starting in the excitable zone (EZ) is faster. The EZ, defined from PLC units' preferred phase, was important for function. Differences in motor behavior were predicted based on EZ alignment. A circular histogram was fit to the distribution of preferred phases, as shown in FIG. 8A (left) and binned R2G time for a representative session from Monkey B1 by ACS phase at reach start (FIG. 8A, right). A correspondence between preferred phase and faster behavior for trials starting at preferred phases was observed.

For visualization, ACS phase at reach start versus R2G time (FIG. 8B, purple) was smoothed using a non-parametric moving average. The curves were inverted with faster R2G times higher on the y-axis. To quantify ACS-phase effect on behavior, all trials were grouped as either "inside EZ" or "outside EZ" based on the phase of reach start. Trials were significantly faster inside EZ than outside EZ (see, e.g., FIG. 8C: LME with animal, session, and well-size as random effects, t101=−2.15, p=0.0315) and grasp duration (t101=−2.086, p=0.037) with no significant difference for reach duration (t101=0.6465, p=0.518). Thus, the EZ reflected periods of network-wide change that significantly influenced behavior.

ACS Drives Phase-Dependent Increases in Ensemble Co-Firing

The phase of the ACS applied may also influence the effect (e.g., the effect in a directed movement, such as a task-related activity). Specifically, units that fired together in the task-related sequence may exhibit stronger co-firing due to the common influence from the low-frequency ACS. To examine this, activity was split into "ensembles" consisting of distinct subsets of units that significantly modulated above baseline during i) reaching but not grasping ("reach"), ii) reaching and grasping ("reach-grasp"), or iii) grasping but not reaching ("grasp"). The reach and reach-grasp ensembles were analyzed from −1.0-0.25 s and −0.25-0.25 s aligned to reach start respectively. The grasp ensemble was analyzed from −0.25-0.45 s (Monkey H) or −0.25-0.85 s (Monkey B1), reflecting animal-specific average grasp duration.

Figure 9B:
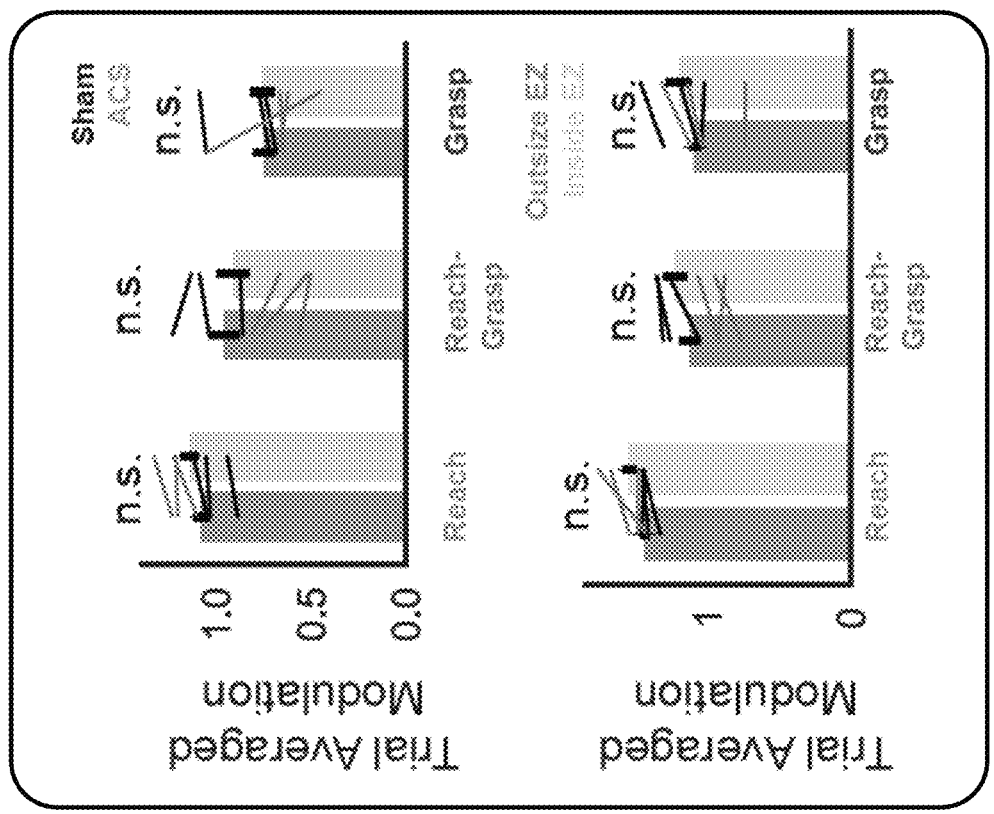
FIG. 9B shows no significant differences in trial-averaged unit modulation for sham vs. ACS (LME, animal and session as random effects: reach ensemble: t230=1.10, p=0.27, reach-grasp ensemble: t76=-0.429, p=0.668, grasp ensemble: t50=0.0399, p=0.968). No significant differences in trial-averaged unit modulation for ACS trials with reach start outside EZ vs. inside EZ (reach ensemble: t230=1.88, p=0.059, reach-grasp ensemble: t76=0.944, p=0.345, grasp ensemble: t50=1.140, p=0.254). Bars indicate mean (sem) across all units. Black (gray) lines correspond to mean trends for each session pair for Monkey H (B1).
Figure 9A:
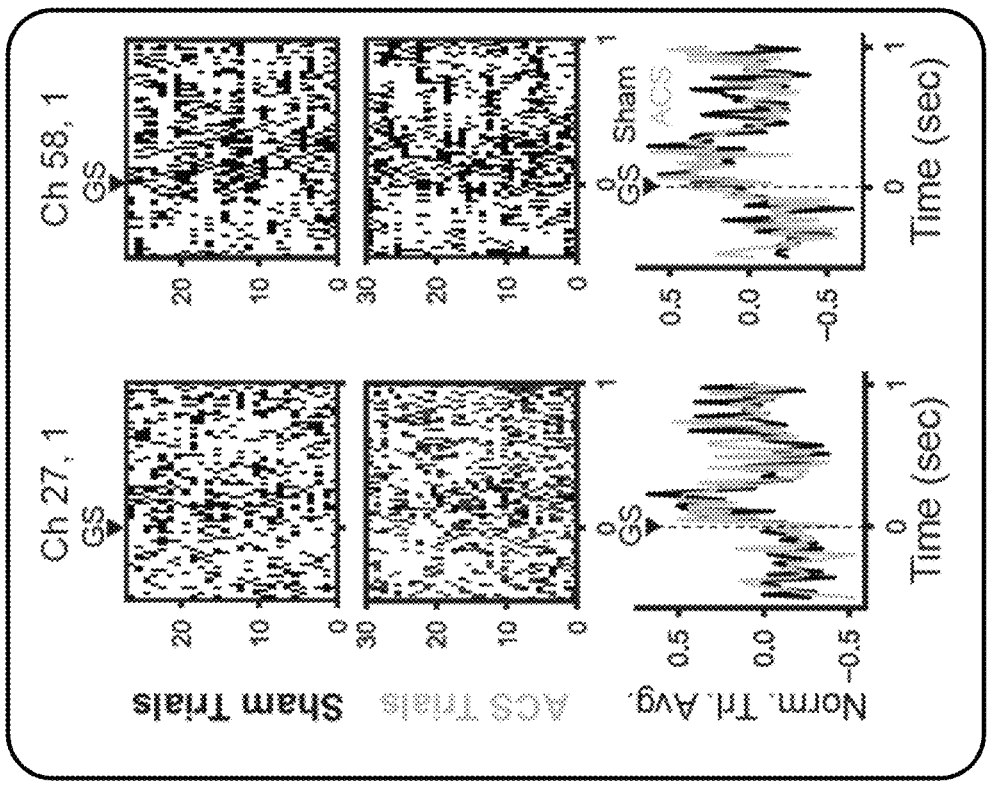
FIG. 9A (top) shows an example grasp start (GS) aligned rasters from grasp ensemble units in Monkey H on day 23 (sham) and 24 (ACS).

Modulation of trial-averaged unit activity was examined, as shown in FIG. 9A, showing raster plots and normalized mean traces for example units from the grasp ensemble. FIGS. 9A-9G illustrate phase-dependent increases in task ensemble co-firing with ACS There were no significant changes in unit modulation (FIG. 9B, LME with animal and session as random effects: reach ensemble: $t230=1.10$, $p=0.27$, reach-grasp ensemble: $t76=−0.429$, $p=0.668$, grasp ensemble: $t50=0.0399$, $p=0.968$). There was also no significant difference for ACS trials with reach start outside EZ vs. inside EZ (LME with animal and session as random effects: reach ensemble: $t230=1.88$, $p=0.059$, reach-grasp ensemble: $t76=0.944$, $p=0.345$, grasp ensemble: $t50=1.140$, $p=0.254$). Pairwise correlations between pairs of units within an ensemble were analyzed, and no changes with ACS or inside vs. outside EZ trials were found. Thus, the effects of stimulation were not detectable at the level of single units or pairwise interactions. There were substantial changes in the off-diagonal values of the pairwise correlation matrices across conditions. Thus, ACS may modify a subset of pairwise interactions that is detectable at the level of ensemble correlations.

Figure 9C:
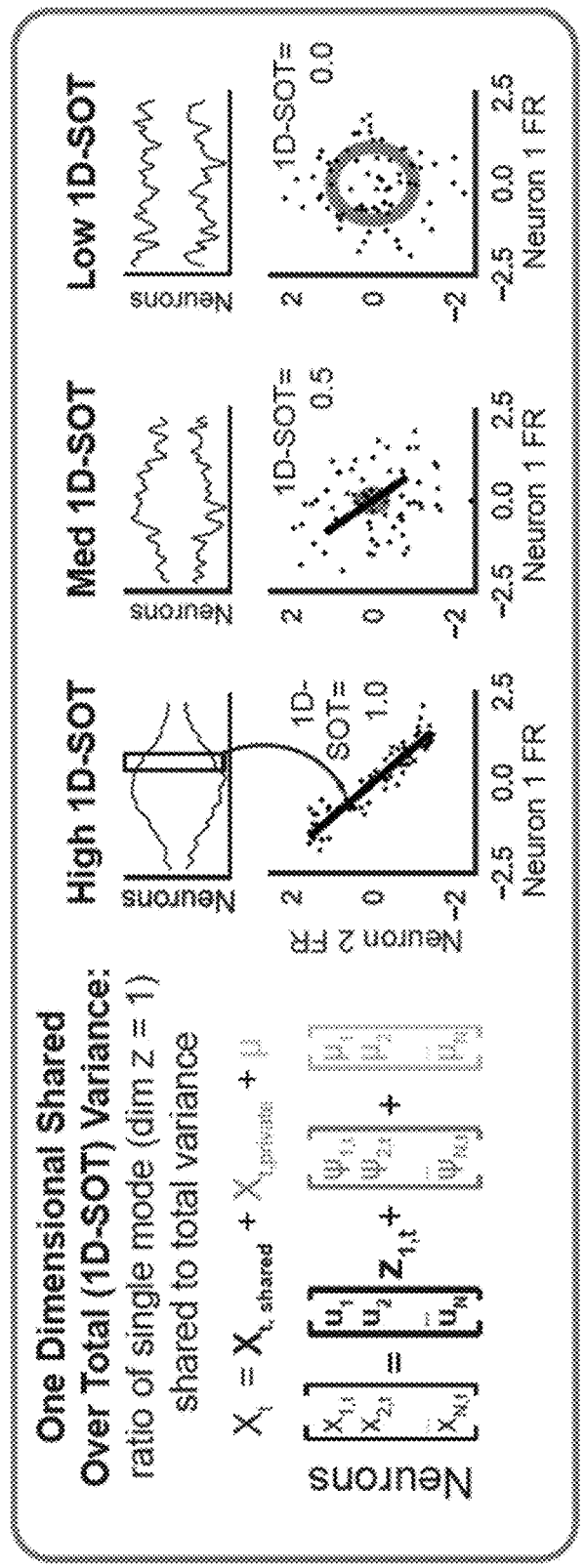
FIG. 9C illustrates 1D-shared over total (1D-SOT) metric to assess co-firing. One-dimensional Factor Analysis model fit to ensemble data (as in bottom left equations), and 1D-SOT computed using model parameters. 2-neuron examples of high, medium, and low 1D-SOT (right).
Figure 9D:
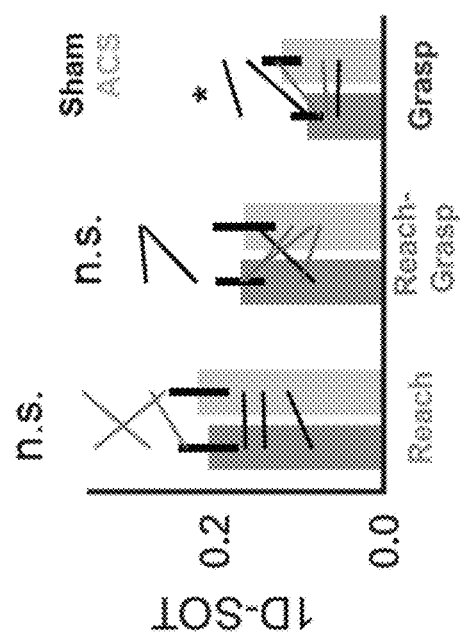
FIG. 9D reach and reach-grasp ensemble 1D-SOT is not significantly different for sham vs. ACS (LME, animal and session as random effects: reach: t10=0.524, p=0.600, reach-grasp: t10=-0.1945, p=0.846), but grasp ensemble 1D-SOT is significantly higher for ACS vs. sham (t8=2.112, p=0.0347). Bars indicate means (sem) over all animals and sessions. Black (Monkey H) and gray (Monkey B1) lines correspond to 1D-SOT values for each session pair.

Ensemble co-firing was qualified using a metric termed "one dimensional shared over total variance" (1D-SOT, FIG. 9C), a modified version of the SOT metric. Specifically, the 1D-SOT was derived by fitting a Factor Analysis (FA) model with a single shared dimension to ensemble activity. FA models population variance as a sum of low-dimensional sources of shared variance (co-firing), and high-dimensional sources of variance specific to each unit. FA was used instead of other dimensionality reduction methods to specifically model co-firing. A single shared dimension was used since the model was fit on ensembles, thereby already restricting to units that positively modulate in the analyzed time windows. Thus, ensemble shared variance was expected to be one-dimensional. Further, the inventors assessed whether ACS would affect the dominant shared variance dimension for each ensemble, making 1D-SOT comparisons appropriate. A high 1D-SOT value indicates high ensemble co-firing whereas a low 1D-SOT value indicates that ensemble units largely fire independently (FIG. 9C).

Figure 9E:
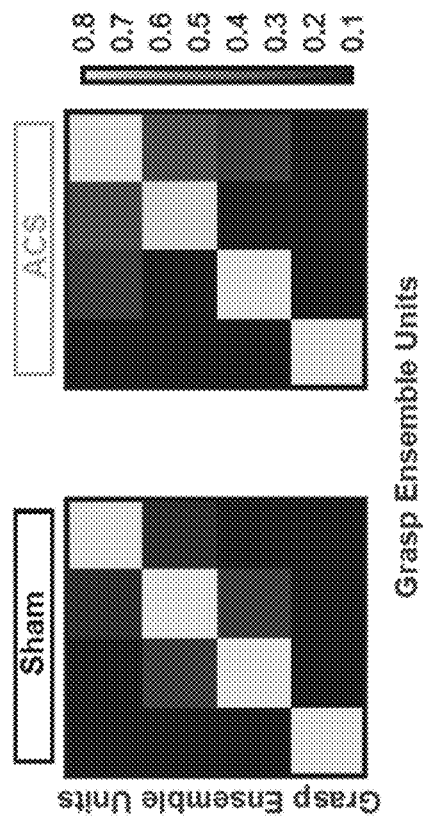
FIG. 9E shows covariance matrices for grasp ensemble units for Monkey H days 23 (sham) and 24 (ACS).
Figure 9F:
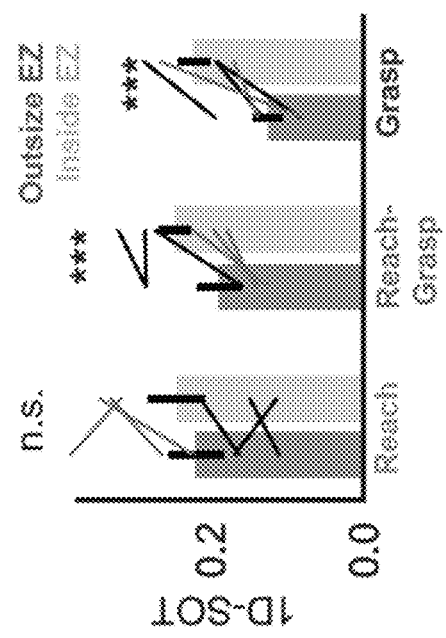
FIG. 9F shows 1D-SOT is not significantly different for ACS outside EZ vs. inside EZ trials in reach ensemble (LME, animal and session as random effects: t10=0.879, p=0.379), but is significantly higher for trials with reach start inside EZ vs. outside EZ for the reach-grasp (t10=3.359, p=0.000782) and grasp ensembles (t8=3.7076, p=0.00021). Bars indicate means (sem) over animals and sessions. Black (Monkey H) and gray (Monkey B1) lines correspond to 1D-SOT values for each condition pair.
Figure 9G:
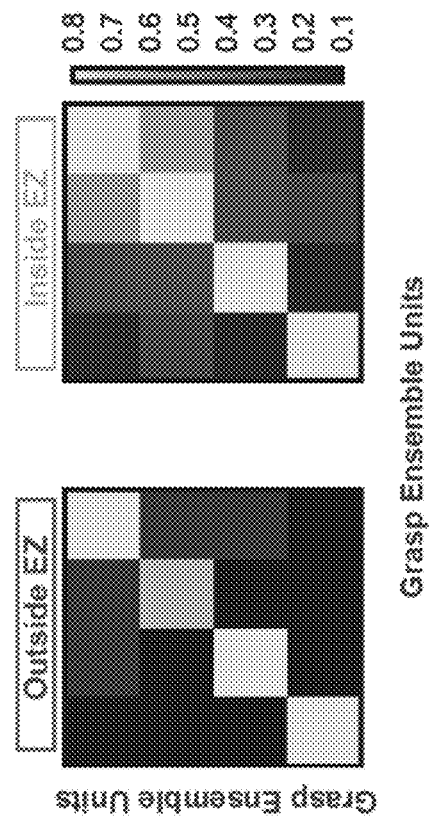
FIG. 9G shows covariance matrices for grasp ensemble units from Monkey H days 24 (ACS) for outside EZ and inside EZ trials.
Figure 10B:
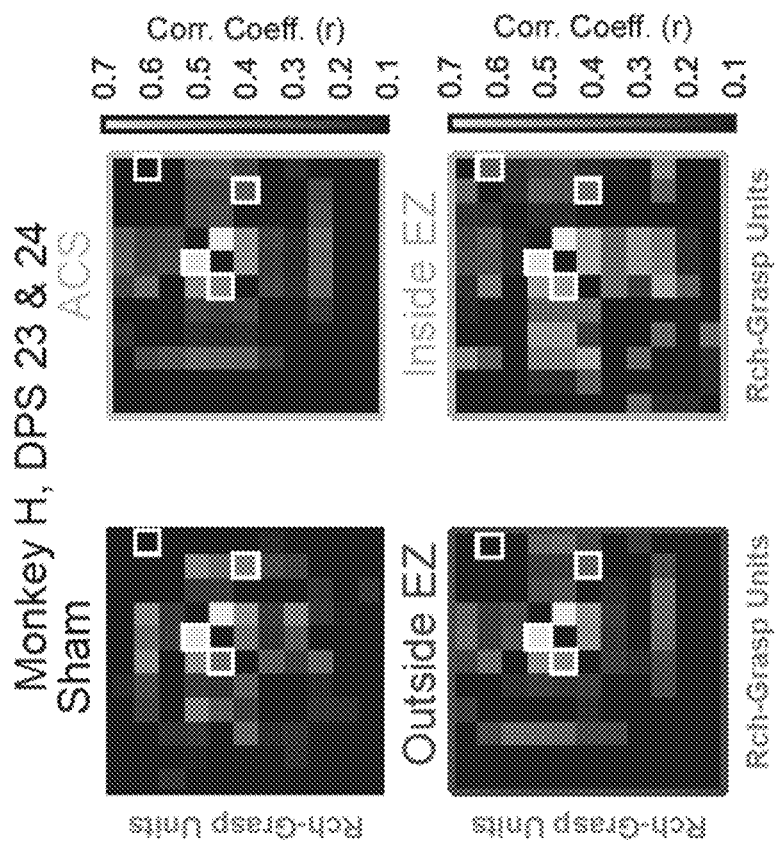
FIG. 10B illustrates an example from Monkey H, day post stroke 23 (sham) and 24 (ACS) of pairwise correlations computed from sham trials (top left), ACS trials (top right). ACS trials are broken into outside EZ trials (bottom left) and inside EZ trials (bottom right). White boxes highlight examples shown in FIG. 10C. Diagonals are set to zero.
Figure 10A:
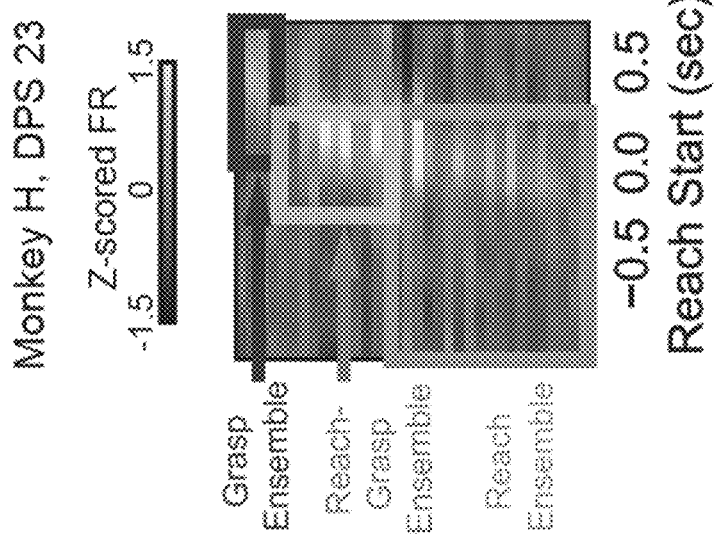
FIG. 10A shows an example of trial-averaged activity from Monkey H on day 23 post-stroke. Units that are significantly modulated above baseline during reaching but not grasping, reach and grasping, or grasping but not reaching are in the "reach ensemble", "reach-grasp" ensemble, or "grasp ensemble" respectively. Time windows of analysis for the reach (-1.0, 0.25 sec aligned to reach start), reach-grasp (-0.25, 0.25 sec aligned to reach start), and grasp (-0.25, 0.45 sec aligned to grasp start) ensembles are also illustrated.
Figure 10C:
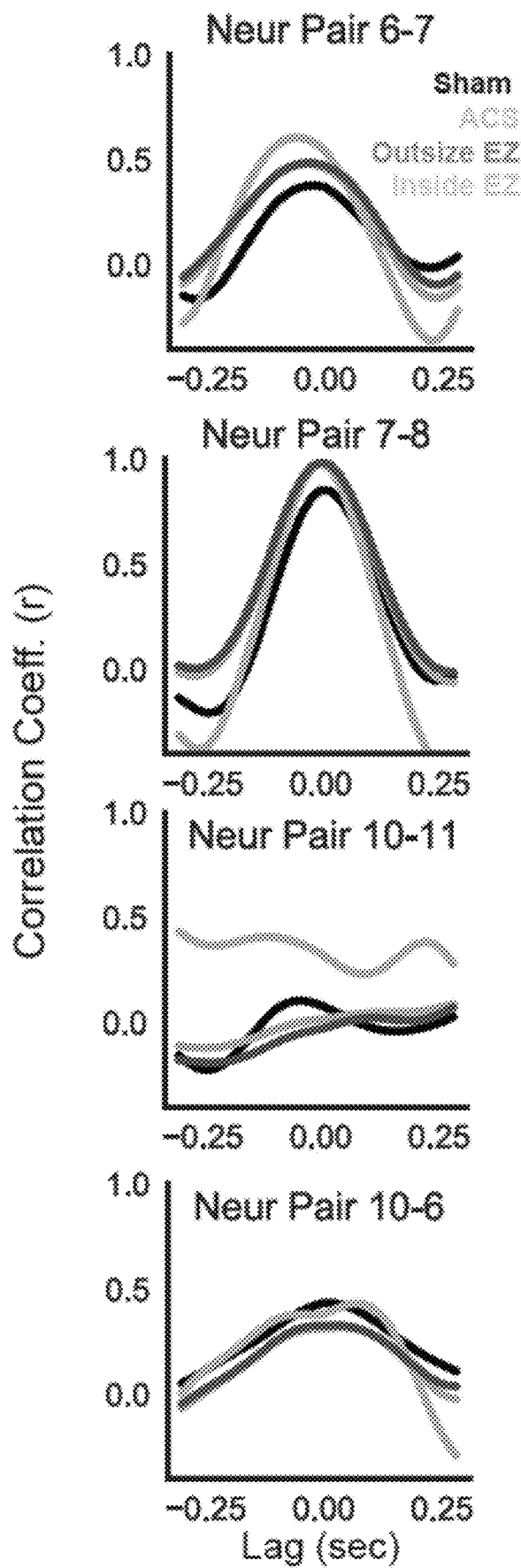
FIG. 10C shows a cross correlograms for pairs of units (correspond to the white boxes in (B)). For some pairs, correlations increase for ACS, and increase even more of "inside EZ" (e.g. top left, right). For other pairs, there is little change (bottom left), or only a change for "inside EZ" trials (bottom right).

Sham and ACS conditions were compared, and it was found that 1D-SOT was significantly higher in the grasp ensemble with ACS (FIG. 9D, LME with animal and session as random effects, $t8=2.112$, $p=0.0347$) and not significantly different for the reach ($t10=0.524$, $p=0.600$) or reach-grasp ensemble ($t10=−0.1945$, $p=0.846$). Increased off-diagonal components in grasp ensemble covariance matrices illustrate increased 1D-SOT (FIG. 9E). Inside EZ 1D-SOT was significantly higher than outside EZ 1D-SOT for the reach-grasp (LME with animal and session as random effects: $t10=3.359$, $p=0.000782$) and grasp ($t8=3.7076$, $p=0.00021$) ensembles but not different for the reach ensemble ($t10=0.879$, $p=0.379$). The higher inside EZ versus outside EZ off diagonal components illustrate the higher 1D-SOT (FIG. 9G). Template match (e.g., FIG. 1F), dimensionality, and temporal predictability (FIGS. 4A-4J) were also analyzed, and ACS did not significantly affect these metrics. See, e.g., FIGS. 10A-10G, showing changes in neural firing properties with ACS. Thus, changes with ACS were not detectable in modulation of individual units (FIG. 9B) or pairwise interactions (FIGS. 10B-10D) but were clear at the ensemble correlation level (FIGS. 9D-9G).

Given the increases in grasp-ensemble 1D-SOT with ACS, 1D-SOT may also increase over the course of behavioral recovery. Changes in neural activity from early to recovered sessions exhibited increases in dimensionality (see, e.g., FIG. 4C). Since higher dimensional signals directly reduce the amount of shared variance that can be absorbed by a single dimension, this change may limit a comparison of 1D-SOT from early to recovered sessions. The same stably recorded units observed in early sessions were not always observed in later sessions, preventing a comparison of early session units to a subselection of the same units in late sessions. A comparison of intermediate days to fully recovered days was made, since the neural population did not exhibit significant changes in dimensionality (LME with animal as random effect $t10=−0.1747$, $p=0.8613$). There was a significant increase in 1D-SOT computed from the full population of units within the R2G time period (−0.25 to 0.25 seconds aligned to grasp start, LME with animal as random effect, $t8=2.29$, $p=0.0219$). Thus, increases in 1D-SOT could account for the immediate effects of stimulation and the improvements in behavior over late stage recovery.

Overall, the preferred phases of ACS corresponded to increased neural excitability (EZ) which increased grasp ensemble co-firing especially when behavior started within the EZ. This increased co-firing may reflect neural patterns that resemble a more "recovered state" and may account for improved dexterity.

These results are consistent with a neural network model of stroke, ACS, and sequence propagation. Specifically, these results suggest that changes in task-related ensemble firing results in improvements in dexterity. A model of an impaired PLC was used to explore the relationship between ACS, co-firing, and propagation of neural sequences. To model an impaired PLC, a synfire network that was designed to produce sequential activity was modified, emulating the R2G-related PLC patterns observed in the recovered state and in intact animals from other studies.

FIGS. 11A-11I illustrate the use of a neural network model of PLC links ACS, ensemble co-firing, and neural sequence propagation.

To model impairment, parts of the network had reduced internal connectivity (FIG. 11A). Premotor PLC re-wiring is critical for recovery and reduced internal network connectivity reflected incomplete re-wiring. Specifically, following M1 lesions, hand movement representation within premotor (PLC) motor maps have been shown to expand in area. Changes in premotor maps are correlated with behavioral recovery. Premotor PLC also has anatomical projections to subcortical targets that can drive both proximal and distal movements enabling its role in recovery. Furthermore, the sequential neural activity that emerged with recovery was interpreted (FIG. 1A-1H, FIG. 4A-4J) to reflect a PLC network that developed internal connections to produce neural patterns for successful R2G actions. Described herein are modeling changes within premotor PLC as they correlate with recovery and ACS-related improvements.

Specifically, the PLC model was composed of a fully connected "reach" subnetwork (43 pools, 100% inter-pool connectivity) connected to an incompletely formed "grasp" subnetwork (43 pools, 85% inter-pool connectivity, FIG. 11A) with pools comprised of 100 integrate-and-fire neurons. The model had impaired neural sequence production and activity patterns that replicated our experimentally observed reductions in template matching, dimensionality, and temporal predictability found early after stroke (FIG. 1A-1H, FIG. 4A-4J). Importantly, the timing between the start of the "reach" subnetwork and the start of the "grasp" subnetwork was ~258 ms, matched to experimental data (Monkey H: 260 ms, Monkey B1: 253 ms). R2G neural patterns in the network were initiated by an "input" spike train that consisted of N spikes drawn from a Gaussian distribution with mean ($\mu$) and standard deviation ($\sigma$) (FIG. 11C). Input properties influenced activity propagation. FIG. 11B left illustrates input parameters that did not fully propagate. An increase in N (center) or a decrease in $\sigma$ (right) allowed full propagation.

Activity propagation was considered as a proxy for quality of R2G behavior where poorly propagating activity corresponded to poor movements. Input parameters where activity was successfully initiated but exhibited incomplete propagation to model intact reaching and impaired grasping were selected, as when testing ACS. "Sequence propagation" was defined as the correlation between simulated activity and an ideal, fully propagated template sequence (FIG. 11D). White lines illustrate input parameters ($\sigma$,N) where sequence propagation was incomplete but initiated.

Figure 11F:
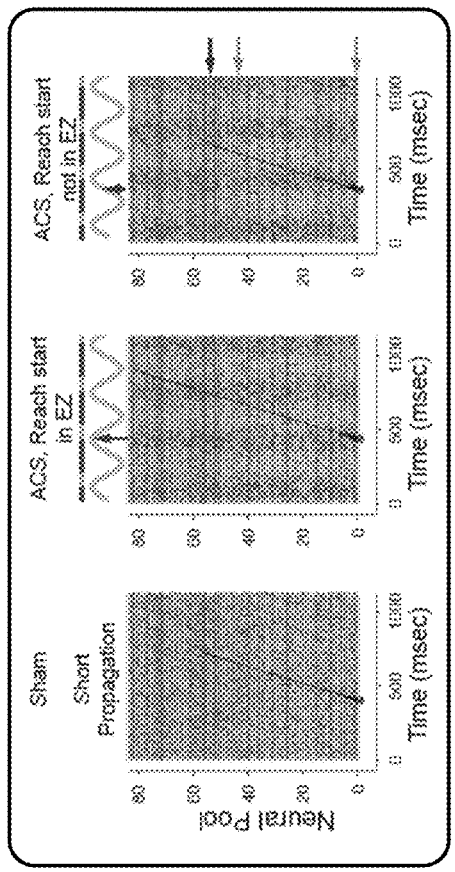
FIG. 11F shows 1D-SOT significantly changes for sham vs. ACS and Outside vs. Inside EZ for all ensembles. (LME, input parameter as random effect: Top, sham vs. ACS: pool 1: $t_{36}$=−10.03, p<1.08e-23, pool 43: $t_{36}$=9.38, p<6.45 e-21, pool 53: $t_{36}$=8.61, p<7.05e-18. Bottom outside EZ vs. inside EZ, pool 1: t-=24.77, p<1.87e-135, pool 43: $t_{36}$=13.23, p<5.7e-40, pool 53: $t_{36}$=11.51, p<1.18e-30).
Figure 11G:
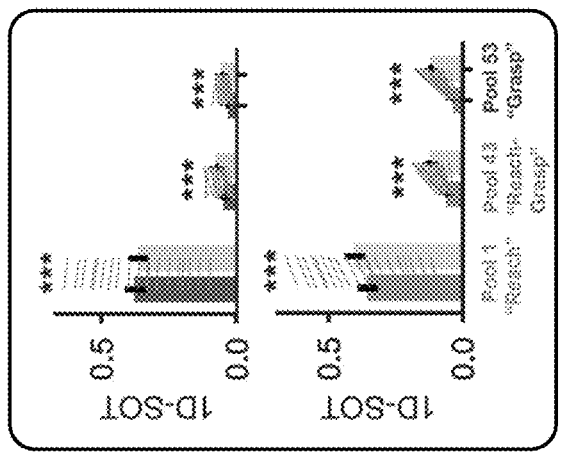
FIG. 11G is an example of a short propagation sequence (left). Input aligned to EZ can improve (center), or worsen propagation (right).

ACS was applied to the model and found entrained network activity and phase-dependent improvements in propagation. ACS was modeled as a sinusoidal current injected directly into each neuron. Units exhibited entrainment to the ongoing sine wave (FIG. 11E). As in the experimental data, the EZ was computed from the distribution of preferred phase of all units (FIG. 11E). When simulating activity with ongoing ACS, if the mean of the input spike train ($\mu$) was inside the EZ, propagation improved (FIG. 11G center) compared to activity simulations without ACS (FIG. 11G, left). When the same input spike train was outside the EZ, propagation worsened (FIG. 11G, right). Generally, when input spike trains were centered on the EZ, sequence propagation improved. Changes in propagation (FIG. 11H) depended on input parameters (x-axis) and alignment to ACS phase (y-axis). Input spike trains starting inside the EZ improved propagation (red) compared to the no-ACS (sham) condition.

As in the experimental data, simulated patterns were analyzed for changes in 1D-SOT. The 1st, 43rd, and 53rd pools were analyzed to assess "reach", "reach-grasp", and "grasp" ensemble 1D-SOT, as in FIG. 9 (pools marked with horizontal arrows to the right of FIG. 11G, right). 1D-SOT significantly increased for sham vs. ACS and Outside vs. Inside EZ for all ensembles except sham vs. ACS for the reach ensemble (FIG. 11F LME with input parameter as random effect: Top, sham vs. ACS: pool 1: $t36=-10.03$, $p<1.08e-23$, pool 43: $t36=9.38$, $p<6.45$ e-21, pool 53: $t36=8.61$, $p<7.05e-18$. Bottom outside EZ vs. inside EZ, pool 1: $t36=24.77$, $p<1.87e-135$, pool 43: $t36=13.23$, $p<5.7e-40$, pool 53: $t36=11.51$, $p<1.18e-30$). As in FIG. 5D-G, 1D-SOT effects are stronger for the inside vs. outside EZ comparisons compared to the sham vs. ACS comparisons. Effects are also strongest for the later activating reach-grasp and grasp ensembles compared to the reach ensemble.

There is a link between changes in 1D-SOT and changes in propagation. Changes in 1D-SOT observed in the "grasp" ensemble were strongly predictive of sequence propagation (FIG. 11I, linear regression, slope=1.58, r=0.89, $p<3.77e-59$, N=171). This result draws a putative link between the phase-dependent increases in 1D-SOT observed in the experimental data (FIGS. 9A-9G) and the phase-dependent improvements in behavior observed (FIG. 8A-8C). Increased grasp co-firing may reflect neural patterns with improved propagation, and therefore improved behavior.

ACS Waveform Optimization

Figure 12A:
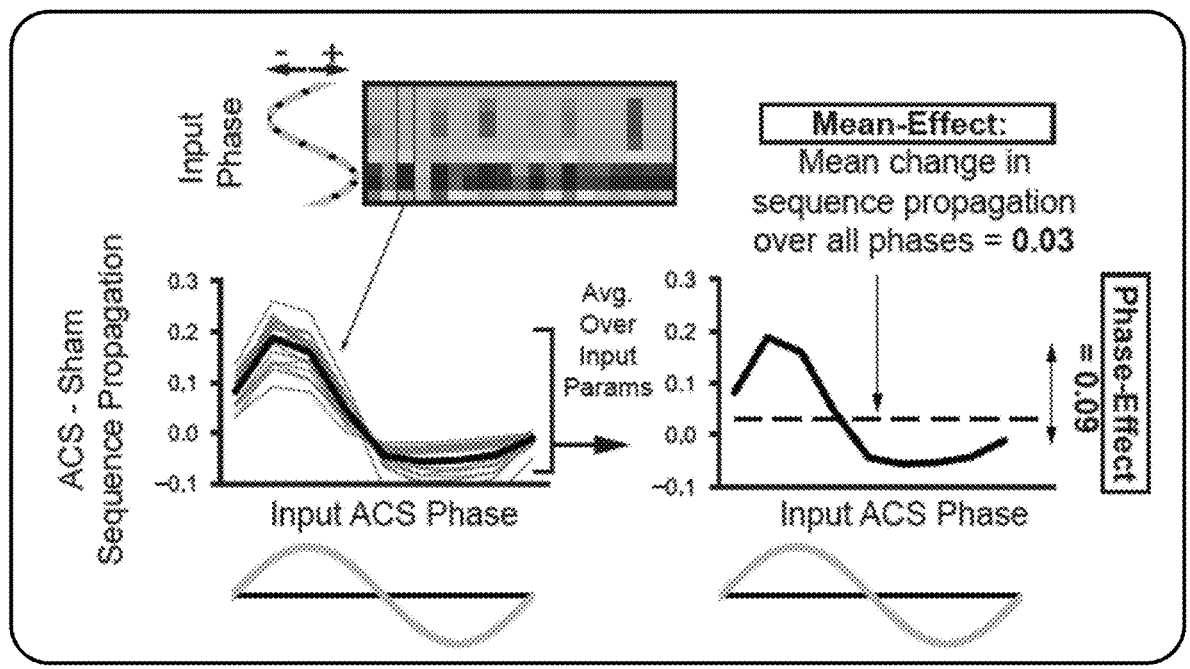
FIG. 12A shows "mean effect" and "phase-effect" quantification. Left: Gray lines are change in propagation as function of input alignment to ACS phase for each impaired R2G input parameter, Right: Black line is average over all input parameters. "Mean effect" is average of black line and "phase effect" is std. of black line.

FIGS. 12A-12I illustrate waveform optimization to enhance propagation. A charge-balanced stimulation waveform that improves propagation in a less phase-dependent manner may be used. The "mean-effect" and "phase-effect" may be tracked to compare different stimulation paradigms (FIG. 12A). Mean effect was mean improvement in sequence propagation computed over all input parameters and ACS phases. Phase effect reflected the phase dependence of improvements. Ideal stimulation may have low phase (x-axis) and high mean effects (y-axis, purple region, FIG. 12B).

Changing the amplitude of 3 Hz ACS (FIG. 12C) was examined. While increased amplitude increased the mean effect, there was increased phase-effects up to 75 nA, after which both effects reduced. Above 75 nA, amplitude was so high it started to drive neural sequences at unintended times (FIG. 12D center) or completely entrain neurons, preventing sequence production (FIG. 12D right). While entrainment is generally viewed as beneficial, these results suggest that excess entrainment can subsume intrinsic dynamics.

Changing ACS frequency (constant amplitude) was also examined. Low frequencies (blue, FIG. 12E) were efficacious, but had large phase-effects. High frequencies were ineffective at improving sequence propagation, likely due to neuron membrane time constants preventing integration of high frequency inputs. Higher frequencies may be efficacious but would require much higher amplitudes.

Figure 12B:
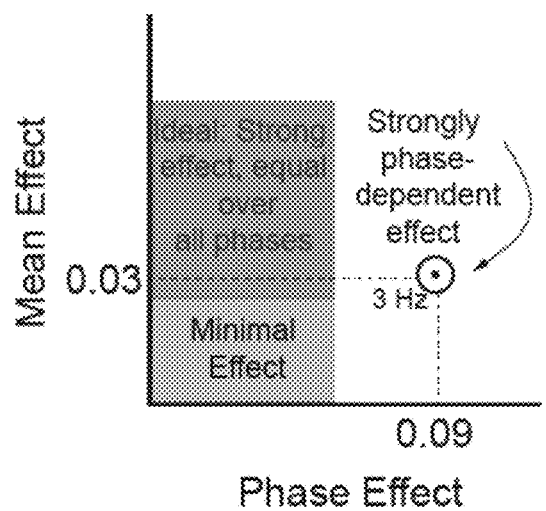
FIG. 12B shows phase-effect vs. mean-effect space: ideal stimulation has a low phase-effect and high mean-effect (purple).
Figure 12C:
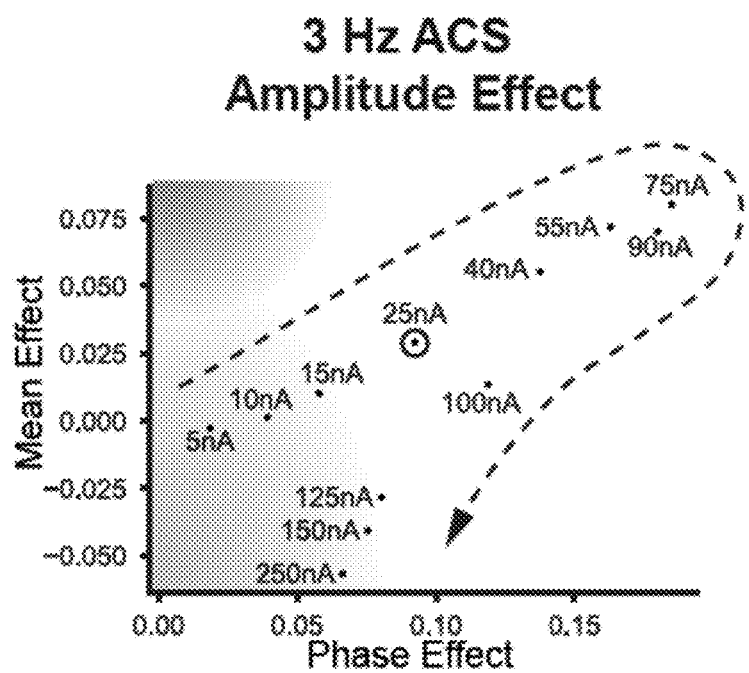
FIG. 12C illustrates phase-effect vs. mean-effect for varying amplitudes (in nanoamps) of 3 Hz ACS. Circled point indicates amplitude used in FIGS. 11A-11I.
Figure 12D:
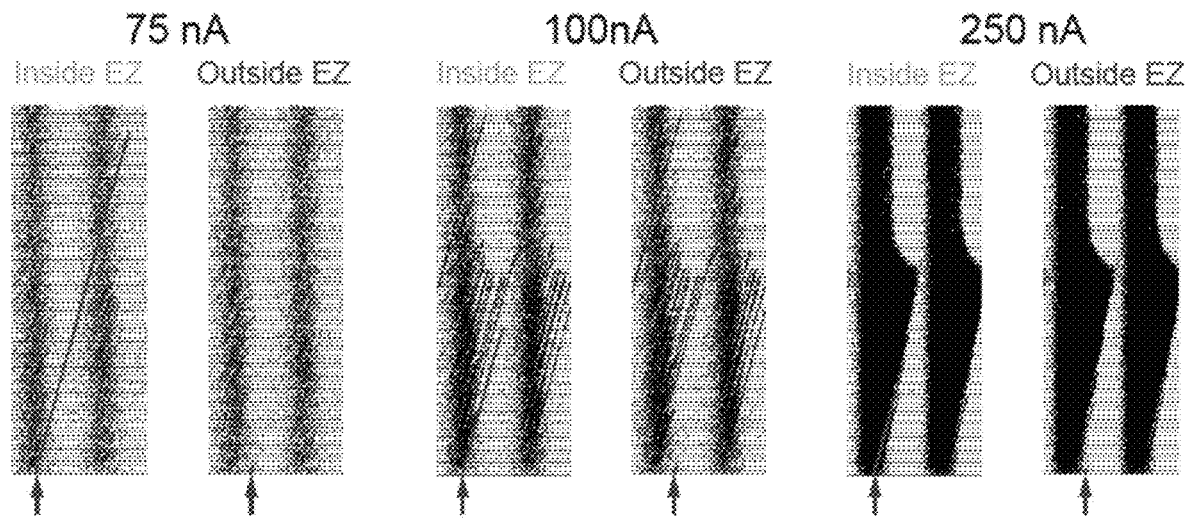
FIG. 12D shows ACS amplitude affects sequence propagation when input is delivered inside EZ (left plots in each column) and outside EZ (right plots in each column). Sequences are red for visualization.
Figure 12E:
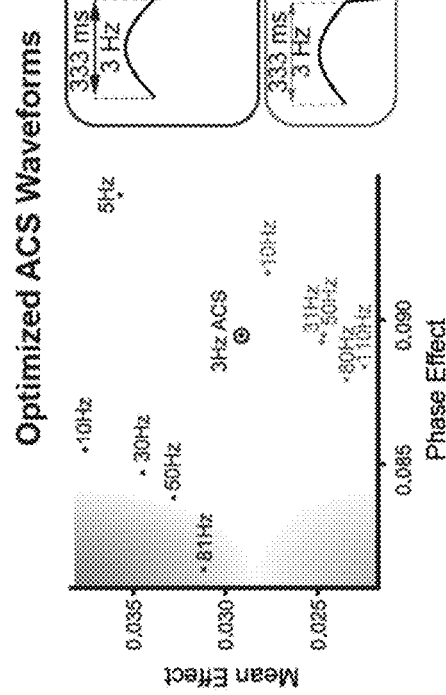
FIG. 12E illustrates phase-effect vs. mean-effect for different ACS frequencies.
Figure 12F:
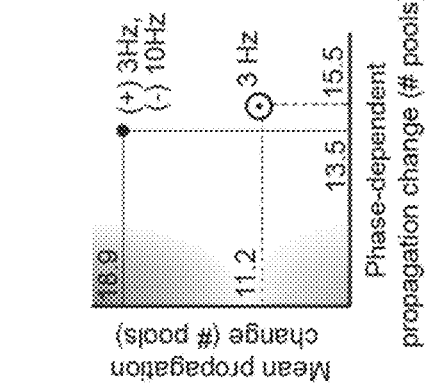
FIG. 12F illustrates phase-effect vs. mean-effect for designed waveforms. Colors denote waveform shape (maroon=single negative half-cycle, orange=multiple negative half-cycles). Frequency labels denote the frequency of the negative half-cycle.
Figure 12G:
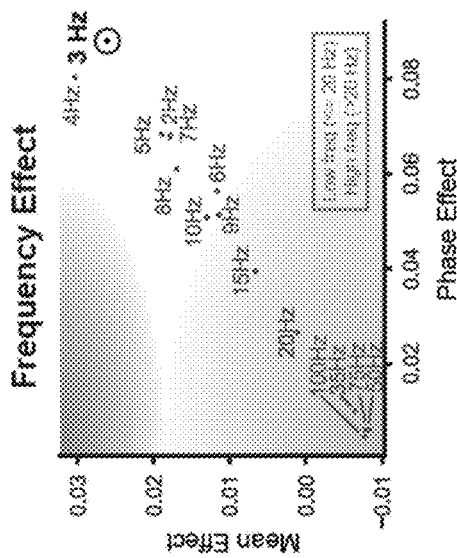
FIG. 12G shows an optimized waveform (+3 Hz, single half-cycle −10 Hz) improves sequence propagation (right) compared to 3 Hz ACS (left) for same inputs.
Figure 12H:
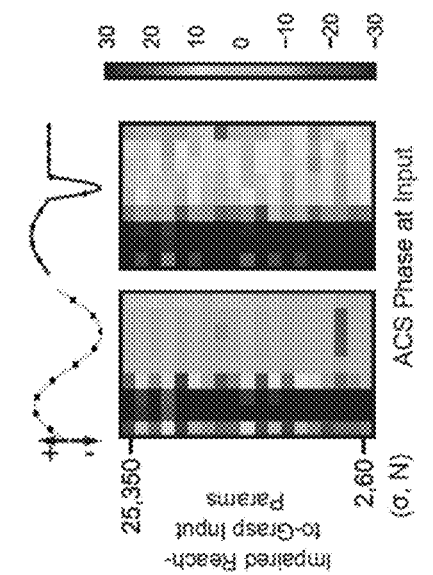
FIG. 12H is a comparison between 3 Hz ACS (left) and optimized waveform (+3 Hz, single phase −10 Hz, right) sequence propagation length. Color indicates change in propagation length (units of #pools) compared to non-ACS for a given input parameter set (y-axis) at a given phase of the waveform (x-axis). Red and blue indicate lengthening and shortening in propagation respectively.

Low frequencies may influence membrane voltages more than high frequencies, and therefore to keep the efficacious EZ of the 3 Hz waveform and reduce the detrimental phases (FIG. 12H), a new waveform was created by adjoining a positive half cycle of the 3 Hz waveform to one or many negative half-cycles of a higher frequency waveform (FIG. 12F, right). Overall, the waveform with the single negative half-cycle (maroon) improved most upon standard 3 Hz ACS by reducing the phase effect and improving mean effect (FIG. 12F left). Examples in FIG. 12G illustrate that the reduced duration of the negative half-cycle of the designed waveforms may assist with sequence propagation.

Figure 12I:
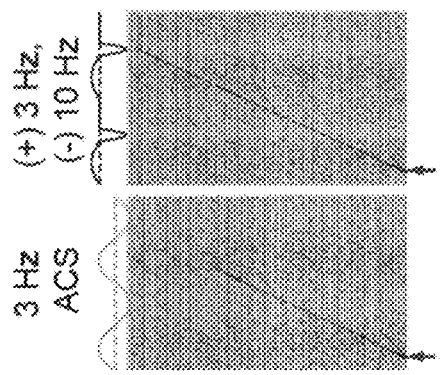
FIG. 12I shows phase-effect vs. mean-effect in units of "change in pools propagated" instead of "change in sequence propagation metric" (as in FIGS. 12B-12C and 12E-12F). For 3 Hz ACS (black), ACS extends propagation by a mean-effect (phase-effect) of 11.2 (15.5) pools. Optimized waveform (maroon) extends propagation by 18.9 (13.5) pools.
Figure 13A:
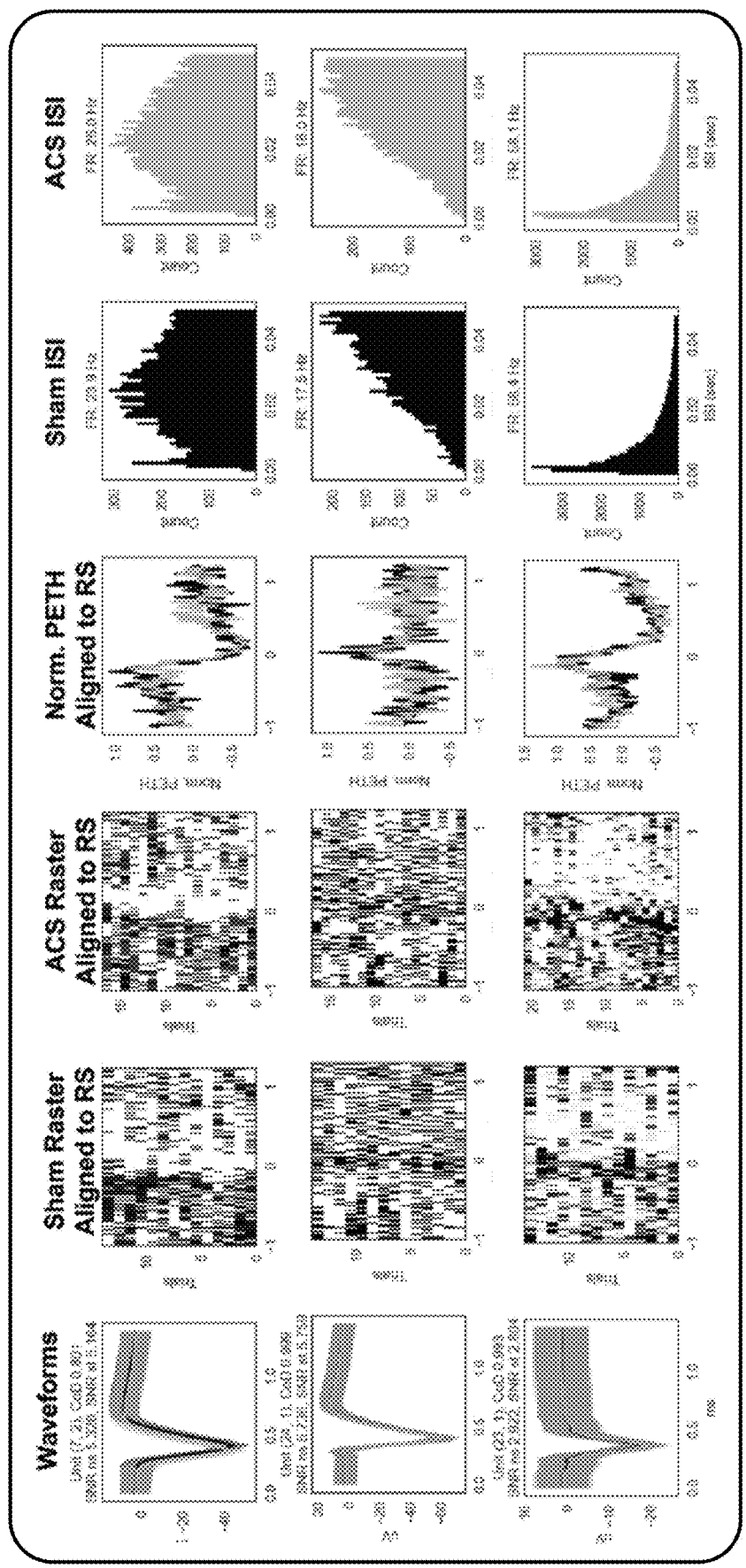
FIGS. 13A-13D show example waveforms and waveform characteristics from Monkey B1.
Figure 13B:
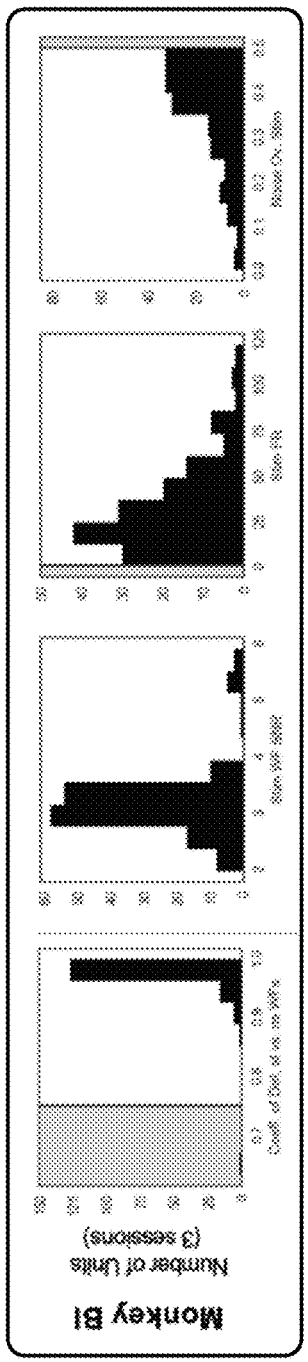
Figure 13C:
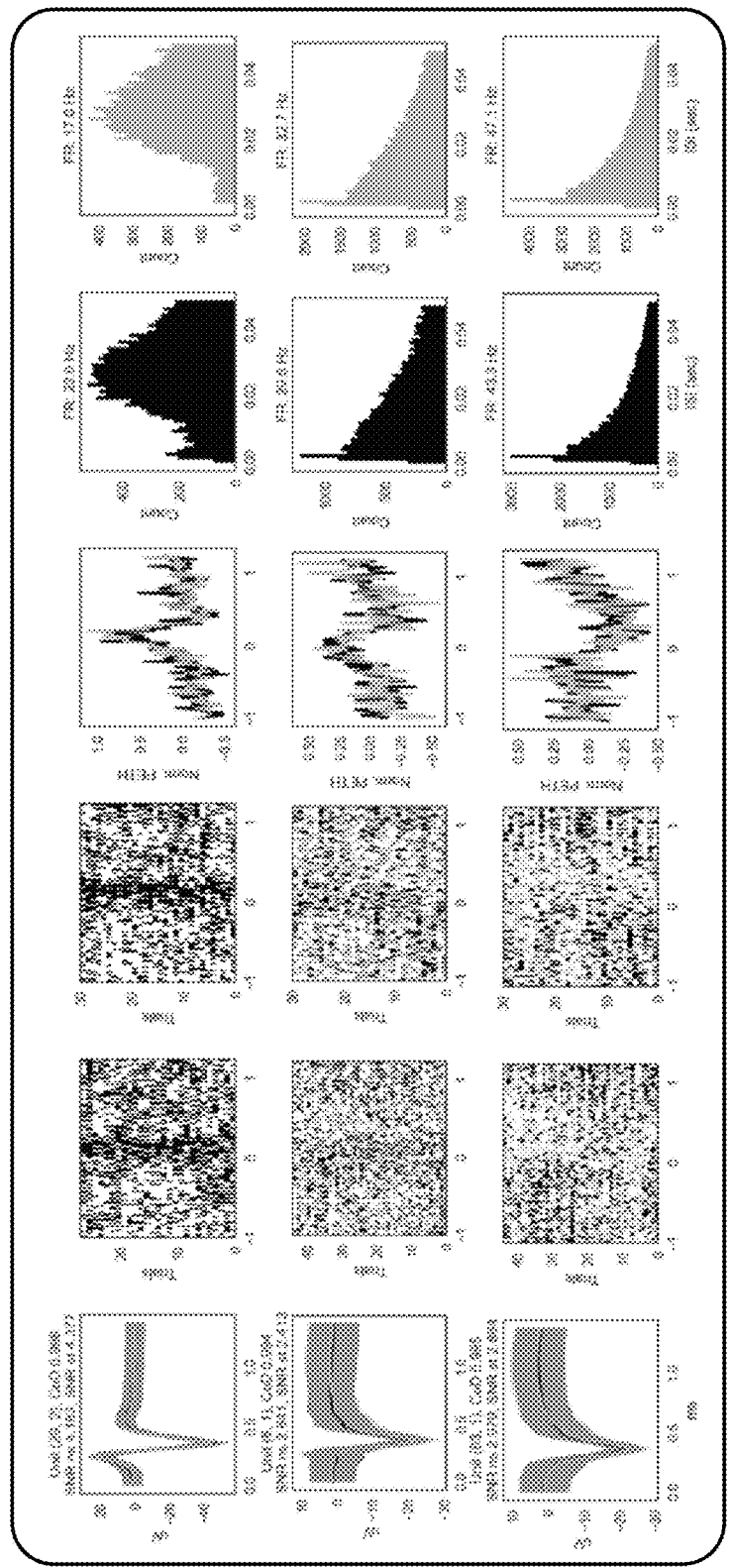
Figure 13D:
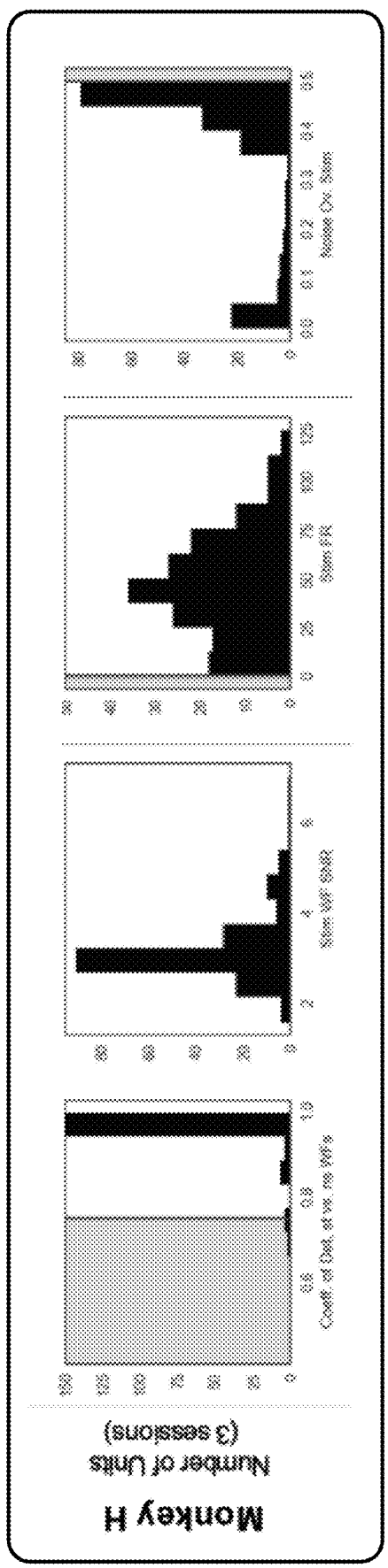

The efficacy of the optimized waveform (specifically, +3 hz and −10 Hz waveform) was further qualified by computing length of sequence propagation, or how many more pools the sequence travels before failure compared to no simulation. Overall input parameters were assessed, the designed waveform propagated ~19 pools further than no stimulation (vs ~11 pools for 3 Hz ACS). Averaged over all input parameters (y-axis of FIG. 12H), the optimized waveform improved sequence propagation for all 9/9 phases compared to only 5/9 phases for 3 Hz ACS. The designed waveform is thus closer to an "ideal" purple region (FIGS. 12F, 12I). In contrast, changes in stimulation amplitude or frequency could only jointly increase or decrease the mean and phase effects together (FIGS. 12C, 12E).

Figure 3:
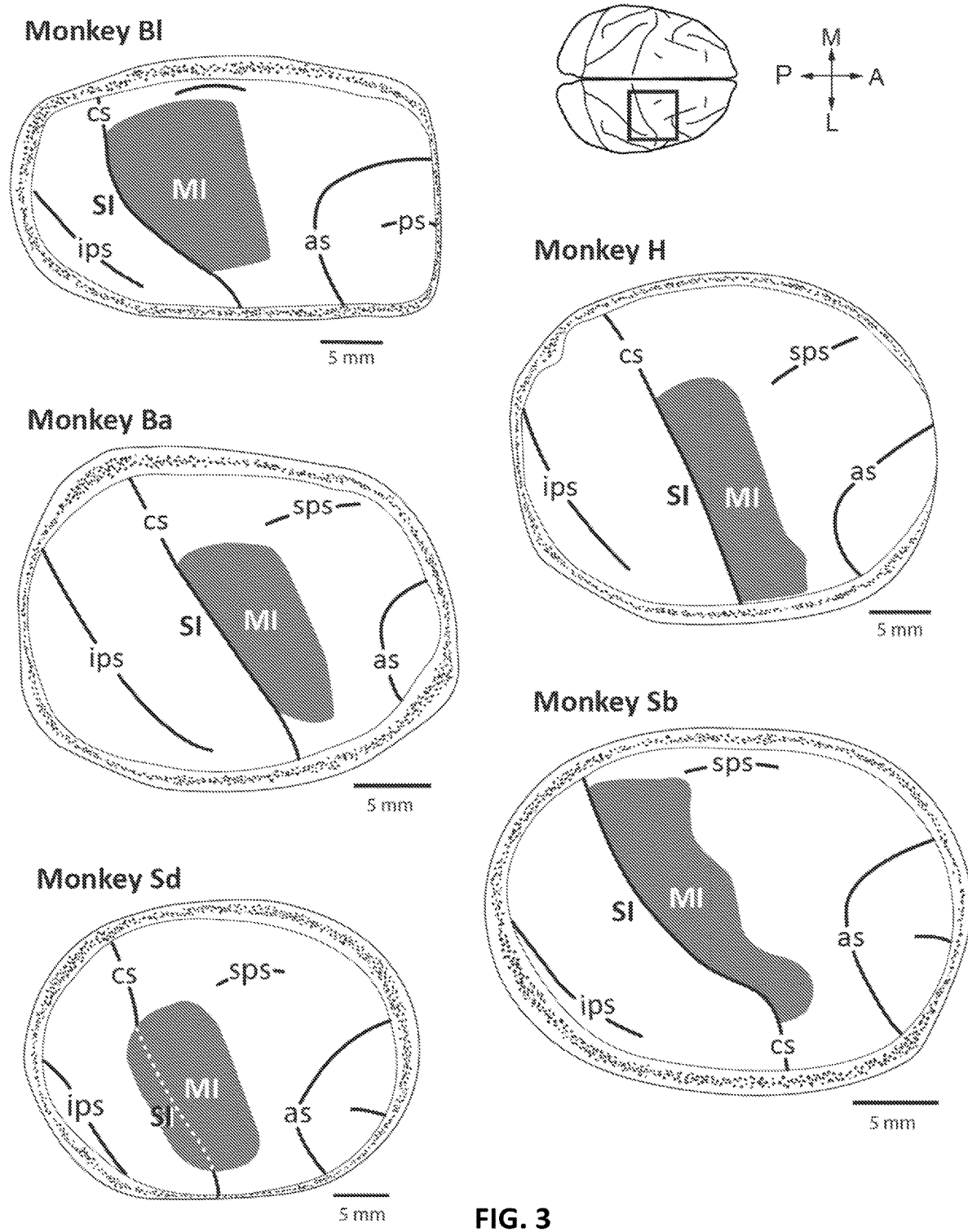
FIG. 3 shows lesion line drawings, related to FIG. 1B. Line drawings of the surface of the right hemisphere cerebral cortex exposed by the craniotomy during the stroke-induction and electrode implantation surgery. The grayed area illustrates the location of the lesion site in primary motor cortex (Monkeys B1, H, Ba, Sb) and primary motor and somatosensory cortex (Monkey Sd). Drawings were created from high resolution digital photographs taken during surgery. Abbreviations: SI=primary somatosensory cortex, MI=primary motor cortex, ips=Intraparietal sulcus, cs=central sulcus, as =arcuate sulcus, sps=superior precentral sulcus, ps=principal sulcus.

In any of the experiments described herein, following task training, animals underwent a stroke-induction and microelectrode array implantation surgery. Preoperatively, animals were sedated with ketamine hydrocholoride (10 mg/kg), administered atropine sulfate (0.05 mg/kg), prepared and intubated. They were then placed on a mechanical ventilator and maintained on isoflurane inhalation (1.2-1.5%). Animals were positioned in a stereotactic frame (David Kopf Instruments, Tujunga, CA) and administered mannitol (1.5 g/kg) intravenously prior to the craniotomy (note that two animals did not receive mannitol in an effort to improve microelectrode array insertion). A skin incision, bone flap, and dural flap were made over the lateral frontoparietal convexity of the hemisphere and the caudal region of the frontal lobe and rostral region of the parietal lobe was exposed unilaterally. After cortical exposure, the lesion was induced using surface vessel coagulation/occlusion followed by subpial aspiration. In three of the five animals (Monkey B1, Monkey H, Monkey Ba), the lesion target was the forelimb region of primary motor cortex (M1) using anatomical landmarks. Specifically, the lesion extended dorsally to a horizontal level including the precentral dimple (the lateral-most part of the of the M1 leg area) and ventrally to the central sulcus genu (the dorsal most part of the M1 face area). In one animal (Monkey Sb), the central sulcus was slightly expanded, and the rostral bank of precentral gyrus was targeted constituting a lesion in the forelimb region of the "new M1". Finally, in one animal (Monkey Sd), the forelimb region of the surface of both precentral and postcentral gyri were included in the lesion, constituting a sensorimotor lesion. Following resection, a flap of the dura was sutured to cover the lesioned area, while leaving a small window anterior and posterior to the lesion for electrode implantation. Drawings of all 5 animals' lesions are illustrated in FIG. 3 based on photographs taken during surgery.

An 8×8 tungsten microwire multielectrode array with 500 um electrode spacing in both dimensions (Tucker-Davis Technology, Alachua, FL) was mounted to a micromanipulator, attached to the stereotax, and inserted 2 mm into dorsal premotor cortex (PMd) using anatomical landmarks. Array ground and references were tied to titanium skull screws. Another multielectrode array was inserted in primary sensory cortex in all animals but was not analyzed in this study due to inconsistent recording quality.

For structural support 6-8 titanium screws (Gray Matter Research, Bozeman, MT) of length 3 mm or 5 mm were placed around the skull to serve as an anchor for a dental acrylic headcap that was used to secure the microwire electrodes in place and seal the craniotomy. Two or three titanium screws were also placed anterior on the left hemisphere from the craniotomy and lesion and served as one of the ACS stimulation contacts (top right screws in FIG. 5A). These screws were lowered such that they were in contact with the dura. The other stimulation contacts were 2-3 stainless steel screws (Depuy Synthes, Raynham, MA) of length 6 mm or 8 mm and were located just posterior to the craniotomy. Screws were confirmed to be in contact with the dura during surgery and post-mortem.

Following surgery, animals were administered analgesics and antibiotics, and were carefully monitored post-operatively for 7 days.

Prior to surgery, macaques were trained to perform either the pellet retrieval task or the pinch-and-lift task. Briefly, animals were seated in a primate chair outfitted with a door allowing them to interact with the pellet task. To initiate a trial, animals touched a "start screw" that was connected to a capacitive touch sensor. Holding the screw for the random hold time (uniformly distributed between 0.5-0.8 seconds) triggered the automated apparatus to release an edible pellet from an automated pellet dispenser (80209-190S, 142 Lafayette Instrument, Lafayette, IN) into one of five "wells". All five wells had depths of 5.9 mm and diameters of either 13 mm, 19 mm, 25 mm, 31 mm, or 37 mm, with the smaller wells making the pellet retrieval more challenging for animals. Animals had 5 seconds to retrieve the pellet from the well before the apparatus would rotate the well out of view. Animals performed 10-100 trials per day, depending on impairment.

Two cameras (CM3-U3-13Y3C-CS, Point Grey, Richmond, BC, Canada) were mounted to a stainless steel platform providing a side and top view of the animal performing the pellet retrieval task. Camera frames and touch sensor activity were synchronized using the electrophysiology recordings system (Tucker-Davis Technology, Alachua FL).

Offline, videos from individual trials were automatically parsed and manually reviewed to mark trial scores (success, attempt but failure, or no attempt) and behavioral time points. Time points that were manually marked include a) Reach start: time at which hand starts moving toward well from the capacitive start screw, b) Grasp start: time at which the hand arrives at the well, c) Grasp finish: time at which the pellet is in control and the hand starts to retract back towards the mouth. For trials scored as "no attempt", no behavioral markers were noted. For trials scored as "attempt but failure", only reach start and grasp start were noted. For trials marked as "success", reach start, grasp start, and grasp finish were all marked. All analyses excluded trials scored as "no attempt". To produce kinematic trajectories in FIGS. 1C-1D, FIGS. 5A-5D, markerless tracking algorithm DeepLabCut was used to track parts of the hand that were consistently visible throughout the trial.

While the pellet retrieval task resembles many established methods to assess dexterity such as the Kluver board, the inventors observed that the unconstrained nature of the task allowed animals to succeed in the task using variable grasp strategies. In order to constrain the grasp portion of the task and specifically study the pinch grip, thought to be cortically dependent, a task termed the 'pinch-and-lift' task was used. Animals initiate a trial by touching a capacitive touch sensor. A sound cuing successfully contact served as the "go cue". Animals then reached toward a 1.5 cm×4.0 cm slot located 9 cm in front of the capacitive touch sensor. They reached their index and thumb into the slot to pinch and lift "grippers". The grippers were custom-designed and 3D-printed. Grippers used in the pinch-and-lift task are illustrated in FIG. 5E. Grippers were mounted to a device that transmitted the pinch force to a piezo resistive force sensor (FlexiForce A201). Varying the height and width of the grippers varied the difficulty of the task and the amount of force that animals needed to complete the task. Grippers were broadly split into two categories. Grippers were either flat and wide and able to be pinched early after stroke or they were narrow and sloped and required more control and strength to pinch (FIG. 5E, 5F). The grippers were pinched together and then lifted 1.5 cm to a height that allowed the grippers to interrupt an infrared beam (IR Break Beam Sensor, 3 mm LED, Adafruit.com). Animals had to hold the device at the lifted height for 0.25 sec, following which they received a juice reward through a chair-mounted juice tube. Animals had 10 seconds to complete the pinch-and-lift successfully.

The same 2 cameras were used in this task as in the pellet retrieval task. An additional camera was positioned such that it had a lateral view the slot into in order to see index and thumb movements. Trials were automatically scored as "rewarded" or "unrewarded" based on whether the object was lifted above the 1.5 cm height threshold for the 0.25 second hold period. Reach start and grasp finish behavioral markers were determined automatically from the capacitive sensor offset after holding and IR sensor onset respectively. Grasp start was determined based on kinematics that were extracted with DeepLabCut. Specifically, animal wrist position was tracked, and grasp start was marked when the wrist crossed the vertical plane at the front of the slot following release from capacitive touch sensor.

Note that in the pinch-and-lift task, automated hand tracking was used to identify the grasp start behavioral mark from video data (necessary for computation of reach duration and grasp duration but not reach-to-grasp time) and could not identify grasp start due to camera occlusion in 18 trials. However, reach start and grasp finish were identified from task sensors, so there are 18 more trials included in the statistics for reach-to-grasp-time than reach duration and grasp duration in FIGS. 5G, 5H.

For both tasks, reach duration was defined as the time between reach start and grasp start. Grasp duration was defined as the time between grasp start and grasp finish. Reach-to-grasp duration was defined as the time between reach start and grasp finish. Normalized reach time, grasp time, and reach-to-grasp time were computed in some cases in the pellet retrieval task (e.g. FIG. 1) in order to account for the differences in difficulty for different well-diameters. All metrics for were normalized by dividing by the average of the pre-stroke performance for that well (see FIGS. 2A-2D for pre-stroke averages). Finally, trials were label as "single grasp attempt" or "multi grasp attempt" depending on the number of grasp attempts needed to complete the trial.

In FIG. 1, all days where behavioral metrics were not significantly different from pre-stroke baseline (Student's t-test comparing reach-to-grasp durations for wells performed that day) were considered in the "recovered" category. The "early" category was composed of the first two sessions where more than 5 rewarded trials were performed. "Intermediate" days were after "early" and before "recovered". Note that rate of recovery varied from animal to animal including how soon they were able to participate in doing the tasks. Due to this, animals began participating in tasks at different days post stroke, and the animal-specific "early", "intermediate", and "recovered" phases fell at different days post stroke.

Raw neural signals were acquired at 24414.0625 Hz using Analog PZ5 Pre-amplifier, RZ2 Bioamplifier, and RS4 Data Streamer (Tucker-Davis Technology, Alachua, FL). Offline, signals were median subtracted (median computed on each bank of 16 channels in array) to reduce motion artifacts and external noise and then bandpass filtered between 300 Hz and 6000 Hz. Spikes were then extracted from signals using MountainSort. For the recovery datasets (FIG. 1, FIG. 4), all waveforms with noise overlap metrics <0.4 and SNR metrics of >1.5 were visually inspected and selected for analysis. Noise overlap provides a prediction of the fraction of noise included in the unit cluster. Lower values indicate better isolated units with less noise. SNR is defined as the peak minus trough of the average waveform divided by the standard deviation of the waveform and was computed in MountainSort. For sessions where neural data is recorded during ACS, more lenient criteria were used for unit inclusion due to the small number of sessions. In these datasets, all waveforms with noise overlap metrics <0.5, SNR metrics of >1.5 were considered for inclusion. Mean waveforms recorded on the same channel during ACS and sham sessions were compared using the coefficient of determination, and units with CoD >0.75 were included in analysis. For FIGS. 7A-7E analyses, only units with mean firing rates >0.5 Hz over the course of the full recording session were included in analysis. For FIGS. 8A-8C and 9A-9G units with mean firings rate >0.5 Hz in the time window of −5 seconds to 5 seconds with respect to reach start over all trials were included in analysis. Examples of units (waveforms, rasters, trial-averaged activity (PETH), and ISIs) are shown in FIG. 13 along with distributions of unit metrics over the full population.

After spike sorting, all units were binned at 20 ms bins and smoothed using a Gaussian waveform with a standard deviation of 60 ms, unless otherwise noted. Units were then z-scored. The mean and standard deviation of unit activity 5 seconds before reach start to 2.5 seconds before reach start was used to z-score each unit. The local field potential signal was also acquired at a sampling rate of 1017.25 Hz.

ACS was delivered via skull screws implanted during surgery. Screws were implanted such that they were touching the dura. A set of three stainless steel screws were implanted in the skull just posterior to the edge of the craniotomy (right hemisphere) which extended back to expose somatosensory cortex but not far enough to see intraparietal sulcus. On the left hemisphere, 2-3 titanium screws were implanted frontally, about 1 cm lateral of midline and 1 cm anterior of the coronal suture. All screws were connected to PFA-coated stainless steel wire (Diameter: 0.005 in. bare, 0.008 in. coated, AWG: 36 bare, 32 coated, Annealed, 110-140 kPSI, 100 ft., AM Systems, Sequim, WA). Wires were soldered to an Omnetics connector (PS 1-10-SS-LT, Omnetics, Minneapolis, MN). The connector was secured in the final headcap using bone cement (Stryker 6191-1-010 Simplex P, Kalamazoo, MI). Screws were also surrounded by bone cement making it unlikely that current delivered through screws was shunted by skin or muscle. Screws were confirmed to be touching dura post-mortem.

When stimulation was delivered during behavioral sessions, 1-3 stimulus output channels from an MCS STG4004 (Multi Channel Systems, Reutlingen, Germany) were connected to the stimulation screws. Each of the 1-3 active output channels had a positive and negative terminal that were each connected to a different screw. All positive terminals were connected to the stainless steel screws posterior to the craniotomy on the right hemisphere and all negative terminals were connected to titanium screws on the left hemisphere anterior to the craniotomy. The MCS was operated in dipolar current control stimulation mode, meaning that the negative channel emitted an inverted version of the waveform that the positive channel was emitting. Thus, stimulus currents listed below define the peak-to-peak amplitude of the 3 Hz sine wave output by each channel.

Various stimulation amplitudes were attempted in each animal (See FIG. 15, table 1, for full list), varying from 0.5 mA-3.0 mA. In order to reduce charge density on screws, for larger stimulation amplitudes multiple pairs of screws were used (e.g. 3.0 mA involved 3 output channels from the MCS, each attached to one positive stainless steel screw and one negative titanium screw and each channel injecting 1.0 mA).

During ACS blocks, stimulation was started 1-2 minutes prior to block start, and turned off after the last trial was completed. In behavioral sessions with both stimulation and sham blocks, breaks of 1-2 minutes occurred in between stimulation and sham blocks. During the sham sessions, animals were still connected to the MCS system (including the omnetics clip but the stimulator was turned off). Some pairs of stimulation and sham sessions occurred across days (e.g. ACS session on one day, sham session on next day). Since experiments took place on Mon Tues, Thurs, and Fri, pairs of data were always Mon-Tues pairs or Thurs-Fri pairs if pairs were done across days.

After animals were sacrificed, brains were perfused with 1 L of cold saline followed by 4% paraformaldehyde fast for 10 minutes, then slow for the remaining time. Post fixation of the brain was 10% glycerol after 5-6 hours, then 20% glycerol after about 24 hours. Prior to imaging (weeks later), for the subset of animals where MRIs were acquired, brains were immobilized in a 1-2% agar solution, and transferred back to the 20% glycerol solution after imaging. Imaging was done using a RARE T2-weighted scanning protocol (FIG. 1B).

In order to assess how similar single trial neural activity was to an estimate of "good neural activity", for each animal on each session, activity from rewarded trials were trial-averaged with normalized reach-to-grasp times that fell below a specific threshold. Thresholds were defined by pooling the normalized reach-to-grasp times across the full recovery curve and training a linear discriminant analysis (LDA) classifier (sklearn.discriminant-analysis. LinearDiscriminantAnalysis, to separate single grasp attempt vs. multi grasp attempt trials based on normalized reach-to-grasp time. The classifier threshold was used over all sessions of recovery, though the specific neural template used for analysis was computed specifically for each session. Animals had slightly different thresholds, though all were between 2.2-2.5 normalized R2G units.

For a given session, once fast (normalized reach-to-grasp time below animal-specific threshold), rewarded trials were identified, the neural activity from 1 second before reach start to 1.25 seconds after reach start was trial-averaged to create a units-by-time template of "good neural activity" (FIG. 1E). Then, individual trials were compared to the template with a correlation coefficient.

In order to control for i) differences in the number of units, ii) different numbers of "fast" trials, and iii) single trials sometimes being compared to a template that included that same trial in the trial-averaged estimate the inventors developed two subsampling procedures and a policy for ensuring (iii) did not influence results. First, the minimum number of units over all analyzed sessions was computed for each animal ($N_{min}$). Second, the minimum number of fast, rewarded trials over all analyzed sessions was computed for each animal (Rew/Trl$_{min}$). Only sessions that met the criteria for minimum number of units and trials were included in FIGS. 1F-1G. Then, for each session, first the number of fast, rewarded trials that were used to compute the template was subsampled. The number of units that were used in computing the correlation coefficient between single trials and the subsampled template was then subsampled. Finally, if the single trial that was being compared to the template had also been included in computing that particular template, the template was recomputed after removing that trial before computing the correlation coefficient for that trial. Each template subsampling and unit subsampling was repeated for a total 1000 subsamples, resulting in 1000 estimates of the correlation coefficient for each single trial. The 1000 repetitions were averaged to produce one correlation coefficient for each single trial.

Dimensionality of neural data was computed (FIG. 4A-4J) using neural activity from all trials from 1 second before reach start to 1.25 seconds after reach start. Similar to the template matching, trials (Trl$_{min}$) and units ($N_{min}$) were subsampled to prevent differences in numbers of units and numbers of trials influence this metric. For each session, units, and trials were subsampled resulting in a Time×units×trials data matrix. This was transformed into a Time*trials×units data matrix. PCA was performed on this matrix, and the number of PCs needed to account for 80% of the total variance were noted. Each session's dimensionality was computed as the mean of the 1000 subsampled dimensionality estimates for that session.

Temporal predictability (TP) of the neural data (FIG. 4A-4J) is defined as the amount of change in future neural activity ($dX_t$) that can be predicted as a linear function of current neural activity ($X_{t-1}$):

$$dX_t = X_t - X_{t-1} = AX_{t-1}$$

TP=variance accounted for in $dX_t$ by $AX_{t-1}$.

In this equation, $X_{t-1}$ refers to the neural activations. TP was computed using the same sub-selected datasets used to fit the dimensionality (above), resulting in 1000 estimates of the temporal predictability which were averaged to yield one value of TP per session.

In order to estimate the fraction of multiphasic versus monophasic units in the recovered state, neural pre-processing procedure was slightly modified. Instead of smoothing neural data with a Gaussian filter with standard deviation equal to 60 ms, instead a Gaussian filter with standard deviation equal to 20 ms was used in order to preserve temporal variation. Each unit's activity was then z-scored the same way as described in the preprocessing section.

Neural activity during fast, rewarded trials was then averaged to yield a trial-averaged response for each unit. The autocorrelation of each trial-averaged response for each unit was computed. The autocorrelation response was then smoothed with a 5 point box-car filter. Peaks were then detected using scipy.signal.find_peaks, which identifies all local maxima (individual points in a one-dimensional array of data points where a given point is higher than its neighbor on either side). No other criteria needed to be met for a peak to be identified (i.e. no prominence, width, height criteria). If there were peaks in the autocorrelation response between 0.1-0.5 seconds lag, a unit was called "multiphasic".

Units that have maximum values greater than 1 std. or less than −1 std. in their trial-averaged response were termed "task-modulated".

Local field potential (LFP) signals from 64 electrodes in PLC were recorded at a sampling rate of 1017.25 Hz. Signals from each channel were z-scored (mean and standard deviation estimated over the full recording session). A median signal was computed across all channels and subtracted away from each channel to decrease common noise and minimize volume conduction. Each channel was then bandpass filtered in the LFO range of 1.5-4 Hz ($5^{th}$ order bandpass butterworth filter, scipy.signal.butter).

To compute inter-trial phase coherence, the hilbert transform was applied to the LFO signals and the phase was extracted. LFO phases aligned to reach start were then gathered into a channels×time×trials array. The mean resultant vector length was computed over trials to yield a channels×time array which was the ITPC. Finally, ITPC values were baseline normalized by average ITPC in the period [−5, −2.5] seconds prior to reach start.

Stimulation fields (FIG. 7A-7E) were computed by taking the value of the local field potential on each channel at the peak, trough, or zero-crossing (with positive derivative) of the stimulation waveform. At each point of interest in the stimulation waveform, the voltage values of the microelectrode array were extracted and arranged in an 8×8 matrix corresponding to the electrode locations. Voltages were spatially smoothed (imgaussfilt in Matlab with a standard deviation of 0.5). The gradient function in Matlab was then used to compute the voltage gradient (V/m) in the horizontal and vertical direction across the grid. Estimates of the gradient were averaged over all instances of the peak, trough, or zero crossing for a given ACS session. For each electrode, the negative of the mean horizontal and vertical gradient values were plotted as an arrow to illustrate negative gradient direction (FIG. 7B, center) and the magnitude of the horizontal and vertical values was computed to yield a single V/m estimate for each electrode (FIG. 7B right).

To compute entrainment of units to the stimulation waveform (FIGS. 7A-7E), data across the full behavioral session (not split into trials) was used. For each unit, the phase of each spike time was aggregated. The Rayleigh test at a significance level of 0.05 was applied to test the non-uniformity of each unit's phase distribution. For this analysis: 1) percentage of entrained units using all extracted units and 2) percentage of entrained units using a subset of high SNR units was reported. Units with SNR values >3.5, and noise overlap values <0.4 were considered "high SNR units". See Electrophysiology section for metric definitions.

To infer if there was a population preference of preferred stimulation phase across all units, the preferred ACS phase across all units (FIGS. 7A-7E) was aggregated. The distribution of preferred phases of all units was compared to the distribution of preferred phases of only significantly entrained units using the Kuiper's test (circular version of Kolmogorov-Smirnov test). The distribution of preferred phases of all units was assessed for non-uniformity using the Rayleigh test. Since both animals' phase preference distributions were significantly different than a uniform distribution, the excitable zone was estimated using the circular mean as the center of the excitable zone and $1.5 \times (95^{th}$ confidence interval computed using pycircstats.descriptive.mean_ci_limits (https://github.com/circstat/pycircstat)) as the width of the zone.

Solely for visualization of the distribution of preferred phases for each animal (FIGS. 8A-8C), a kernel density estimation (KDE) using a vonMises kernel function method to fit a probability density function (PDF) to the preferred phases of units for each animal. The vonMises functions utilized a kappa value estimated from the preferred phase distribution for each animal. The PDF was normalized to fall between 0 and 1.

In order to visualize the relationship between phase of stimulation and behavioral metrics such as reach-to-grasp time (FIGS. 8A-8C), a non-parametric smoothing approach was applied to the dataset of all rewarded ACS trials for an animal. Each data point plotted the phase of ACS at reach start versus reach-to-grasp time. To fit a smooth curve to this dataset, lowess (locally weighted scatterplot smoothing), using 25% of the data used to estimate each reach-to-grasp-value (statsmodels.api.nonparametric.lowess in python) was applied. In order to force the resultant function to fit a circular smoothing function (similar values at $-\pi$ and $\pi$), data points were repeated twice with phase values were shifted by $-2\pi$ in the first repeat, and shifted by $+2\pi$ for the second repeat.

Full trial activity was split into a "reach", "reach-grasp", and "grasp" ensemble for analysis in FIGS. 9A-9G. These ensembles were spatiotemporal subsets of the full time-by-neural activity array of data. The reach ensemble consisted of a time window (−1.0, 0.25) with respect to reach start. The reach-grasp ensemble consisted of a time window (−0.25, 0.25) with respect to reach start. The grasp ensemble included a window (−0.25, 0.45) or (−0.25, 0.85) with respect to grasp start. The different windows reflected different average grasp durations during sham/ACS session pairs for the different animals (Monkey H and Monkey B1 respectively).

Units were assigned to an ensemble depending on their firing rate during task-related activity. Firing rate activity was aggregated during all reach periods (reach start→grasp start) and grasp periods (grasp start→grasp finish) and compared to a baseline period (−5 seconds prior to reach start to 5 seconds after reach start). A Student's t-test was used to determine whether a unit was significantly modulated compared to baseline. Following significance tests, the following categories were made:

Reach Units: Units that were significantly modulated above baseline during reach periods and not significantly modulated above baseline during grasp periods Grasp Units: Units that were significantly modulated above baseline during grasp periods and not significantly modulated above baseline during reach periods Reach-grasp Units: Units that were significantly modulated above baseline during reach periods and grasp periods.

None units: Units there were not significantly modulated.

To assess mean changes in unit activity, the modulation (max−min) of each unit's time-varying, trial-averaged pattern was computed for the reach, reach-grasp, and grasp ensembles (FIGS. 9A-9B).

For each pair of units within an ensemble, the correlation coefficient between the units' activity patterns over all trials (restricted to the window of analysis for that particular ensemble) was computed (FIGS. 10A-10G).

To study ensemble co-firing, Factor Analysis (FA), a model specifically designed for parsing variance that is shared across observations from variance private to each observation was used. FA models the joint distribution of N units spike at a given time point ($x_t \in R^N$) as a sum of 1) a mean rate $\mu \in R^N$, 2) private variance $\psi_t \in R^N$ where $\psi_t \sim N(0, \Psi)$ and $\Psi$ is a diagonal covariance matrix, and 3) shared variance due to a low-dimensional (here, one-dimensional) latent variable $z_t \in R^K$, K=1 where $z_t \sim N(0, I)$. Expressed fully, $x_t$ is modeled as $x_t = Uz_t + \psi_t + \mu$, or $x_t \sim N(\mu, UU^T + \Psi)$.

The model is fit using expectation-maximization (sklearn.decomposition.FactorAnalysis). The 1D-SOT (shared over total) is defined as: trace($UU^T$)/trace($UU^T + \Psi$), reflecting fraction of the total variance of $x_t$ that can be modeled as shared across units.

Since the 1D-SOT was computed in sessions with matched numbers of units (stim vs. ACS sessions), no unit subsampling was done. Trial numbers were subsampled so that FA models were fit on equal numbers of data between sham and ACS (and inside vs. outside EZ). Models were fit 100 times on different subsamples of data. 1D-SOT estimated in different subsamples were averaged to yield a single 1D-SOT estimate per session and condition (sham vs. ACS or inside EZ vs. outside EZ).

For one animal on one sham-ACS session pair, only one unit was in the grasp ensemble. Thus, grasp ensemble 1D-SOT comparisons include one fewer session pair than reach ensemble and reach-grasp ensemble comparisons.

When grasp-ensemble 1D-SOT was computed over late-state recovery (intermediate to recovered), all recorded units were analyzed (did not restrict to significantly modulated units as in "ensembles" analysis in FIG. 5) in the time period of −0.25 seconds to 0.25 seconds following grasp start. The number of trials and units were subsampled to match across compared conditions.

An 86-pool feedforward neural network was implemented using the software Brian2. Model parameters are listed in FIG. 16 (table 2) and used from previous studies. Briefly, a network was formed by connecting 86 pools of 100 integrate and fire neurons (total of 8600 neurons). Neurons from pool 1 were connected to neurons from pool 2 with a probability of $p_{cx}$. There were no intra-pool connections, and no connections from neurons in pool i to any neurons except those in pool i+1. All connections were excitatory and post-synaptic potentials were modeled with an alpha function with parameters (see, e.g., FIG. 16, table 2) such that the effect of post-synaptic potential on membrane voltage was a time to peak of 1.8 ms and membrane voltage deflection of 0.14 mV. Each post-synaptic potential was triggered 5 ms following the pre-synaptic neuron spiking. If neurons received ACS input (FIGS. 11A-11I, 12A-12I), ACS was modeled as an input current into all neurons. All neurons received the same ACS input.

Figure 11I:
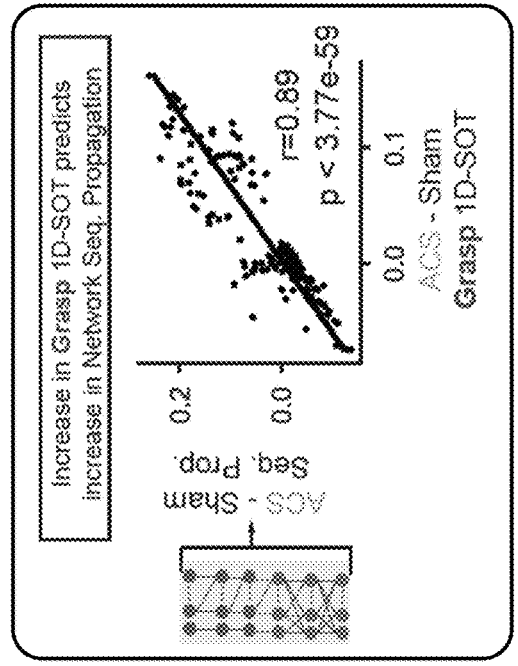
FIG. 11I illustrates a correlation between change in 1D-SOT in grasp ensemble vs. change in propagation (linear correlation, r=0.89, p<3.77e-59, N=171). Each point is average over many simulations for each impaired R2G input parameter-by-ACS-phase combination.
Figure 11H:
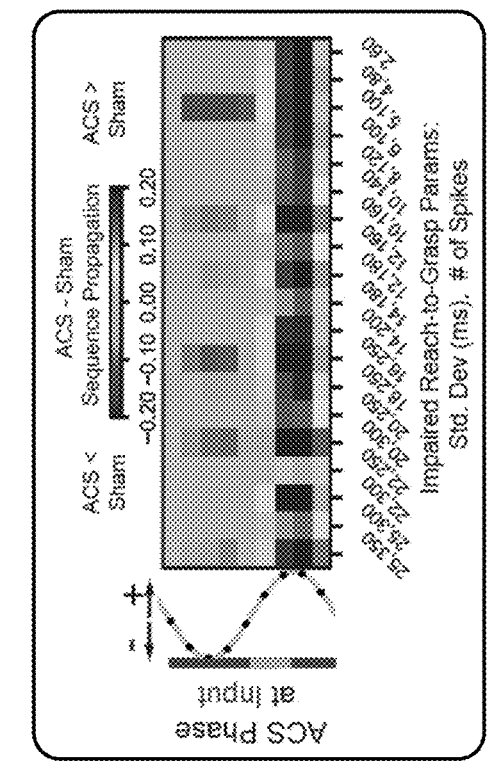
FIG. 11H shows a change in sequence propagation (ACS—sham) over all impaired R2G inputs (x-axis) for alignment of input to ACS phase (y-axis).

To trigger the start of the simulated activity, N spike times were drawn from a Gaussian distribution with a mean start time ($\mu$) and a standard deviation ($\sigma$). At each input spike time, all neurons in pool 1 experienced a post-synaptic potential. In FIG. 11D, 11H-11I sequence propagation was plotted as a function of N and $\sigma$ with $\mu$ set to 400 ms (mean of input spike times=400 ms into simulation). In FIG. 11F-11I, N, $\sigma$, and $\mu$ all vary, where $\mu$ dictates what phase of ACS the input is aligned to. Depending on the properties of the input (N, $\sigma$, $\mu$) and of the network connectivity ($p_{cx}$), the input could trigger a sequence of activity or not. Each simulation was run for 1.5 seconds. All analysis of the simulations was performed on binned spike counts (20 ms binsize) smoothed with a Gaussian kernel (60 ms standard deviation) as in the true experimental data analysis.

Figure 14A:
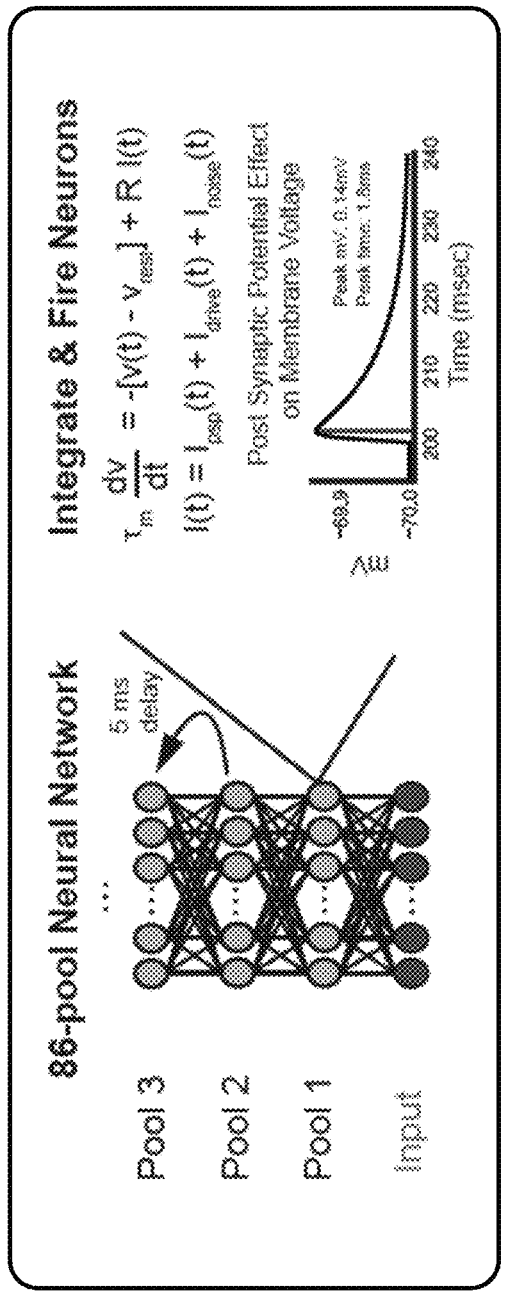
FIG. 14A shows a schematic of 86 pool neural network with each pool consisting of 100 integrate and fire neurons. Right bottom illustrates post-synaptic potential effect on membrane potential.
Figure 14B:
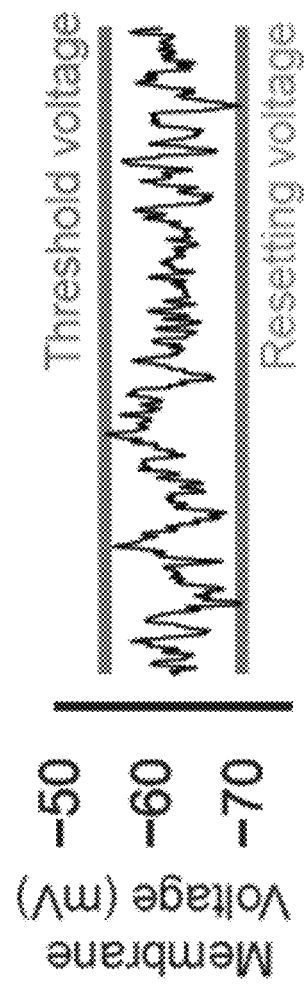
FIG. 14B is an example of how background drive and noise affect membrane potential.
Figures 14C, 14D:
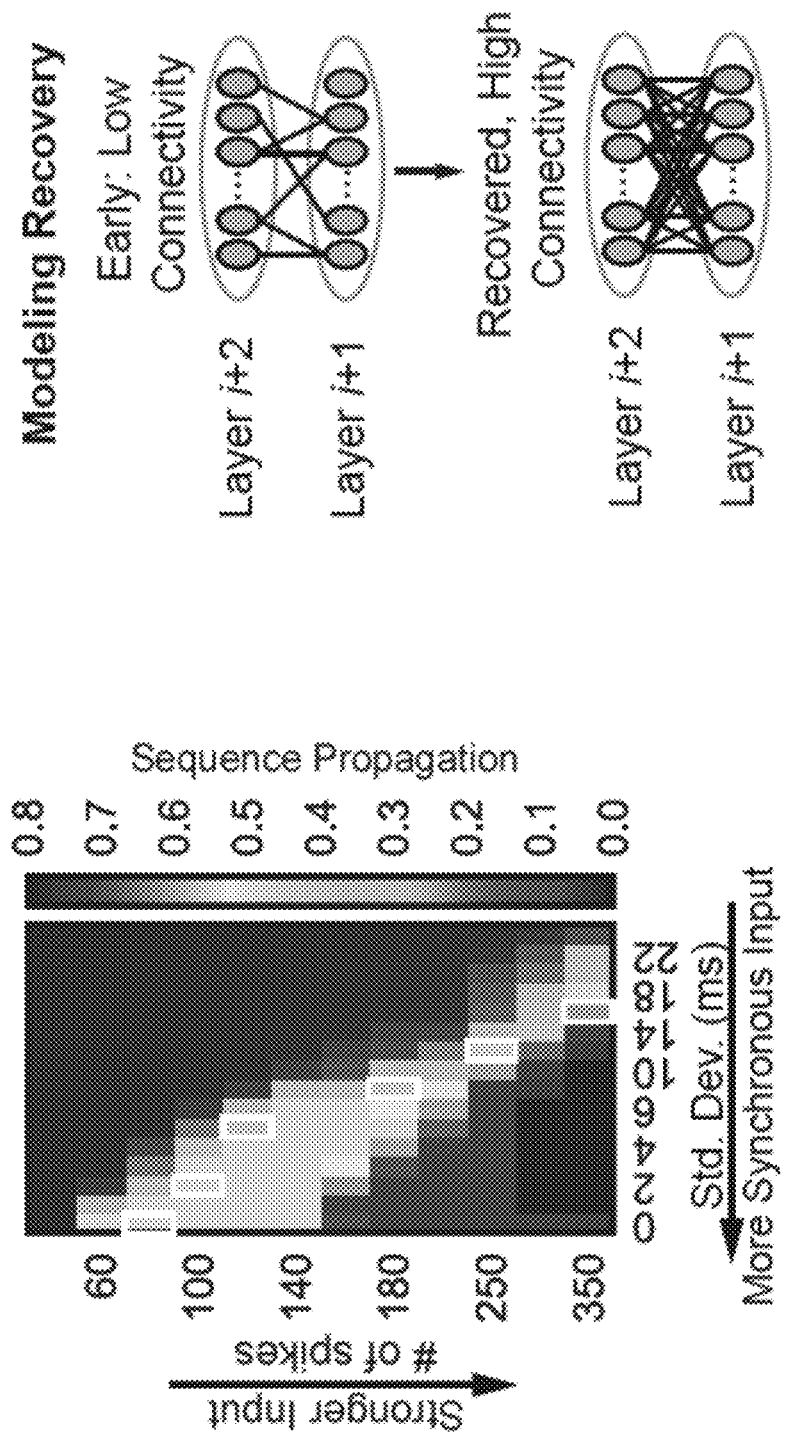
FIG. 14C is a sequence propagation (color) as a function of σ (standard deviation of input, x-axis) and N (number of input spikes, y-axis). Similar to FIG. 11D but for a network with full connectivity. Top right of the plot is blue indicating little to no sequence triggered due to inputs that are dispersed (high σ) and weak (low N). Bottom left of the plot is red indicating longer sequence propagation due to inputs that are synchronous (low σ) and strong (high N). White boxes indicate input parameters analyzed in FIGS. 14F-14G.
FIG. 14D shows a model of a perilesional network that is still active but is re-developing connectivity to drive reliable sequential patterns following stroke, inter-pool connectivity was pruned randomly.
Figure 14E:
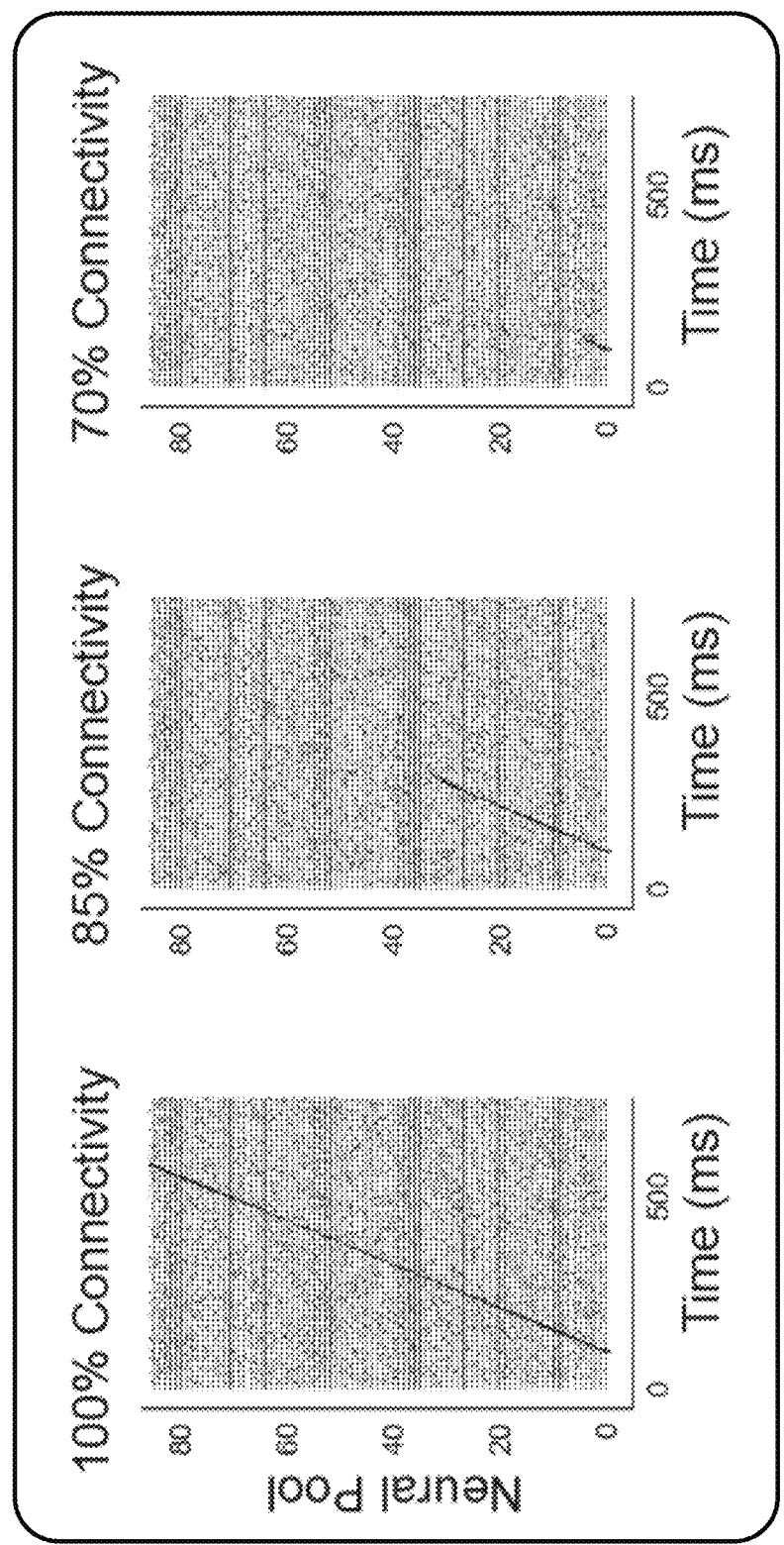
FIG. 14E shows examples of inputs (parameters correspond to leftmost white box in FIG. 14C) driving sequential activity in a network with full connectivity (left) and reduced inter-pool connectivity (center, right). Low connectivity impedes successful sequence propagation.

For the network in FIG. 14B-14C, all inter-pool neural connections were set to $p_{cx}$=100%, and in Fig. S7E-H $p_{cx}$ varied from 70%-100%. For the network in FIGS. 11-12, an 86-pool network was also implemented where the first 43 pools were loosely designated as "reach pools", and the second 43 pools were loosely designated as "grasp pools". Connectivity between reach pools was 100%, whereas connectivity from the last reach pool to the first grasp pool and between the grasp pools was 85%.

Each simulation of the network produced a spatiotemporal pattern of activity. Neural activity was binned and smoothed (see above) and assessed for how closely the produced spatiotemporal pattern matched a fully propagated template spatiotemporal pattern. The ideal spatiotemporal pattern was created assuming that the statistics of the input pattern (N, $\sigma$) would faithfully be propagated through the network such that each neuron in each pool i would exhibit a burst of activity with standard deviation $\sigma$, centered at $(i-1)*(5 ms+1 ms)+\mu$. The inter-pool delay was estimated to be 6 ms based on empirical results (5 ms synaptic delay+PSP function). This "ideal" spatiotemporal pattern was correlated with the simulated patterns at each trial to get a "sequence propagation" metric. This analysis was identical the template match analysis from FIG. 1, but instead of using trial-averaged activity to create a template, an ideal template was created from knowledge about the network.

In FIG. 11D, input parameters with sequence propagation >0.03 and <0.15 were selected as parameters where sequences were successfully initiated but incompletely propagated.

1D-SOT (FIG. 11F, 11I) was computed using only the 100 neurons in pool 1 ("reach"), pool 43 ("reach-grasp"), and pool 53 ("grasp"). Spike counts were binned at 20 ms using neural data from the full trial and smoothed. A 1-factor Factor Analysis model was fit, and the 1D-SOT as defined above for experimental data was reported.

Figure 14F:
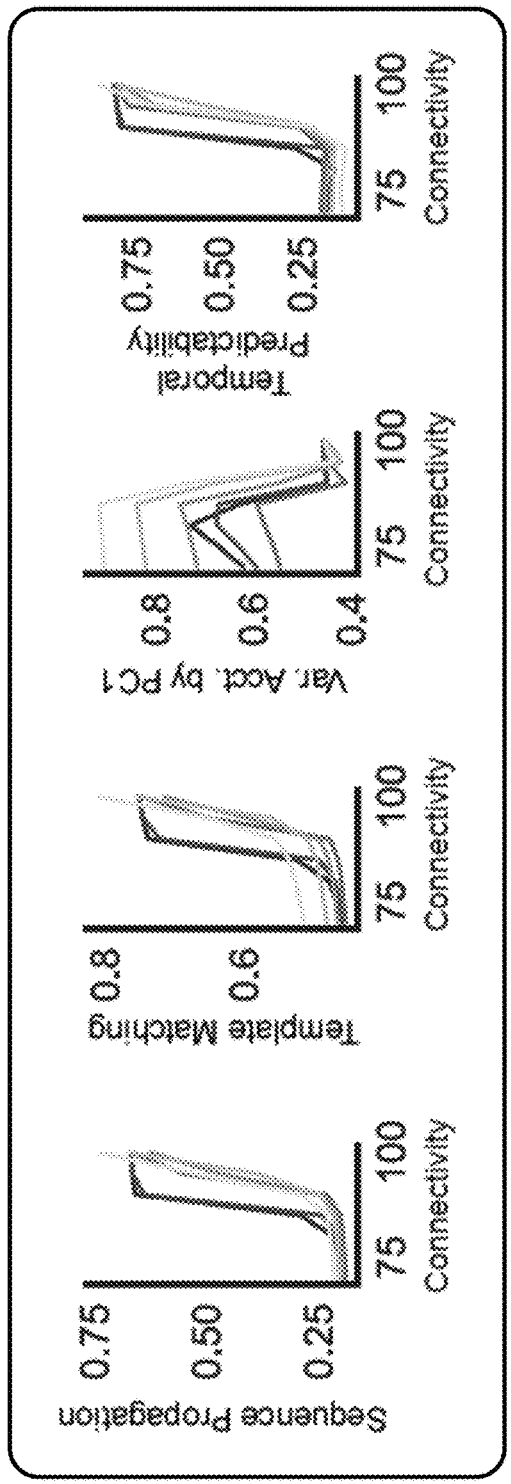
FIG. 14F shows input parameters boxed in FIG. 14C were selected for analysis. Changes in sequence propagation, template match, variance accounted for by PC1 (proxy for dimensionality in high-dimensional network), and temporal predictability as a function of increasing connectivity is plotted. Each line indicates a different input parameter regime (boxes from FIG. 14C). With increases in connectivity, sequence propagation improves (column 1), template matching improves (column 2), dimensionality increases (variance accounted for by PC 1 reduces, column 3), and temporal predictability improves (column 4). The changes in template matching, dimensionality, and temporal predictability all re-capitulate the observed changes in the experimental data (FIGS. 1A-1H), suggesting that recovery and the emergence of reliable, high-dimensional, temporally predictable neural sequences may be associated with an increase in network connectivity.
Figure 14G:
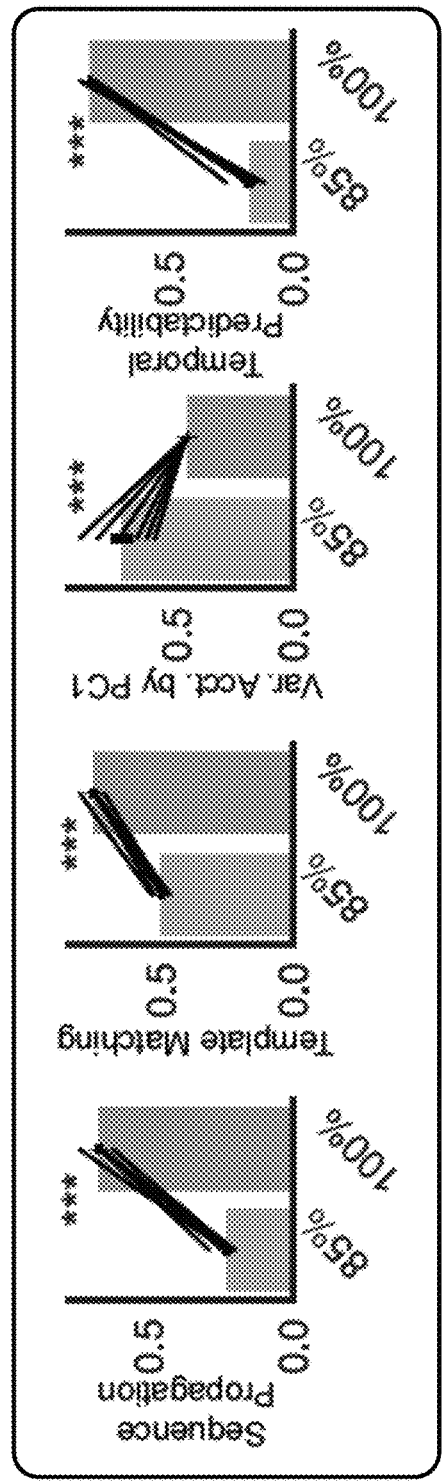
FIG. 14G shows sequence propagation, template matching, variance accounted for by PC1 (proxy for dimensionality in high-dimensional network), and temporal predictability all significantly change with connectivity increase from 85% to 100% (mixed-effect model with input parameters modeled as random effect: sequence propagation: slope=0.4417, t(10)=23.67, p<8.1e-124, template match: slope=0.256, t(10)=29.15, p<8.4e-187, variance accounted for by PC1: slope=−0.278, t(10)=−5.39, p=7.29e-8, temporal predictability: slope=0.642, t(10)=27.3, p<3.7e-164).

Simulated data was binned in 20 ms bins and bins were smoothed (Gaussian filter, 60 ms std) as was done in the experimental data in FIGS. 1A-1H and FIG. 10A-10G. Identical to the template match analysis in FIGS. 1A-1H, here all 20 simulated trials are averaged together to create a trial-averaged template, and single trials are correlated with the template to assess consistency of template match (FIG. 14F-14G).

In the simulated networks, dimensionality of neural activity was 8600 (86 pools×100 neurons/pool), making the use of PCA poorly conditioned (computing entries of an 8600× 8600 covariance matrix far exceeds amount of simulated data). Since the inventors knew what the expected network structure was and knew that they were sampling from a population where signals were shared over many neurons (in contrast to the unknown structure in the real data analysis), the activity patterns of neurons over their pool (e.g. sum neurons 1-100, 101-200, etc.) was summed to yield a reduced set of observations (#observations=#pools=86). PCA was then applied to the reduced set of observations. Instead of reporting the number of PCs that are needed to explain 80% of the variance, the amount of variance accounted for the by the first PC was reported. The number of PCs needed to explain 80% of the variance was often high and included PCs that did not explain sequence-related activity. The threshold for reporting number of PCs could have been lowered, but instead the amount of variance captured by PC 1 was reported, since PC1 was always relevant to sequence activity (FIGS. 14F-14G).

A similar dimensionality problem presents when using high dimensional data to estimate a linear dynamics matrix. Here, the inventors again took advantage of their knowledge of the structure of the sequence and first fit a Factor Analysis model with twenty-five dimensions (86 pools, each activating at 6 ms offset from each other yields an 86*6=516 ms sequence. 516 ms binned into 20 ms bins yields 25, hence 25 factors) to the data. The 25×25 dynamics matrix was estimated to predict changes in factor activations at the next time point using current factor activations. (FIGS. 14F-14G).

In FIG. 12A-12B, mean improvement in sequence propagation with ACS compared to non-ACS was computed (mean over all input parameters and all phase alignments of input to ACS phase). This mean was the "mean-effect" of ACS. Then the mean over all input parameters was defined yielding a 1×9 vector of mean improvement as a function of phase. The "phase-effect" was defined as the standard deviation of this 1×9 vector, capturing the variance in change in sequence propagation as a function of phase.

Different amplitudes of 3 Hz ACS (FIG. 12C), different frequencies at the same amplitude (FIG. 12D), and novel waveforms (FIG. 12E) were all tested. The novel, or "optimized" waveforms were all charge balanced. All new waveforms were simulated in the same manner as 3 Hz ACS in FIGS. 11A-11I—as an injected current. The same input parameters, number of trials, and analysis methods were for these waveforms as identified in FIG. 11D and reported in FIG. 11F.

To estimate the number of pools propagated (FIGS. 12H-12I), a distribution of the number of spikes in each pool (over 100 neurons) for trials with and without ACS, but no triggered sequence, was computed. The $99^{th}$ percentile of this distribution was set as a threshold (375 spikes). For all trials with simulated sequences without ACS, with 3 Hz ACS, or with the optimized waveform, the highest pool number with activity above the threshold was the "length of propagation" for that trial. For example, if in a trial pools 1-30 had spiking activity >375 spikes, and pools 31-86 had spiking activity <=375 spikes, the number of pools propagated in this trial would be 30.

Figures show mean±s.e.m.; if this was not case, it was specifically indicated. Mostly, linear mixed-effects (LME)

models were used to test the significance of behavioral and neural changes. Using these models accounts for animal-to-animal differences in neural or behavioral measures that may contribute to high variability in pooled data, but which may still have clear within-animal effects. In all cases unless otherwise noted, animal was modeled as a random effect on intercept. Sometimes well-size or gripper identity and session were included as random effects on intercept (indicted when done), and animal was included as a random effect on regression coefficient. The LME model was fit using specified random and fixed effects, and the test statistic and p-value of the regression coefficient for the fixed effect is reported. All random effects, sample sizes, test statistics, and p-values are reported in the results and figure legends. No normality tests were carried out prior to LME use, but individual points have been included in the figures to display distributions. In cases where statistics were applied to multiple metrics (e.g. reach duration, grasp duration, R2G duration), the details (i.e. random effect variables) of the statistical test were not re-printed for metrics immediately following the first in a series of tests. LME models were implemented in python2.7 using the statsmodels "mixedlm" method. Other tests used include Rayleigh tests for non-uniformity of circular distributions and linear regression.

The number of animals was not pre-determined. FIG. 15, table 1, lists which animals were included in which analyses. Animal inclusion/exclusion only reflected whether ACS was tested in a particular animal or whether an animal had sufficient quality of neural recordings to perform an analysis.

FIGS. 13A-13D illustrate example units recorded during ACS, as discussed above in reference to FIGS. 7A-7E, 8A-8C and 9A-9G. Unfortunately, in Monkeys Sd and Sb, neural unit recordings were very poor even without any ACS-related artifacts. It is worth noting that this approach of chronic tracking of behavior, monitoring of activity with and without stimulation has rarely been done in the past. The inventors hypothesize that the probability of achieving reliable chronic recording in a primate stroke model could have been poor due to a variety of factors: for a chronic implantable microwire approach (i.e. implanted during surgery without further targeting), dorsal premotor cortex is more challenging than targeting primary motor cortex due to the thinner cortical layers (PMd, Area 6 cortical layer V depth ~2.5 mm, M1 Area 4 Layer V cortical depth ~3-5 mm estimated from slices from). The inventors have also experienced lower yields and shorter lasting recordings in PMd compared to M1 from previous studies in intact animals.

Following stroke, both in this study and in analogous rodent studies, a low yield of neurons was observed immediately following stroke and an increase in neural yield with recovery. This effect is particularly pronounced for electrodes near the stroke site. This effect is perhaps not surprising, given the loss of connectivity and the evidence of increased tonic GABAergic inhibition in the peri-infarct area following stroke. Further, while strokes were targeted to primary motor cortex, small variations in the vasculature affected by the infarct could have largely variable impacts on the spatiotemporal extent of cortical tissues affected. Following surgery and especially after a stroke, the craniotomy site and cortical tissues around the infarct undergoes transient swelling, which then slow subsides. Electrodes that may be in cortical layers during surgery may be pushed into white matter as swelling and inflammation reduce. In these experiments, neural activity yield must often be sustained for months as animals recover from injury at variable rates. Thus, even early recording success guided by intraoperative recordings may not last throughout the full behavioral recovery.

FIGS. 14A-14G illustrate the effects of network connectivity on sequence propagation, dimensionality, and temporal predictability of simulated activity patterns (similar to that shown in FIGS. 11A-11I).

In general, the methods an apparatuses described herein may drive low-frequency oscillations (LFOs) in cortical regions from subcortical input (e.g., thalamus, striatum, brainstem, etc.). For example, the methods described herein may be used to treat a patient (including, but not limited to a stroke patient) by detecting a directed movement (such as movement of a limb, hand, foot, arm, leg, etc.) or an intended directed movement from a patient and applying a charge-balanced, low-frequency alternating current stimulation ("ACS") to a sub-cortical region of the patient either or both immediately before and/or during the directed movement. The charge-balanced, low-frequency ACS may have a depolarizing phase with a frequency of 15 Hz or less and a hyperpolarizing phase with a frequency greater than 15 Hz, wherein the ACS stimulation field is greater than 1.5 V/m.

FIG. 17 shows one example of an ACS waveform including one or more biphasic pulses each having an amplitude and pules width, where bursts of pulses may be applied with an inter-burst frequency of between 50-250 Hz (e.g., between 50-200 Hz, between 50-150 Hz, between 60-140 Hz, between 75-125 Hz, about 100 Hz, etc.) with pulses or bursts of pulses being separated by between about 1 and 5 Hz (e.g., between 2-5 Hz, between 2-4 Hz, about 3 Hz, etc.). In FIG. 17, the waveform includes one or a burst of biphasic pulses (if more than 1 pulse is included as a burst, the individual pulses are applied at about 3 Hz) are applied at a frequency of about 100 Hz.

As generally described herein skilled movements (such as movements involving any of the patient's fingers, hands, wrists, arms, toes, feet, ankles, legs, head, etc.) typically rely on a coordinated cortical and subcortical network. The methods and apparatuses described herein may generally improve coordination of a subject's cortical and subcortical networks. Thus, any of the methods and apparatuses described herein may be referred to as methods of improving a patient's motor coordination. These methods and apparatuses may be used to treat a variety of indications involving coordinated movement, including but not limited to stroke. The methods and apparatuses described herein may enhance the association of movement-related single-trial ensemble spiking in both cortical and sub-cortical structures along with increased cross-area alignment of spiking. These methods may provide consistent neural activity patterns across brain structures during recovery and modulation of cross-area coordination for enhancing motor function, including enhancing motor function post-stroke.

Any of the methods and apparatuses described herein may include selecting (e.g., optimizing) the parameters for sub-cortical stimulation of a patient in order to increase coordination of cortical and subcortical networks. These methods and apparatuses may include or may refer to an evaluation phase following sampling within a predetermined range of values for predefined parameters. For example, these methods and apparatuses may include application of subcortical stimulation to the thalamus. Following coupling of the electrodes to the subcortical (e.g., thalamic) region, the apparatus or method may determine a transfer function for applying stimulation to the subcortical region to enhance coordination with a cortical region. Sensing electrodes (implanted, internal or external) may be used to detect spiking patterns (and/or "rhythms" or coordinated neuronal activity, such as beta frequencies) following the application of the predetermined range of parameter valves, and a transfer function and/or stimulation parameters may be estimated. This transfer function may then be used to set the treatment parameters, e.g., by identifying parameters to optimize the evoked cortical spiking pattern, and/or for which the cortical spiking pattern is coordinated with the applied sub-cortical stimulation. In particular, the methods and apparatuses described herein may include determining a phase locking valve between the applied sub-cortical charge-balanced, low-frequency alternating current stimulation and the sensed cortical spiking as discussed above. For example the methods and apparatuses described herein may determine stimulation parameters (e.g., a transfer function) in which the phase locking value is between 0.5 and 0.95 (e.g., between 0.5 and 0.9, between 0.5 and 0.85, between 05 and 0.8, between 0.5 and 0.75, between 0.5 and 0.7, between 0.55 and 0.95, between 0.55 and 0.9, between 0.55 and 0.85, between 0.55 and 0.8, between 0.55 and 0.75, between 0.6 and 0.95, between 0.6 and 0.9, between 0.6 and 0.85, etc.). In some cases the method and/or apparatus may select stimulation parameters and/or transfer function in which the phase locking value is 0.95 or less (e.g., about 0.95 or less, 0.9 or less, 0.85 or less, 0.8 or less, 0.75 or less, 0.7 or less, 0.65 or less, 0.6 or less, etc.) and 0.4 or more (e.g., about 0.4 or more, 0.45 or more, 0.5 or more, 0.55 or more, 0.6 or more, 0.65 or more, 0.7 or more, 0.75 or more, 0.8 or more, 0.85 or more, etc.).

For example, described herein is subcortical (e.g., thalamic) evaluation of a transfer function as described, and then subcortical stimulation using the stimulation parameters (e.g., transfer function) to generate bursting and burst patterns cortically. The stimulation parameters may be determined using, e.g., a burst of charge-balanced, low-frequency pulses (e.g., a 1-5 Hz stim pattern with bursts of 10-200 Hz per stim pattern) from a subcortical site can be used, in which any combination of: amplitude, pulse width, and number of pulses are varied. Determining the stimulation parameters and/or transfer function may include determining a phase locking valve (PLV) between the applied sub-cortical charge-balanced, low-frequency alternating current stimulation and the sensed cortical spiking, e.g., measuring of the phase synchrony between the applied subcortical stimulation and cortical firing or spiking. The optimal phase locking value may typically be with a range that excludes "perfect" correlation, e.g., the phase locking value may be 0.95 or less (e.g., about 0.95, 0.94, 0.93, 0.92, 0.91, 0.9, 0.89, 0.88, 0.87, 0.86, 0.85, 0.84, 0.83, 0.82, 0.81, 0.8, 0.75, 0.7, 0.65, etc. or less) and may be 0.4 or more (e.g., about 0.4 or more, 0.45 or more, 0.5 or more, 0.55 or more, 0.6 or more, 0.65 or more, 0.7 or more, 0.75 or more, 0.8 or more, 0.85 or more, etc.). For example, the target PLV range may be between 0.4 and 0.95 (e.g., between 0.5 and 0.95, between 0.5 and 0.92, between 0.55 and 0.91, etc.).

For example, FIGS. 18A-18D, 19A-19D and 20A-20D show a parametric assessment (evaluation) of low-frequency oscillations in cortex as a function of varying electrical stimulation parameters applied from a sub-cortical region (e.g., thalamus). In these figures, each test waveform was applied as indicated above each graph. In each graph, the black dots are single spikes from neurons and the gray trace is the population spike rate. Evoked activity was found to be dependent on the burst frequency (e.g. 3 Hz below), the number of pulses in the burst, current amplitude and the duration of the pulse (PW=pulse width). This relationship may be mapped for an individual into which sub-cortical stimulation is to be applied) and in some examples may be customized and optimized to the individual to ensure optimal efficacy. For example, a cortical grid may be used to determine the exact relationship between the applied stimulation parameters and LFO amplitude. This may be mapped to behavioral improvements using a range of motor tasks (e.g., pressing a button, picking up a cup, picking up a coin, etc.). This can be done both intraoperatively or during awake behaviors.

Thus in some examples a treatment may include inserting one or more subcortical electrodes and applying a range (e.g., a matrix) of ACS parameters within an initial parameter space. For example, the parameter space may include the amplitude of the biphasic pulses, the pulse width of the biphasic pulses, the number of biphasic pulses in a burst of pulses, the frequency of pulses within each burst (inter-burst frequency), and/or the frequency of bursts. In the example shown in FIGS. 18A-18D, 19A-19C and 20A-20D, optimal responses were identified with between 3-5 pulses and pulse width of between 0.5 ms and 1 ms when the frequency of the bursts was 100 Hz and the inter-burst frequency was 3 Hz.

In any of the methods and apparatuses described herein, beta frequencies (e.g., frequencies between about 10-40 Hz) may be used as feedback to control the application of ACS, e.g., sub-cortical ACS. Beta frequencies may be recorded using either a cortical lead or a subcortical lead, or externally (e.g., EEG). The power within the beta frequencies may be used. For example, FIG. 21A-21B show average beta power at either 13 days post stroke (FIG. 21A) or 20 days post-stroke (FIG. 21B). As shown, every early post-stroke there is a significant amount of beta frequency power during movement, which goes away with recovery (e.g., at –0.5-0 time to movement there is a marked drop in beta between 13 days and 20 days post-stroke). Low frequency oscillations (LFOs) are present during this period. The methods and apparatuses described herein may turn on electrical stimulation at the peak of beta and immediately prior to movement onset.

As mentioned above, also described herein are systems for performing any of the methods described herein. For example, described herein are systems for treating a patient, the system comprising: one or more sensors configured to detect a directed movement or an intended directed movement from the patient; a plurality of electrodes; one or more processors; and a memory coupled to the one or more processors, the memory configured to store computer-program instructions, that, when executed by the one or more processors, perform a computer-implemented method comprising: applying a charge-balanced, low-frequency alternating current stimulation (ACS) to the plurality of electrodes immediately before and/or during a detected directed movement, wherein the charge-balanced, low-frequency ACS has a depolarizing phase with a frequency of 15 Hz or less and a hyperpolarizing phase with a frequency greater than 15 Hz, wherein the ACS stimulation field is greater than 1.5 V/m.

For example, FIG. 22 schematically illustrates one example of an apparatus (e.g., system) as described herein, including a sensor 2205 (which may be a plurality of sensors). These sensors may be electrodes configured to sense electrical activity within the brain (e.g., from a motor or premotor region). The sensor may include hardware, software of firmware (e.g., within the controller 2205) for identifying or detecting directed movements (e.g., limb movement, hand movement, foot movement, etc.) in the patient. In some examples the sensors may include one or more motion sensors, e.g., accelerometers. In some examples the sensors may include electromyography sensors. These sensors may include any of the sensors descried herein. The sensors may be directly (e.g., via a lead or wire) or wirelessly connected to the controller and/or processor 2205.

The apparatuses (e.g., systems) described herein may also or alternatively include one a plurality of electrodes 2221. These electrodes may be implantable electrodes, including paddle electrodes, needle electrodes, ring electrodes, microelectrodes, etc. these electrodes may be configured for implantation into a subcortical region (e.g., thalamus, brainstem, etc.). The electrodes may be connected to the controller and/or processor 2205 directly (e.g., via a lead or wire) or wirelessly to the controller and/or processor 2205.

The apparatuses described herein may include a controller 2205 that may be internal (e.g., implantable) or external (e.g., wearable). The controller may include a housing enclosing all of some of the components, such as the memory 2209, processor 2207, signal generator (e.g., pulse generator) 2211, power supply (e.g., battery, capacitor, batteryless and/or wireless power supply, inductive power supply, etc.). The input/output may be a wireless communication circuitry and may communicate and/or receive instructions from a remote server; the controller may store, transmit and receive data from one or more remote servers.

The controller may also include one or more inputs and/or one or more outputs. For example, the controller may include a pulse generator that is configured to generate the charge-balanced, low-frequency alternating current stimulation (ACS) for application to the patent by the plurality of electrodes. In some examples the pulse generator may be configured and/or controlled to generate a charge-balanced, low-frequency ACS having a depolarizing phase with a frequency of 15 Hz or less and a hyperpolarizing phase with a frequency greater than 15 Hz, wherein the ACS stimulation field is greater than 1.5 V/m. In general, the pulse generator may be configured to generate the waveforms described herein that are configured to provide ACS subcortically.

In general, the memory storing the instructions may include instructions for performing any of the methods steps described herein by the apparatus. For example, the computer-implemented method may further comprises: applying the charge-balanced, low-frequency ACS in phase with a majority of units of the region of the patient's brain within an excitable zone of the region of the patient's brain. The computer-implemented method may further comprises: determining the excitable zone by stimulating the region during non-movement periods or under anesthesia to determine a frequency and phase relationship of entrainment of the region. The computer-implemented method may further comprise determining a preferred open-loop stimulation period or a closed-loop stimulation period using the frequency and phase relationship of entrainment, where the charge-balanced, low-frequency ACS is applied in phase with the preferred open-loop period or closed-loop stimulation period. The computer-implemented method further comprises: applying the charge-balanced, low-frequency ACS to a region of the patient's brain is adjacent to a lesion of the patient's brain. As mentioned, the computer-implemented method may further comprise detecting the directed movement or the intended directed movement by sensing brain activity.

Any of these systems may be configured to apply the charge-balanced, low-frequency ACS epidurally. For example, the electrodes 2221 could be epidural electrodes. In some examples the electrodes 2221 may be configured for insertion into a blood vessel (e.g., within the neurovasculature). For example, the computer-implemented method may further comprise applying the charge-balanced, low-frequency ACS from within a blood vessel.

Any of these systems may include one or more sensors or sensing subsystems to determine when the patient is awake or asleep (e.g., movement sensors, sleep sensors, etc.) and application of the charge-balanced, low-frequency ACS may be suppressed or suspended when the patient is sleeping.

Also described herein are non-transitory computer-readable medium including contents that are configured to cause one or more processors to perform a method comprising: detecting a directed movement or an intended directed movement from the patient; and applying a charge-balanced, low-frequency alternating current stimulation (ACS) to a subcortical region of the patient's brain immediately before and/or during the directed movement, wherein the charge-balanced, low-frequency ACS has a depolarizing phase with a frequency of 15 Hz or less and a hyperpolarizing phase with a frequency greater than 15 Hz, wherein the ACS stimulation field is greater than 1.5 V/m.

Also described herein are methods of determining a transfer function and/or stimulation parameters for applying sub-cortical stimulation to improve a patient's motor coordination. These methods may include: applying, from a subcortical site, a plurality of bursts of charge-balanced, low-frequency pulses having a burst frequency of between 1-10 Hz, an inter-burse pulse frequency of between 10-200 Hz, and a pulse width of between about 0.01 ms and 2 ms, wherein the bursts of charge-balanced, low-frequency pulses each comprises between about 1 and 20 pulses per burst; sensing a pattern of neural activity from a cortical region in response to the applied bursts of charge-balanced, low-frequency pulses; and determining a stimulation parameters (and/or transfer function) from the sensed pattern of neural activity from a cortical region in response to the applied bursts of charge-balanced, low-frequency pulses. These methods may include treating a patient by applying stimulation according to the stimulation parameters (e.g., transfer function). For example, treating the patient may comprise treating the patient recovering from a stroke. The subcortical region may comprise a thalamic region.

Sensing the pattern of neural activity may comprise recording an electroencephalogram (EEG), recording from a plurality of cortical electrodes, etc. Determining stimulation parameters and/or the transfer function may comprise identifying parameters to maximize the pattern of neural activity from the cortical region.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating a patient, the method comprising:
   detecting a directed movement or an intended directed movement from the patient; and
   applying a charge-balanced, low-frequency alternating current stimulation (ACS) to a region of the patient's brain immediately before and/or during the directed movement, wherein the charge-balanced, low-frequency ACS has a depolarizing phase with a frequency of 15 Hz or less and a hyperpolarizing phase with a frequency greater than 15 Hz, wherein applying the charge-balanced, low-frequency ACS to the region of the patient's brain comprises applying the charge-balanced, low-frequency ACS to a region of the patient's brain that is adjacent to a lesion of the patient's brain;
wherein the ACS field strength is greater than 1.5 V/m.

2. The method of claim 1, wherein the charge-balanced, low-frequency ACS is applied in phase with a majority of unit of the region of the patient's brain, within an excitable zone of the majority of units of the region of the patient's brain.

3. The method of claim 2, further comprising determining the excitable zone by stimulating the region during non-movement periods or under anesthesia to determine a frequency and phase relationship of entrainment of the region.

4. The method of claim 3, wherein the frequency and phase relationship of entrainment of the region is frequency and/or current amplitude dependent.

5. The method of claim 3, further comprising determining a preferred open-loop stimulation period or a closed-loop stimulation period using the frequency and phase relationship of entrainment, where the charge-balanced, low-frequency ACS is applied in phase with the preferred open-loop period or closed-loop stimulation period.

6. The method of claim 2, further comprising determining properties of the ACS using a feedforward or recurrent neural network (RNN).

7. The method of claim 6, wherein the feedforward or RNN is modified based on actual measurements of the frequency, amplitude and phase dependence of the excitable zone.

8. The method of claim 1, wherein the directed movement is a reaching or reaching and grasping movement.

9. The method of claim 1, wherein detecting the directed movement or the intended directed movement comprises sensing brain activity.

10. The method of claim 1, wherein detecting the directed movement or intended directed movement comprises detecting an electromyographic signal.

11. The method of claim 1, wherein detecting the directed movement or intended directed movement comprises detecting body motion using a motion sensor.

12. The method of claim 1, wherein the method is a method of treating a brain lesion.

13. The method of claim 1, wherein the method is a method of treating stroke, chronic small vessel disease seen with aging, and/or traumatic brain injury.

14. The method of claim 1, wherein the charge-balanced, low-frequency ACS is applied epidurally.

15. The method of claim 1, wherein the charge-balanced, low-frequency ACS is applied from within a blood vessel.

16. The method of claim 1, further comprising suppressing application of the charge-balanced, low-frequency ACS when the patient is sleeping.

17. The method of claim 1, further comprising identifying stimulation parameters by applying, from a subcortical site, a plurality of bursts of charge-balanced, low-frequency pulses having a burst frequency of between 1-10 Hz, an inter-burse pulse frequency of between 10-200 Hz, and a pulse width of between about 0.01 ms and 2 ms, wherein the bursts of charge-balanced, low-frequency pulses each comprises between about 1 and 20 pulses per burst.

18. The method of claim 17, wherein applying the charge-balanced, low-frequency alternating current stimulation comprises using the stimulation parameters when applying the charge-balanced, low-frequency alternating current stimulation.

19. A system for treating a patient, the system comprising:
one or more sensors configured to detect a directed movement or an intended directed movement from the patient, wherein the one or more sensors comprise electrodes configured to detect neural or neuromuscular activity;
a plurality of electrodes;
one or more processors; and
memory coupled to the one or more processors, the memory configured to store computer-program instructions, that, when executed by the one or more processors, perform a computer-implemented method comprising:
applying a charge-balanced, low-frequency alternating current stimulation (ACS) to the plurality of electrodes immediately before and/or during a detected directed movement, wherein the charge-balanced, low-frequency ACS has a depolarizing phase with a frequency of 15 Hz or less and a hyperpolarizing phase with a frequency greater than 15 Hz, wherein the ACS field strength is greater than 1.5 V/m.

20. The system of claim 19, wherein the computer-implemented method further comprises: applying the charge-balanced, low-frequency ACS in phase with a majority of units of the region of the patient's brain within an excitable zone of the region of the patient's brain.

21. The system of claim 20, wherein the computer-implemented method further comprises: determining the excitable zone by stimulating the region during non-movement periods or under anesthesia to determine a frequency and phase relationship of entrainment of the region.

22. The system of claim 20, wherein the computer-implemented method further comprises determining a preferred open-loop stimulation period or a closed-loop stimulation period using the frequency and phase relationship of entrainment, where the charge-balanced, low-frequency ACS is applied in phase with the preferred open-loop period or closed-loop stimulation period.

23. The system of claim 19, wherein the computer-implemented method further comprises: applying the charge-balanced, low-frequency ACS to a region of the patient's brain is adjacent to a lesion of the patient's brain.

24. The system of claim 19, wherein the one or more sensors comprise movement sensors.

25. The system of claim 19, wherein the computer-implemented method further comprises detecting the directed movement or the intended directed movement by sensing brain activity.

26. The system of claim 19, wherein the computer-implemented method further comprises applying the charge-balanced, low-frequency ACS epidurally.

27. The system of claim 19, wherein the computer-implemented method further comprises applying the charge-balanced, low-frequency ACS from within a blood vessel.

28. The system of claim 19, wherein the computer-implemented method further comprises applying the charge-balanced, low-frequency ACS, further comprising suppressing application of the charge-balanced, low-frequency ACS when the patient is sleeping.

29. A non-transitory computer-readable medium including contents that are configured to cause one or more processors to perform a method comprising:
detecting a directed movement or an intended directed movement from the patient; and
applying a charge-balanced, low-frequency alternating current stimulation (ACS) to a subcortical region of the patient's brain immediately before and/or during the directed movement, wherein the charge-balanced, low-frequency ACS has a depolarizing phase with a frequency of 15 Hz or less and a hyperpolarizing phase with a frequency greater than 15 Hz, wherein the ACS field strength is greater than 1.5 V/m.

30. A method of treating a patient, the method comprising:
detecting a directed movement or an intended directed movement from the patient; and
applying a charge-balanced, low-frequency alternating current stimulation (ACS) to a region of the patient's brain immediately before and/or during the directed movement, wherein the charge-balanced, low-frequency ACS has a depolarizing phase with a frequency of 15 Hz or less and a hyperpolarizing phase with a frequency greater than 15 Hz, further wherein the charge-balanced, low-frequency ACS is applied from within a blood vessel;
wherein the ACS field strength is greater than 1.5 V/m.

31. A method of treating a patient, the method comprising:
detecting a directed movement or an intended directed movement from the patient; and
applying a charge-balanced, low-frequency alternating current stimulation (ACS) to a region of the patient's brain immediately before and/or during the directed movement, wherein the charge-balanced, low-frequency ACS has a depolarizing phase with a frequency of 15 Hz or less and a hyperpolarizing phase with a frequency greater than 15 Hz;
wherein the ACS field strength is greater than 1.5 V/m; and
suppressing application of the charge-balanced, low-frequency ACS when the patient is sleeping.

32. A system for treating a patient, the system comprising:
one or more sensors configured to detect a directed movement or an intended directed movement from the patient, wherein the one or more sensors comprise movement sensors;
a plurality of electrodes;
one or more processors; and
memory coupled to the one or more processors, the memory configured to store computer-program instructions, that, when executed by the one or more processors, perform a computer-implemented method comprising:
applying a charge-balanced, low-frequency alternating current stimulation (ACS) to the plurality of electrodes immediately before and/or during a detected directed movement, wherein the charge-balanced, low-frequency ACS has a depolarizing phase with a frequency of 15 Hz or less and a hyperpolarizing phase with a frequency greater than 15 Hz, wherein the ACS field strength is greater than 1.5 V/m.

33. A system for treating a patient, the system comprising:
one or more sensors configured to detect a directed movement or an intended directed movement from the patient;
a plurality of electrodes;
one or more processors; and
memory coupled to the one or more processors, the memory configured to store computer-program instructions, that, when executed by the one or more processors, perform a computer-implemented method comprising:
applying a charge-balanced, low-frequency alternating current stimulation (ACS) to the plurality of electrodes immediately before and/or during a detected directed movement, wherein the charge-balanced, low-frequency ACS has a depolarizing phase with a frequency of 15 Hz or less and a hyperpolarizing phase with a frequency greater than 15 Hz, wherein the ACS field strength is greater than 1.5 V/m, wherein detecting the directed movement or the intended directed movement is detected by sensing brain activity.

* * * * *